United States Patent
Sato et al.

(10) Patent No.: US 10,765,729 B2
(45) Date of Patent: Sep. 8, 2020

(54) TUMOR ANTIGEN PEPTIDE

(71) Applicants: Sapporo Medical University, Sapporo-shi, Hokkaido (JP); Sumitomo Dainippon Pharma Co., Ltd., Osaka-shi, Osaka (JP)

(72) Inventors: Noriyuki Sato, Sapporo (JP); Toshihiko Torigoe, Sapporo (JP); Yoshihiko Hirohashi, Sapporo (JP); Takayuki Kanaseki, Sapporo (JP); Sho Miyamoto, Sapporo (JP); Vitaly Kochin, Sapporo (JP); Masashi Goto, Osaka (JP)

(73) Assignees: Sapporo Medical University, Sapporo-shi, Hokkaido (JP); Sumitomo Dainippon Pharma Co., Ltd., Osaka-shi, Osaka (JP)

( * ) Notice: Subject to any disclaimer, the term of this patent is extended or adjusted under 35 U.S.C. 154(b) by 0 days.

(21) Appl. No.: 15/534,315

(22) PCT Filed: Dec. 8, 2015

(86) PCT No.: PCT/JP2015/084428
§ 371 (c)(1),
(2) Date: Jun. 8, 2017

(87) PCT Pub. No.: WO2016/093243
PCT Pub. Date: Jun. 16, 2016

(65) Prior Publication Data
US 2017/0360911 A1 Dec. 21, 2017
US 2018/0147270 A9 May 31, 2018

(30) Foreign Application Priority Data

Dec. 9, 2014 (JP) ................................ 2014-249169

(51) Int. Cl.
| | | |
|---|---|---|
| A61K 38/00 | (2006.01) |
| A61K 39/00 | (2006.01) |
| C07K 16/30 | (2006.01) |
| A61K 48/00 | (2006.01) |
| C12Q 1/68 | (2018.01) |
| G01N 33/50 | (2006.01) |
| G01N 33/574 | (2006.01) |
| A61P 35/00 | (2006.01) |
| C07K 14/47 | (2006.01) |
| C07K 7/06 | (2006.01) |
| C07K 16/28 | (2006.01) |

(Continued)

(52) U.S. Cl.
CPC .... *A61K 39/0011* (2013.01); *A61K 39/00118* (2018.08); *A61K 48/00* (2013.01); *A61P 35/00* (2018.01); *C07K 7/06* (2013.01); *C07K 14/47* (2013.01); *C07K 14/4748* (2013.01); *C07K 16/2833* (2013.01); *C07K 16/30* (2013.01); *C12N 5/0638* (2013.01); *C12Q 1/68* (2013.01); *C12Q 1/6886* (2013.01); *G01N 33/5011* (2013.01); *G01N 33/5088* (2013.01); *G01N 33/574* (2013.01); *G01N 33/57484* (2013.01); *A61K 2039/572* (2013.01); *A61K 2039/82* (2018.08); *C07K 2317/34* (2013.01); *C12Q 2600/136* (2013.01); *C12Q 2600/158* (2013.01); *C12Q 2600/178* (2013.01); *G01N 2333/46* (2013.01); *G01N 2333/70539* (2013.01)

(58) Field of Classification Search
None
See application file for complete search history.

(56) References Cited

U.S. PATENT DOCUMENTS 8,586,006 B2 * 11/2013 Hood .................. G01N 33/6845
424/1.11
2002/0048763 A1 * 4/2002 Penn ...................... C07K 14/47
435/6.11
(Continued)

FOREIGN PATENT DOCUMENTS

WO WO 2002/081622 A2 10/2002
WO WO 2008/054597 A2 5/2008
(Continued)

OTHER PUBLICATIONS

Kataja et al., Ann Oncol 2009; 20(sup 4): iv10-14 (Year: 2009).*
(Continued)

*Primary Examiner* — Sheela J. Huff
(74) *Attorney, Agent, or Firm* — Wolf, Greenfield & Sacks, P.C.

(57) ABSTRACT

The purpose of the present invention is to provide: a detection agent for specifically detecting a cancer stem cell; a tumor antigen peptide specifically presented by cancer stem cells; a medicinal composition useful in preventing and/or treating cancer, said medicinal composition comprising the aforementioned tumor antigen peptide as an active ingredient; a method for screening the tumor antigen peptide; etc. To achieve the above-mentioned purpose, provided are: peptides represented by $Y_O$-$X_O$-$Z_O$; a polyepitope peptide consisting of a plurality of epitope peptides connected together, said polyepitope peptide containing at least one of the above-mentioned peptides as one of the epitope peptides; a polynucleotide encoding the aforementioned peptides and/or polyepitope peptide; a medicinal composition comprising the same as an active ingredient; a prophylactic and/or therapeutic agent for cancer characterized by inducing CTL; etc.

29 Claims, 23 Drawing Sheets

Specification includes a Sequence Listing.

(51) Int. Cl.
C12N 5/0783 (2010.01)
C12Q 1/6886 (2018.01)

(56) References Cited

U.S. PATENT DOCUMENTS

2007/0248628 A1 10/2007 Keller et al.
2011/0262358 A1 10/2011 Torigoe et al.

FOREIGN PATENT DOCUMENTS

WO  WO 2010/050190 A1  5/2010
WO  WO 2010/050268 A1  5/2010
WO  WO 2013/143504 A1  10/2013

OTHER PUBLICATIONS

Nelson et al., Ann. Intern Med. 2009; 151:727-737 (Year: 2009).*
Ferguson et al Molecular and Cellular Biology vol. 27 p. 6407 (2007). (Year: 2007).*
Balmana et al. Ann Oncol 2009; 20(supp 4):iv19-20 (Year: 2009).*
Campbell, Monoclonal Antibody Technology Eds. Elseiver p. 1-32 (1984) (Year: 1984).*
Che et al., An integrated microfluidic system for screening of peptides specific to colon cancer cells and colon cancer stem cells using the phage display technology. 9th IEEE International Conference on Nano/micro engineered and molecular systems. Apr. 13-16, 2014. pp. 440-443.
Miyamoto et al., The antigen ASB4 on cancer stem cells serves as a target for CTL immunotherapy of colorectal cancer. Cancer Immunol Res. Jan. 25, 2018; 6(3): 358-369. doi: 10.1158/2326-6066.CIR-17-0518. [Epub ahead of print].
Au et al., Expression of ankyrin repeat and SOCS box containing 4 (ASB4) confers migration and invasion properties of hepatocellular carcinoma cells. Biosci Trends. Apr. 2014;8(2):101-10.
Hirohashi et al., Gan Kansaibo o Hyoteki to shita Men'eki Ryoho no Kisoteki Kento. (Establishment of cancer stem cell-targeting immunotherapy.) Nippon Byori Gakkai Kaishi. 2010;99(1):187. 1-D-4.
Kile et al., Cloning and characterization of the genes encoding the ankyrin repeat and SOCS box-containing proteins Asb-1, Asb-2, Asb-3 and Asb-4. Gene. Nov. 27, 2000;258(1-2):31-41.
Kim et al., Compartmentalization of vertebrate optic neuroephithelium: external cues and transcription factors. Mol Cells. Apr. 2012;33(4):317-24. doi:10.1007/s10059-012-0030-5. Epub Mar. 23, 2012.
Mizuno et al., Asb4, Ata3, and Dcn are novel imprinted genes identified by high-throughput screening using RIKEN cDNA microarray. Biochem Biophys Res Commun. Feb. 8, 2002;290(5):1499-505.
Morita et al., Daichogan Gan Kansaibo to Shinki Gan Kogen OR7C1 no Bunshi Byorigakuteki Kaiseki. (Molecular pathological analysis of human colon cancer stem cells and its novel antigen OR7C1.) Nippon Byori Gakkai Kaishi. 2012;101(1):349. P1-PM-158.
Morita et al., Daichogan ni Okeru Gan Kansaibo to Shinki Gan Kogen no Bunshi Byoriteki Kaiseki. (Molecular pathological analysis of novel antigens expressed in colon cancer stem cells.) Nippon Byori Gakkai Kaishi. 2010;99(1):246. P1-I-14.
Yang et al., Genome-wide functional analysis reveals factors needed at the transition steps of induced reprogramming. Cell Rep. Jul. 24, 2014;8(2):327-37. doi: 10.1016/j.celrep.2014.07.002. Epub Jul. 17, 2014.

* cited by examiner

Cloning of SW480-SP and SW480-MP cells.

FIG. 2-2
Sphere-forming ability of SW480-SP and SW480-MP cells.
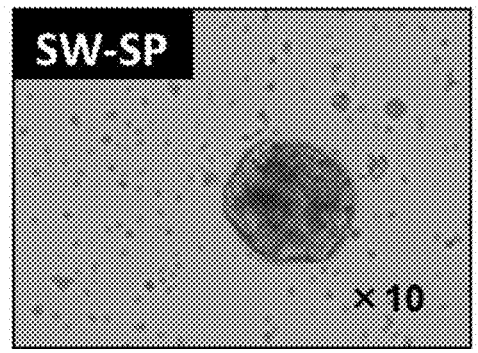 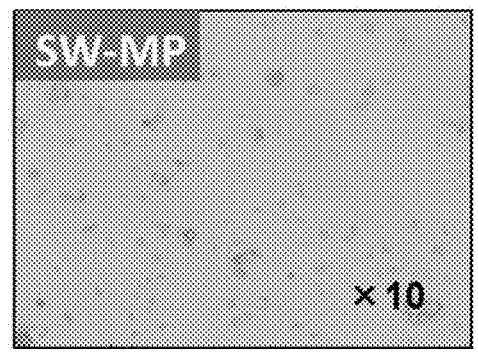

FIG. 4

ASB4

MDGTTAPVTKSGAAKIVKRNFLEALKSNDFGKLKAILIQRQIEVDTVFEVEDENMVLASYKQGYWLPSYK
LKSSWATGLHLSVLFGHVECLLVLLDHNATINCRPNGKTPLHVACEMANVDCVKILCDRGAKLNCYSLSG
HTALHFCTTPSSILCAKQLVWRGANVNMKTNNQDEETPLHTAAHFGLSELVAFYVEHGAIVDSVNAHMET
PLAIAAYWALRFKEQEYSTEHHLVCRMLLDYKAEVNARDDDFKSPLHKAAWNCDHVLMHMMLEAGAEANL
MDINGCAAIQYVLKVTSVRPAAQPEICYQLLLNHGAARIYPPQFHKYIQACHSCPKAIEVVVNAYEHIRW
NTKWRRAIPDDDLEKYWDFYHSLFTVCCNSPRTLMHLSRCAIRRTLHNRCHRAIPLLSLPLSLKKYLLLE
PEGIIY

HLA-A24 naturally processed peptide, IV9

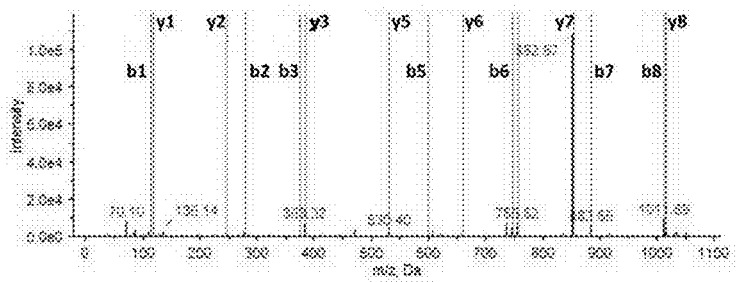

FIG. 5

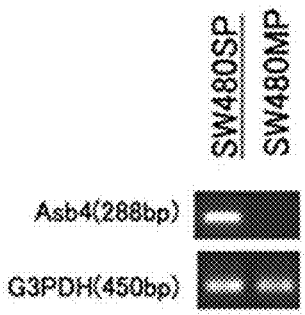

FIG. 6

Expression of ASB4 gene
in human adult normal tissues.

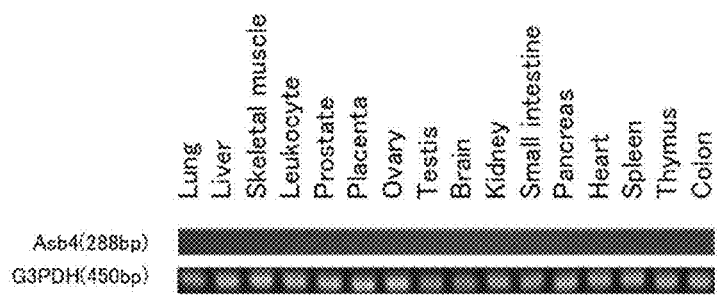

Expression of ASB4 gene in cancer cell lines.

TUMOR ANTIGEN PEPTIDE

RELATED APPLICATION

This application is a national stage filing under 35 U.S.C. § 371 of International Application No. PCT/JP2015/084428, filed Dec. 8, 2015, entitled "Tumor Antigen Peptide," the contents of which is herein incorporated by reference in its entirety.

TECHNICAL FIELD

The present invention relates to a detecting agent for detecting a cancer stem cell by using a gene that is specifically expressed in a cancer stem cell, a tumor antigen peptide derived from the gene, which is useful as a preventive and/or therapeutic agent for cancer, and the use thereof. Furthermore, the present invention relates to a method for screening such a tumor antigen peptide.

BACKGROUND ART

The therapeutic effect of anticancer agents that have been developed so far is not sufficient and the probability of curing a cancer is very low. As a cause thereof, the inability of conventional therapeutic agents to selectively target cells that form the basis of cancer tissue can be cited. In recent years, as such 'cells forming the basis of cancer tissue' the presence of cancer stem cells has been reported. Cancer stem cells are thought to be causal cells involved in the occurrence, recurrence, and metastasis of a cancer and, therefore, if cancer stem cells can be targeted, it can be expected that the possibility of suppressing effectively the proliferation, recurrence, and metastasis of a cancer will be high. That is, the development of a technique for detecting cancer stem cells and a novel therapeutic agent that targets cancer stem cells are important issues in cancer medicine.

On the other hand, in the elimination of tumor cells and virus-infected cells, etc. in a living body, cell-mediated immunity, in particular involving cytotoxic T cells (CTLs), plays an important role. In the case of the elimination of tumor cells, a CTL recognizes a complex of an antigen peptide (tumor antigen peptide) and a major histocompatibility complex (MHC: Major Histocompatibility Complex) class I antigen (called an HLA class I antigen in the case of humans) on a tumor cell and attacks and destroys the tumor cell. That is, a tumor antigen peptide is produced by intracellular degradation by a protease of a tumor-specific protein, that is, a tumor antigen protein, after it has been synthesized in the cell. The tumor antigen peptide thus produced binds to an MHC class I antigen (HLA class I antigen) in the endoplasmic reticulum to form a complex, which is transported to the cell surface and is presented as an antigen. A tumor-specific CTL recognizes the complex involved in this antigen presentation, and an anti-tumor effect is exhibited via cytotoxic action, lymphokine production, etc. Accompanying the elucidation of such a series of actions, therapies in which a tumor antigen protein or a tumor antigen peptide is utilized as a so-called cancer immunotherapy agent (cancer vaccine) to thus enhance cancer-specific CTLs in the body of a cancer patient are in the process of being developed.

Among them, the development of a novel cancer vaccine that can immunologically eliminate cancer stem cells has been particularly desired (e.g. Patent Document 1).

Ankyrin repeat and SOCS box-containing 4 (ASB4) is one of the genes originally identified in the process of imprinting gene screening, but in recent years it has also been identified as a gene involved in reprogramming, and it is known that its expression is not observed except for the testes of specific differentiation stage in human normal tissues. As events related to ASB4 and cancer, it has been reported that ASB4 is expressed in hepatoma cells and that the expression of ASB4 gene positively correlates with tumor invasiveness (for example, Non-Patent Documents 1 to 4).

PRIOR ART DOCUMENTS

Patent Documents

[Patent Document 1] International Patent Application WO2010/050268

Non-Patent Documents

[Non-Patent Document 1] Mizuno Y, et al. Biochem Biophys Res Commun. 2002 Feb. 8; 290(5): 1499-505.
[Non-Patent Document 2] Yang C S, et al. Cell Rep. 2014 Jul. 24; 8(2): 327-37.
[Non-Patent Document 3] Kim S K, et al. Mol Cells. 2008 Apr. 30; 25(2): 317-21.
[Non-Patent Document 4] Au V, et al. Biosci Trends. 2014 Apr.; 8(2): 101-10.

SUMMARY OF THE INVENTION

Problems to be Solved by the Invention

It is an object of the present invention to provide a detecting agent that specifically detects a cancer stem cell, a tumor antigen peptide that is specifically presented on a cancer stem cell, a pharmaceutical composition useful for the prevention and/or therapy of a cancer containing the above as an active ingredient, a method for screening such tumor antigen peptide, etc.

Means for Solving the Problems

While searching for a peptide that is specifically subjected to antigen presentation on a tumor cell, and in particular on a cancer stem cell, even if a plurality of epitope regions that are predicted to bind to an HLA exist in the sequence of a protein specifically expressed in the cancer stem cell, it is not easy to identify which portion of the protein actually binds to an HLA in a living body and is subjected to antigen presentation on the cell surface. Therefore, in order to solve such problems, the present inventors have developed a method for directly identifying a peptide that is actually presented as an antigen on a cancer stem cell (natural peptide) and have identified several natural peptides. It has been found that among such peptides, a peptide that is specifically presented as an antigen only on a cancer stem cell is a peptide derived from an ASB4 protein, and as a result of further intensive investigation the present invention has been accomplished.

That is, the present invention relates to the following:
[1] An antigen peptide specific to cancer stem cells represented by $Y_0$-$X_0$-$Z_0$, wherein
$X_0$ is any of (1) to (4) below:
(1) a partial peptide of an ASB4 protein consisting of 8 to consecutive amino acids in the amino acid sequence of the protein, the second amino acid from the N terminal being leucine, isoleucine, or methionine, and/or the amino acid at the C terminal being valine, leucine, or isoleucine;

(2) a peptide which, in the partial peptide defined in (1), the second amino acid from the N terminal being replaced by leucine, isoleucine or methionine, and/or the amino acid at the C terminal being replaced by valine, leucine or isoleucine;

(3) a partial peptide of the ASB4 protein consisting of 8 to 14 consecutive amino acids in the amino acid sequence of the protein, the second amino acid from the N terminal being tyrosine, phenylalanine, methionine, or tryptophan, and/or the amino acid at the C terminal being leucine, isoleucine, or phenylalanine; or (4) a peptide which, in the partial peptide defined in (3), the second amino acid from the N terminal being replaced by tyrosine, phenylalanine, methionine or tryptophan, and/or the amino acid at the C terminal being replaced by leucine, isoleucine or phenylalanine; and, $Y_0$ and $Z_0$ are mutually independently a peptide consisting of 0 to several amino acids.

[2] The antigen peptide according to [1], wherein $X_0$ is any of (1') to (4') below:

(1') a partial peptide of the ASB4 protein consisting of 8 to 11 consecutive amino acids in the amino acid sequence of the protein, the second amino acid from the N terminal being leucine, isoleucine, or methionine, and/or the amino acid at the C terminal being valine, leucine, or isoleucine;

(2') a peptide which, in the partial peptide defined in (1'), the second amino acid from the N terminal being replaced by leucine, isoleucine or methionine, and/or the amino acid at the C terminal being replaced by valine, leucine or isoleucine;

(3') a partial peptide of the ASB4 protein consisting of 8 to 11 consecutive amino acids in the amino acid sequence of the protein, the second amino acid from the N terminal being tyrosine, phenylalanine, methionine, or tryptophan, and/or the amino acid at the C terminal being leucine, isoleucine, or phenylalanine; or (4') a peptide which, in the partial peptide defined in (3'), the second amino acid from the N terminal being replaced by tyrosine, phenylalanine, methionine or tryptophan, and/or the amino acid at the C terminal being replaced by leucine, isoleucine or phenylalanine; and, $Y_0$ and $Z_0$ are mutually independently 0 or one amino acid; or a peptide consisting of 0 to three amino acids such that the entire $Y_0$-$X_0$-$Z_0$ consists of a partial peptide of the ASB4 protein having a length of 9 to 14 amino acids or an $X_0$ homolog thereof.

[3] The antigen peptide according to [1] or [2], wherein $X_0$ consists of an amino acid sequence represented by any of SEQ ID Nos: 3 to 7, 9 to 19, 21 to 28, and 30 to 46.

[4] The antigen peptide according to [1] or [2], wherein $X_0$ consists of an amino acid sequence represented by any of SEQ ID Nos: 3 to 7, 9 to 19, 21 to 28, and 30 to 46; and $Y_0$ and $Z_0$ are not present.

[5] The antigen peptide according to [1] or [2], wherein $X_0$ consists of an amino acid sequence represented by any of SEQ ID Nos: 3 to 7, 9 to 11, 13 to 19, 21 to 23, 26 to 28, and 30 to 46, in which the second amino acid from the N terminal is replaced by methionine, leucine or isoleucine, and/or the amino acid at the C terminal is replaced by leucine, valine or isoleucine; and $Y_0$ and $Z_0$ are not present.

[6] The antigen peptide according to [1] or [2], wherein $X_0$ consists of an amino acid sequence represented by any of SEQ ID Nos: 3, 5 to 7, 9 to 14, 16, 19, 21 to 26, 28, 30 to 32, 34 to 37, and 39 to 46, in which the second amino acid from the N terminal is replaced by methionine or tyrosine, and/or the amino acid at the C terminal is replaced by leucine, isoleucine or phenylalanine; and $Y_0$ and $Z_0$ are not present.

[7] The antigen peptide according to [1] or [2], wherein $X_0$ is $X_0$ according to any one of [4] to [6], either one of $Y_0$ or $Z_0$ is one amino acid, and the other is not present.

[8] The antigen peptide according to any one of [1] to [3], wherein the peptide represented by $Y_0$-$X_0$-$Z_0$ consists of an amino acid sequence represented by any of SEQ ID Nos: 4, 6, 7, 10, 14, 15, 17 to 19, 21 to 23, 26, 28, 31, 33, 36, 39, 41, 42, 45 and 46.

[9] The antigen peptide according to any one of [1] to [3], wherein the peptide represented by $Y_0$-$X_0$-$Z_0$ consists of an amino acid sequence represented by any of SEQ ID Nos: 9, 21, 25, 30, 32, 35 and 37.

[10] The antigen peptide according to any one of [1] to [3], wherein the peptide represented by $Y_0$-$X_0$-$Z_0$ consists of an amino acid sequence represented by any of SEQ ID Nos: 4 to 12 and 15 to 23.

[11] The antigen peptide according to any one of [1] to [3], wherein the peptide represented by $Y_0$-$X_0$-$Z_0$ consists of an amino acid sequence represented by any of SEQ ID Nos: 3 to 9, 13, 14, 25, 26 and 28 to 30.

[12] The antigen peptide according to any one of [1] to [3], wherein the peptide represented by $Y_0$-$X_0$-$Z_0$ consists of an amino acid sequence represented by any of SEQ ID Nos: 4 to 9.

[13] A polyepitope peptide which comprises a plurality of epitope peptides linked together, wherein the polyepitope peptide comprises at least one antigen peptide according to any one of [1] to [12] as the epitope peptide.

[14] A cancer stem cell-detecting agent comprising an ASB4-detecting agent for detecting an expression product of the ASB4 gene.

[15] The cancer stem cell-detecting agent according to [14], wherein it detects a cancer stem cell in a cell population containing cells derived from one or more biological samples selected from the group consisting of heart, brain, placenta, lung, liver, skeletal muscle, kidney, pancreas, spleen, thymus, prostate, testis, ovary, small intestine, large intestine, and blood.

[16] The cancer stem cell-detecting agent according to [14] or [15], wherein an expression product of the ASB4 gene is an mRNA and/or an endogenous polypeptide.

[17] The cancer stem cell-detecting agent according to any one of [14] to [16], wherein the expression product of the ASB4 gene is an mRNA, and detection is carried out by an RT-PCR method.

[18] The cancer stem cell-detecting agent according to any one of [14] to [16], wherein the expression product of the ASB4 gene is an endogenous polypeptide, and detection is carried out by means of an ASB4-detecting agent that specifically reacts with the endogenous polypeptide.

[19] The cancer stem cell-detecting agent according to [18], wherein the ASB4-detecting agent is an antibody.

[20] The cancer stem cell-detecting agent according to any one of [14] to [17], wherein the ASB4-detecting agent is a probe and/or a primer having a base sequence that is complementary to the ASB4 gene, for detecting an mRNA that is an expression product of the ASB4 gene.

[21] A method for detecting cancer stem cells in a test subject using the cancer stem cell-detecting agent according to any one of [14] to [20].

[22] A method for screening a cancer treatment drug, the method comprising
  (i) a step of measuring a detected amount A of an expression product of the ASB4 gene in a subject before administering a candidate compound for a cancer treatment drug to the subject,
  (ii) a step of measuring a detected amount B of the expression product of the ASB4 gene in the subject after administering the candidate compound to the subject cell population, and
  (iii) a step of determining the candidate compound as a cancer treatment drug candidate that targets cancer stem cells when the detected amounts A and B are compared and the detected amount A is significantly larger than B.
[23] A polynucleotide encoding at least one of the antigen peptide according to any one of [1] to [12] or the polyepitope peptide according to [13].
[24] An expression vector comprising the polynucleotide according to [23].
[25] A gene transfer composition comprising the expression vector according to [24].
[26] A pharmaceutical composition comprising as an active ingredient any of (a) to (d) below:
  (a) the antigen peptide according to any one of [1] to [12] or the polyepitope peptide according to [13],
  (b) the polynucleotide according to [23],
  (c) the expression vector according to [24],
  (d) an ASB4 protein, an ASB4 protein-encoding polynucleotide, or an expression vector comprising the polynucleotide.
[27] The pharmaceutical composition according to [26] comprising as an active ingredient the antigen peptide according to any one of [1] to [12], and/or the polyepitope peptide according to [13].
[28] The pharmaceutical composition according to [26] or [27], further comprising an adjuvant.
[29] The pharmaceutical composition according to any one of [26] to [28], wherein the pharmaceutical composition is a preventive and/or therapeutic agent for cancer.
[30] The pharmaceutical composition according to any one of [26] to [29], wherein the pharmaceutical composition is a vaccine for the prevention and/or therapy of a cancer.
[31] An agent for inducing cytotoxic T cells, the agent comprising as an active ingredient any of (a) to (d) below:
  (a) the antigen peptide according to any one of [1] to [12] or the polyepitope peptide according to [13],
  (b) the polynucleotide according to [23],
  (c) the expression vector according to [24],
  (d) an ASB4 protein, an ASB4 protein-encoding polynucleotide, or an expression vector comprising the polynucleotide.
[32] A method for producing an antigen-presenting cell, the method comprising contacting in vitro a cell having an antigen-presenting ability with
  (A) the antigen peptide according to any one of [1] to [12] or the polyepitope peptide according to [13], or
  (B) a polynucleotide encoding at least one of the peptide and/or the polyepitope peptide of (A).
[33] A method for inducing a cytotoxic T cell, the method comprising contacting in vitro a peripheral blood lymphocyte with
  (A) the antigen peptide according to any one of [1] to [12] or the polyepitope peptide according to [13], or
  (B) a polynucleotide encoding at least one of the peptide and/or the polyepitope peptide of (A).
[34] An HLA multimer comprising an HLA and the antigen peptide according to any one of [1] to [12].

[35] A diagnostic agent comprising the HLA multimer according to [34].
[36] An antibody that recognizes the antigen peptide according to any one of [1] to [12].
[37] A T cell receptor-like antibody that recognizes a complex of an HLA and the antigen peptide according to any one of [1] to [12].
[38] A tumor-detecting agent comprising the antibody according to [36] and/or the T cell receptor-like antibody according to [37].
[39] A chimeric antigen receptor that recognizes a complex of an HLA and the antigen peptide according to any one of [1] to [12].
[40] An artificial CTL comprising a T cell receptor that recognizes a complex of an HLA and the antigen peptide according to any one of [1] to [12].
[41] A diagnostic agent for screening a patient to be treated for whom a method for the treatment of a cancer using the pharmaceutical composition according to any one of [26] to [30] is effective, the diagnostic agent comprising the cancer stem cell-detecting agent according to any one of [14] to [20], the HLA multimer according to [34], the antibody according to [36], and/or the T cell receptor-like antibody according to [37].
[42] An antigen peptide specific to cancer stem cells, comprising an amino acid sequence represented by any of SEQ ID Nos: 3 to 30.

Effects of the Invention

In accordance with the present invention, a tumor antigen peptide that is useful as an inducer for a CTL that specifically attacks a cancer stem cell, and a pharmaceutical composition, etc., comprising the above as an active ingredient, that is useful for the prevention and/or therapy of a cancer are provided.

BRIEF DESCRIPTION OF DRAWINGS

FIG. 2-1 shows the result of flow cytometry of cultures of single-cell isolated from a SW480-SP clone cell line and a SW480-MP clone cell line stained with Hoechst 33342/PI.
FIG. 2-2 shows a confocal microscopy image of the SW480-SP clone cell line and the SW480-MP clone cell line.
FIG. 4 shows the result of sequence analysis using mass spectrometry of a peptide isolated from a complex of an HLA and the peptide immunoprecipitated using an anti-HLA-A24 antibody from a lysate of the SW480-SP clone cell line and the SW480-MP clone cell line. The ASB4 sequence depicted is SEQ ID NO:2.
FIG. 5 shows a photograph of electrophoresis when mRNA of the SW480-SP and the SW480-MP is extracted and the gene expression is examined by RT-PCR. ASB4 gene was confirmed as a gene specific to the SW480-SP clone cell line.
FIG. 6 shows the result of RT-PCR for ASB4 using mRNA derived from human adult normal tissue.

MODES FOR CARRYING OUT THE INVENTION

Figure 1:
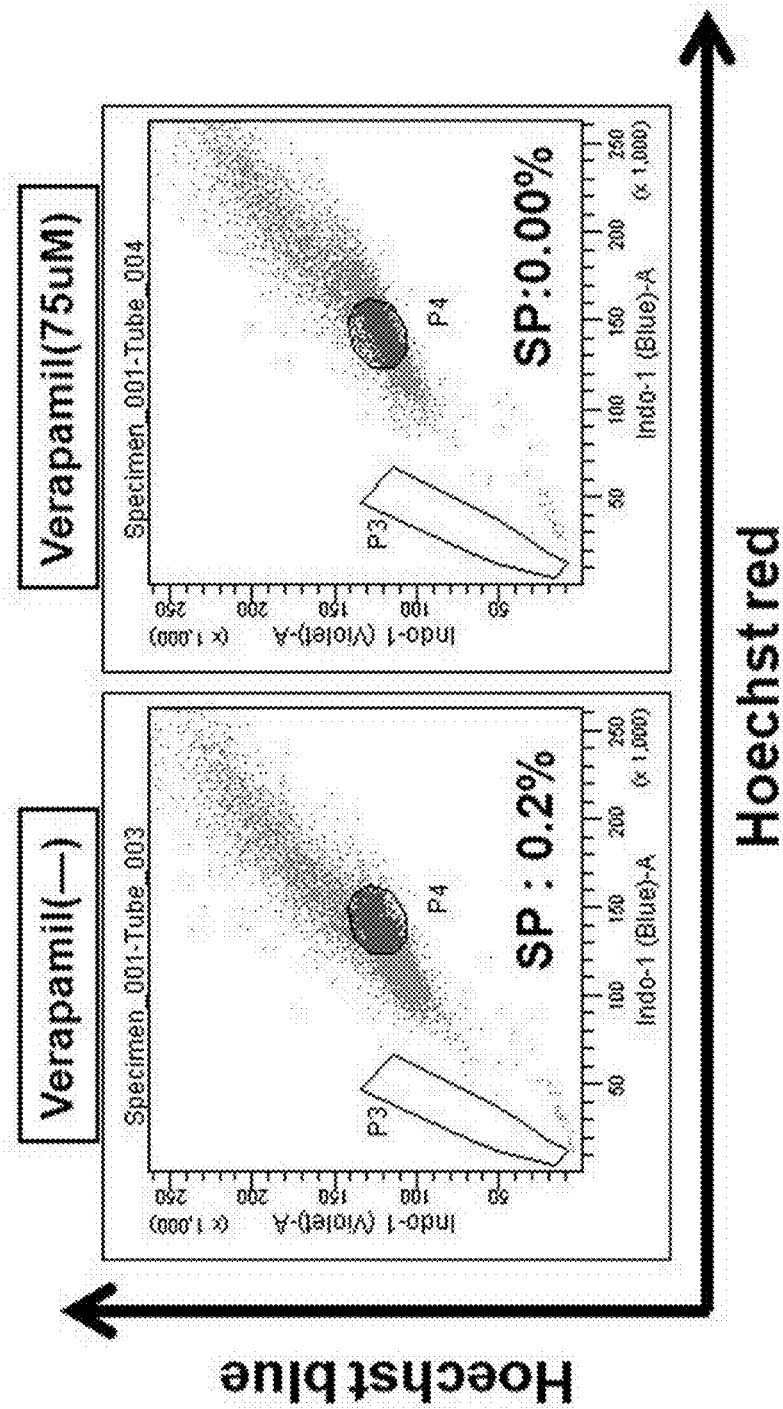
FIG. 1 shows the result of flow cytometry of a human colon cancer cell line (SW480) stained with Hoechst 33342/PI in the presence or absence of verapamil.

The present invention is explained in detail below.

The 'epitope peptide' referred to in the present invention means a peptide that binds to an MHC (an HLA for humans) and is subjected to antigen presentation on the cell surface and has antigenicity (can be recognized by a T cell). The epitope peptide includes a CTL epitope peptide that binds to an MHC class I, is subjected to antigen presentation, and is recognized by a CD8-positive T cell, and a helper epitope peptide that binds to an MHC class II, is subjected to antigen presentation, and is recognized by a CD4-positive T cell.

Among epitope peptides, a protein-derived peptide that is specifically or overexpressed in a tumor cell is in particular called a tumor antigen peptide. The antigen presentation referred to a phenomenon in which a peptide present within a cell binds to an MHC and this MHC/antigen peptide complex is localized on the cell surface. As described above, it is known that an antigen presented on a cell surface is recognized by a T cell, etc. and then activates cell-mediated immunity or humoral immunity; since an antigen presented by an MHC class I activates cell-mediated immunity and is also recognized by a T cell receptor of a naive T cell to thus induce the naive T cell to become a CTL having cytotoxic activity, a tumor antigen peptide used in immunotherapy is preferably a peptide that binds to an MHC class I and is subjected to antigen presentation.

In the present invention, a 'tumor' includes a benign tumor and a malignant tumor (cancer, malignant neoplasm). A cancer includes a hematopoietic tumor, an epithelial malignant tumor (carcinoma), and a nonepithelial malignant tumor (sarcoma). In the present invention, a 'cancer stem cell' means a cell, among cells present in cancerous tissue, that exhibits stem cell-like properties, and is a cell that is thought to be a causal cell involved in the occurrence, recurrence, and metastasis of a cancer. In general, since only a small amount of 'cancer stem cells' are present in cancerous tissue, it is difficult to distinguish them from other cells, but in the present technical field methods for isolating/concentrating cancer stem cells are known, examples thereof including an SP fractionation method. Therefore, in the present invention, a 'cancer stem cell' can mean a cell population that has been isolated/concentrated by a known cancer stem cell isolation/concentration method.

In the present invention, a natural peptide of the present invention has been isolated/identified using the following method for enabling isolation/identification of a natural peptide that is actually subjected to antigen presentation on a cell surface. In the present invention, a 'natural peptide' means a peptide that is actually subjected to antigen presentation on a cell surface. Furthermore, a 'natural antigen peptide' is a natural peptide that is confirmed to have antigenicity. By isolating this natural antigen peptide from a cancer cell and determining the sequence and the origin thereof, it is possible to obtain useful findings for the targeted therapy of a cancer using CTLs.

The method of isolating/identifying natural peptides used in the present invention comprises a step of lysing a cancer stem cell presenting a natural peptide and isolating a complex of an MHC and the natural peptide from the lysate, and a step of separating the isolated complex into the MHC molecule and the natural peptide to isolate the natural peptide, and a step of identifying the isolated natural peptide.

For the isolation of a complex of an MHC and the natural peptide, an extraction method of peptide/MHC complex by immunoprecipitation using a specific antibody against MHC was adopted. As the suitable anti-MHC antibodies, antibodies against HLA class I, such as anti-HLA-A02 antibody and anti-HLA-A24 antibody were used.

In the step of separating a complex into MHC molecules and natural peptides, peptide isolation using a weak acid was performed.

Furthermore, the sequence of the above isolated natural peptide was analyzed using a peptide sequence analysis method that combines liquid chromatography and tandem mass spectrometry, and the natural peptide that is actually subjected to antigen presentation on the cell surface was identified.

As a method for confirming antigenicity of the natural peptide isolated as described above, cytotoxicity test, ELISPOT assay, assay using TCR-like antibody, etc. were adopted.

The present inventors have analyzed a natural antigen peptide that is subjected to antigen presentation on a human cancer stem cell by the above method. As a result, an ASB4 protein-derived peptide (SEQ ID No: 3) has been identified as a natural antigen peptide that is subjected to antigen presentation on a cancer stem cell. As a result of further progressing research based on such a finding, it has been found that the ASB4 gene is highly expressed specifically in cancer stem cells and is a useful candidate gene for molecularly targeted therapy of cancer stem cells. The finding that ASB4 is a tumor antigen and, furthermore, the finding that an ASB4-derived peptide binds to an HLA class I antigen to form a complex on a tumor cell surface and is transported to the cell surface and subjected to antigen presentation are new findings that were hitherto completely unknown.

<1> the Peptide of the Present Invention

In the present invention, a 'human ASB4 protein' means a known protein reported in Mizuno Y, et al. Biochem Biophys Res Commun. 2002 Feb. 8; 290(5): 1499-505, and Yang C S, et al. Cell Rep. 2014 Jul. 24; 8(2): 327-37, and it specifically means a protein having an amino acid sequence described in SEQ ID No: 2 (Genbank Accession No: NP_057200; ASB4 isoform a) and an isoform and a homolog thereof. Examples of the isoform include a splicing variant and a variant such as an SNP based on individual difference. Specific examples include (1) a protein with an amino acid sequence that has a homology of at least 90%, preferably at least 95%, and more preferably at least 98% with the amino acid sequence represented by SEQ ID No: 2, and (2) a protein with an amino acid sequence for which one or more amino acids, preferably one to several, and more preferably 1 to 10, 1 to 5, 1 to 3, or 1 or 2 amino acids have been replaced, deleted, added, or inserted in the amino acid sequence described in SEQ ID No: 2. Examples of such a variant include an isoform (ASB4 isoform b) registered as Genbank Accession No.: NP_665879 which is a splicing variant of ASB4 isoform a, and SNPs such as dbSNP RefSNP No.: rs35047380 in which the 17th amino acid has been replaced from valine (V) to leucine (L). When simply 'ASB4 protein' is referred to in the present specification, it means a human ASB4 protein represented by the amino acid sequence described in SEQ ID No: 2, unless otherwise specified.

Preferred examples of the human ASB4 protein include a protein comprising the amino acid sequence described in SEQ ID No: 2, and a protein with an amino acid sequence for which 1 to 3, and preferably 1 or 2 amino acids have been replaced in said protein. A protein with the amino acid sequence described in SEQ ID No: 2 can be cited as a yet more preferred example.

In one embodiment, the peptide of the present invention includes a human ASB4 protein partial peptide, the peptide binding to an MHC, and in particular to an HLA; it is preferably a peptide that is subjected to antigen presentation by means of an MHC, in particular an HLA, and more preferably a peptide that is subjected to antigen presentation by means of an MHC, in particular an HLA, and can induce a CTL. There are several types of HLA; the peptide of the present invention preferably can bind to an HLA class I, more preferably can bind to HLA-A02 or HLA-A24, and yet more preferably can bind to both HLA-A02 and HLA-A24 (i.e., dual binding). The peptide of the present invention may be subjected to a treatment such as processing prior to binding to an MHC, and a peptide that forms an epitope peptide as a result of such a treatment is also included in the peptide of the present invention. Therefore, the amino acid length of the peptide of the present invention is not particularly limited as long as it is a sequence including an amino acid sequence of an epitope peptide. However, it is preferable that the peptide of the present invention itself is an epitope peptide, and therefore the amino acid length is preferably on the order of about 8 to 14 amino acids, more preferably on the order of about 8 to 11 amino acids, and particularly preferably on the order of about 9 to about 11 amino acids.

An epitope peptide that binds to an HLA class I, which is a human MHC class I, has a length of about 8 to 14 amino acids, and preferably a length of about 9 to 11 amino acids, and is known to have an HLA-specific binding motif in the sequence. For example, a peptide binding to HLA-A02 has a binding motif in which the second amino acid from the N terminal is leucine, isoleucine, or methionine and/or the amino acid at the C terminal is valine, leucine, or isoleucine, and a peptide binding to HLA-A24 has a binding motif in which the second amino acid from the N terminal is tyrosine, phenylalanine, methionine, or tryptophan and/or the amino acid at the C terminal is leucine, isoleucine, or phenylalanine.

Therefore, in a preferred embodiment, the peptide of the present invention includes an epitope peptide that is a partial peptide of the ASB4 protein with 8 to 14 consecutive amino acids in the amino acid sequence of said protein, the second amino acid from the N terminal being leucine, isoleucine, or methionine and/or the amino acid at the C terminal being valine, leucine, or isoleucine, and more preferably is the epitope peptide itself. Among them, an epitope peptide with an amino acid sequence represented by any of SEQ ID Nos: 4, 6, 7, 10, 14, 15, 17 to 19, to 23, 26, 28, 31, 33, 36, 39, 41, 42, 45 and 46 is particularly preferable.

Furthermore, in another preferred embodiment, the partial peptide includes an epitope peptide having the second amino acid from the N terminal replaced by leucine, isoleucine, or methionine and/or the amino acid at the C terminal replaced by valine, leucine, or isoleucine, and more preferably is the epitope peptide itself. Among them, an epitope peptide with an amino acid sequence represented by any of SEQ ID Nos: 4, 6, 7, 10, 14, 15, 17 to 19, 21 to 23, 26, 28, 31, 33, 36, 39, 41, 42, 45 and 46, the second amino acid from the N terminal being replaced by leucine, isoleucine, or methionine and/or the amino acid at the C terminal being replaced by valine, leucine, or isoleucine is particularly preferable.

In another preferred embodiment, the peptide of the present invention includes an epitope peptide that is a partial peptide of the ASB4 protein with 8 to 14 consecutive amino acids in the amino acid sequence of said protein, the second amino acid from the N terminal being tyrosine, phenylalanine, methionine, or tryptophan and/or the amino acid at the C terminal being leucine, isoleucine, or phenylalanine, and more preferably is the epitope peptide itself. Among them, an epitope peptide with an amino acid sequence represented by any of SEQ ID Nos: 9, 21, 25, 30, 32, 35 and 37 is particularly preferable.

Furthermore, in another preferred embodiment, the partial peptide includes an epitope peptide, the second amino acid from the N terminal being replaced by tyrosine, phenylalanine, methionine, or tryptophan and/or the amino acid at the C terminal being replaced by leucine, isoleucine, or phenylalanine, and more preferably is the epitope peptide itself. Among them, an epitope peptide with an amino acid sequence represented by any of SEQ ID Nos: 9, 21, 25, 30, 32, 35 and 37, the second amino acid from the N terminal being replaced by tyrosine, phenylalanine, methionine, or tryptophan and/or the amino acid at the C terminal being replaced by leucine, isoleucine, or phenylalanine is particularly preferable.

In another preferred embodiment, the peptide of the present invention is the partial peptide or the partial peptide that has been subjected to replacement, one to several amino acids being added to the N terminal and/or the C terminal.

Among them, a peptide with an amino acid sequence represented by any of SEQ ID Nos: 4, 6, 7, 10, 14, 15, 17 to 19, 21 to 23, 26, 28, 31, 33, 36, 39, 41, 42, 45 and 46, said peptide in which the second amino acid from the N terminal is replaced by leucine, isoleucine, or methionine and/or the amino acid at the C terminal is replaced by valine, leucine, or isoleucine, a peptide with an amino acid sequence represented by any of SEQ ID Nos: 9, 21, 25, 30, 32, 35 and 37, or said peptide in which the second amino acid from the N terminal is replaced by tyrosine, phenylalanine, methionine, or tryptophan and/or the amino acid at the C terminal is replaced by leucine, isoleucine, or phenylalanine and, furthermore, one to several amino acids are added to the N terminal and/or the C terminal is particularly preferable.

Therefore, in an embodiment, the peptide of the present invention may be represented by $Y_0\text{-}X_0\text{-}Z_0$, wherein all of $X_0$, $Y_0$, and $Z_0$ are peptides.

In such an embodiment, $X_0$ is a peptide selected from (1) to (4) below:

(1) a partial peptide of the ASB4 protein with 8 to 14 consecutive amino acids in the amino acid sequence of said protein, and preferably 8 to 11 amino acids, the second amino acid from the N terminal being leucine, isoleucine, or methionine and/or the amino acid at the C terminal being valine, leucine, or isoleucine;

(2) a peptide which, in the partial peptide defined in (1), the second amino acid from the N terminal being replaced by leucine, isoleucine, or methionine and/or the amino acid at the C terminal being replaced by valine, leucine, or isoleucine;

(3) a partial peptide of the ASB4 protein with 8 to 14 consecutive amino acids in the amino acid sequence of said protein, and preferably 8 to 11 amino acids, the second amino acid from the N terminal being tyrosine, phenylalanine, methionine, or tryptophan and/or the amino acid at the C terminal being leucine, isoleucine, or phenylalanine; or (4) a peptide which, in the partial peptide defined in (3), the second amino acid from the N terminal being replaced by tyrosine, phenylalanine, methionine, or tryptophan and/or the amino acid at the C terminal being replaced by leucine, isoleucine, or phenylalanine. Since (2) is a replacement homolog of (1), and (4) is a replacement homolog of (3), $Y_0\text{-}X_0\text{-}Z_0$ for which $X_0$ is a peptide of (2) or (4) is particularly called an '$X_0$ homolog'.

Furthermore, $Y_0$ and $Z_0$ are mutually independently any peptide with 0 to several amino acids. With this regard, '0 to several amino acids' specifically means 0 to 5 amino acids, examples including 0, 1, 2, 3, 4, or 5 amino acids, more preferably 0, 1, 2, or 3 amino acids, and particularly preferably 0 or 1 amino acids. In the present invention, when it is stated that $Y_0$ and/or $Z_0$ are 'not present', it means a case in which $Y_0$ and/or $Z_0$ are peptides with 0 amino acids.

The amino acids constituting $Y_0$ and/or $Z_0$ are not particularly limited; any of 20 types of natural amino acids constituting a protein can be cited, but preferable examples include an amino acid that is cleavable by an enzyme present in a living body. Furthermore, an amino acid sequence corresponding to an amino acid sequence on the N terminal side and/or on the C terminal side of the above partial peptide in the amino acid sequence of the ASB4 protein is desirable.

Therefore, among them, a case in which $X_0$ is either a peptide with an amino acid sequence represented by any of SEQ ID Nos: 4, 6, 7, 10, 14, 15, 17 to 19, 21 to 23, 26, 28, 31, 33, 36, 39, 41, 42, 45 and 46, said peptide in which the second amino acid from the N terminal is replaced by leucine, isoleucine, or methionine and/or the amino acid at the C terminal is replaced by valine, leucine, or isoleucine, a peptide with an amino acid sequence represented by any of SEQ ID Nos: 9, 21, 25, 30, 32, 35 and 37, or said peptide in which the second amino acid from the N terminal is replaced by tyrosine, phenylalanine, methionine, or tryptophan and/or the amino acid at the C terminal is replaced by leucine, isoleucine, or phenylalanine and, furthermore, $Y_0$ and/or $Z_0$ is one amino acid is particularly preferable, and a case in which either one of $Y_0$ or $Z_0$ is one amino acid and the other is not present is yet more preferable.

Furthermore, another preferred embodiment is a case in which $X_0$ is any of (1) to (4) with 8 to 11 amino acids and $Y_0$ and/or $Z_0$ are mutually independently a peptide with 0 to three amino acids, $Y_0\text{-}X_0\text{-}Z_0$ forming a partial peptide of the ASB4 protein having a length of 9 to 14 amino acids in its entirety or an $X_0$ homolog thereof. Examples of such an embodiment include, but are not limited to, a case in which $X_0$ is a peptide with an amino acid sequence represented by any of SEQ ID Nos: 3 to 7 and 9 to 19, 21 to 28, and 30 to 46, peptide $Y_0$ and/or $Z_0$ with 0 to 3 amino acids are added to the N terminal and/or C terminal of $X_0$, and such $Y_0\text{-}X_0\text{-}Z_0$ is also a partial peptide of the ASB4 protein.

With regard to the peptide of the present invention, in a preferred embodiment, $X_0$ includes a peptide with the same amino acid sequence as the amino acid sequence described in any of SEQ ID Nos: 3 to 7, 9 to 28 and 30. In this embodiment, it is more preferable that all of the peptides of the present invention (that is, $Y_0$-$X_0$-$Z_0$) are partial peptides of the ASB4 protein. In such a more preferred embodiment, examples of the peptide of the present invention include a peptide with the same amino acid sequence as the amino acid sequence described in any of SEQ ID Nos: 3 to 30.

The peptides represented by SEQ ID Nos: 3 to 30 are peptides with the 9 amino acids corresponding to amino acid positions 319 to 327 of the above ASB4 (SEQ ID No: 3), with the 9 amino acids corresponding to positions 80 to 88 (SEQ ID No: 4), with the 10 amino acids at positions 82 to 91 (SEQ ID No: 5), with the 10 amino acids at positions 124 to 133 (SEQ ID No: 6), with the 9 amino acids at positions 125 to 133 (SEQ ID No: 7), with the 12 amino acids at positions 184 to 195 (SEQ ID No: 8), with the 10 amino acids at positions 135 to 144 (SEQ ID No: 9), with the 10 amino acids at positions 83 to 92 (SEQ ID No: 10), with the 9 amino acids at positions 87 to 95 (SEQ ID No: 11), with the 10 amino acids at positions 307 to 316 (SEQ ID No: 12), with the 11 amino acids at positions 301 to 311 (SEQ ID No: 13) and with the 9 amino acids at positions 405 to 413 (SEQ ID No: 14), with the 10 amino acid at positions 35 to 44 (SEQ ID No: 15), with the 10 amino acid at positions 92 to 101 (SEQ ID No: 16), with the 9 amino acid at positions 152 to 160 (SEQ ID No: 17), with the 10 amino acid at positions 186 to 195 (SEQ ID No: 18), with the 10 amino acids at positions 236 to 245 (SEQ ID No: 19), with the 10 amino acids at positions 265 to 274 (SEQ ID No: 20), with the 10 amino acids at positions 280 to 289 (SEQ ID No: 21), with the 10 amino acids at positions 383 to 392 (SEQ ID No: 22), with the 10 amino acids at positions 416 to 425 (SEQ ID No: 23), with the 10 amino acids at positions 76 to 85 (SEQ ID No: 24), with the 10 amino acids at positions 192 to 201 (SEQ ID No: 25), with the 10 amino acids at positions 211 to 220 (SEQ ID No: 26), with the 10 amino acids at positions 289 to 298 (SEQ ID No: 27), with the 10 amino acids at positions 318 to 327 (SEQ ID No: 28), with the 12 amino acids at positions 365 to 376 (SEQ ID No: 29), with the 9 amino acids at positions 365 to 373 (SEQ ID No: 30), respectively, and the present inventors have found that all of the peptides being capable of binding to HLA-A02 and/or HLA-A24. In particular the present inventors have found that the peptides represented by SEQ ID Nos: 3 to 23, 25, 26 and 28 to 30 also have CTL inducibility.

In a yet more preferred embodiment, $X_0$ includes a peptide with the same amino acid sequence as the amino acid sequence described in any of SEQ ID Nos: 4 to 7, 9 to 12 and 15 to 19 and 21 to 23. In this embodiment, it is more preferable that all of the peptides of the present invention (that is, $Y_0$-$X_0$-$Z_0$) are partial peptides of the ASB4 protein. In such a more preferred embodiment, examples of the peptide of the present invention include a peptide with the same amino acid sequence as the amino acid sequence described in any of SEQ ID Nos: 4 to 12 and 15 to 23.

The present inventors have found that all of the peptides represented by SEQ ID Nos: 4 to 12 and 15 to 23 being capable of binding to HLA-A02 and having CTL inducibility.

In another yet more preferred embodiment, $X_0$ includes a peptide with the same amino acid sequence as the amino acid sequence described in any of SEQ ID Nos: 3 to 7, 9, 13, 14, 18, 24 to 28 and 30. In this embodiment, it is more preferable that all of the peptides of the present invention (that is, $Y_0$-$X_0$-$Z_0$) are partial peptides of the ASB4 protein. In such a more preferred embodiment, examples of the peptide of the present invention include a peptide with the same amino acid sequence as the amino acid sequence described in any of SEQ ID Nos: 3 to 9, 13, 14, 25, 26 and 28 to 30.

The present inventors have found that all of the peptides represented by any of SEQ ID Nos: 3 to 9, 13, 14, 25, 26 and 28 to 30 being capable of binding to HLA-A024 and having CTL inducibility.

In another yet more preferred embodiment, $X_0$ includes a peptide with the same amino acid sequence as the amino acid sequence described in any of SEQ ID Nos: 4 to 7, 9 and 18. In this embodiment, it is more preferable that all of the peptides of the present invention (that is, $Y_0$-$X_0$-$Z_0$) are partial peptides of the ASB4 protein. In such a more preferred embodiment, examples of the peptide of the present invention include a peptide with the same amino acid sequence as the amino acid sequence described in any of SEQ ID Nos: 4 to 9.

The present inventors have found that all of the peptides represented by any of SEQ ID Nos: 4 to 9 being capable of binding to both HLA-A02 and HLA-A24, and having CTL inducibility. Among them, the peptides represented by SEQ ID Nos: 4 to 6, 8 and 9 are particularly preferable, and the peptides represented by SEQ ID Nos: 5 and 8 are most preferable.

The peptide of the present invention may have its N terminal and/or C terminal modified. Specific examples of the modification include N-alkanoylation (for example, acetylation), N-alkylation (for example, methylation), a C-terminal alkyl ester (for example, an ethyl ester), and a C-terminal amide (for example a carboxamide).

Synthesis of the peptide of the present invention may be carried out in accordance with known methods used in normal peptide chemistry. Such known methods includes methods described in the literature (Peptide Synthesis, Interscience, New York, 1966; The Proteins, Vol. 2, Academic Press Inc., New York, 1976; Peptide Synthesis, Maruzen Co., Ltd., 1975; Basics and Experiments of Peptide Synthesis, Maruzen Co., Ltd., 1985; Development of Pharmaceuticals Seq. Vol. 14 Peptide Synthesis, Hirokawa Shoten Co., 1991, these publications forming part of the present application by reference), etc.

With regard to the peptide of the present invention, in vivo activity can be confirmed by subjecting it to a CTL induction method, which is described later, an assay using an animal model for human (WO02/47474, Int J. Cancer: 100, 565-570 (2002)), etc.

In another embodiment, the peptide of the present invention includes a peptide that binds to HLA-A02 and/or HLA-A24. Specifically, examples include, but are not limited to, a peptide with the amino acid sequence represented by any of SEQ ID Nos: 3 to 30. These peptides are not necessarily those having a binding motif of HLA-A02 or HLA-A24, but they are the peptides actually confirmed to bind to HLA-A02 and/or HLA-A24 by the present inventors. Among them, a peptide with the amino acid sequence represented by any of SEQ ID Nos: 3 to 23, 25, 26 and 28 to 30 has been confirmed to have CTL inducibility as well, which is preferable.

The peptide of the present invention further includes a peptide in which a plurality of epitope peptides including at least one of the peptides of the present invention are linked (polyepitope peptide). Therefore, specific examples of the peptide of the present invention include a peptide that is the above polyepitope peptide and has CTL-inducing activity.

The polyepitope peptide of the present invention may specifically be defined as (i) a peptide in which the peptide of the present invention (epitope peptide) and any one or more CTL epitope peptides other than the peptide of the present invention are linked directly or via a spacer as appropriate,
(ii) a peptide in which the peptide of the present invention and any one or more helper epitope peptides are linked directly or via a spacer as appropriate, or
(iii) a peptide in which a polyepitope peptide described in (i) above and further one or more helper epitope peptides are linked directly or via a spacer as appropriate,
the peptide being subjected to processing within an antigen-presenting cell, and the epitope peptide thus formed being presented on the antigen-presenting cell, thus leading to CTL-inducing activity.

The CTL epitope peptide other than the peptide of the present invention in (i) is not particularly limited; specific examples include another human ASB4-derived epitope peptide that is not included in the present invention and a human OR7C1- or human DNAJB8-derived epitope peptide (for example, a peptide described in WO2010/050190), and a human FAM83B-derived epitope peptide (International Patent Application PCT/JP2014/076625), etc.

The spacer is not particularly limited as long as it does not adversely affect processing within an antigen-presenting cell, and is preferably a linker that is linked to each epitope peptide via a peptide bond, examples including a peptide linker in which several amino acids are linked and a linker having an amino group and a carboxyl group at each end. Specific examples include a glycine linker or a PEG (polyethylene glycol) linker; examples of the glycine linker include polyglycine (for example a peptide consisting of six glycines; Cancer Sci, Vol. 103, p. 150-153), and examples of the PEG linker include a linker derived from a compound having an amino group and a carboxy group at each end of PEG (for example, $H_2N—(CH_2)_2—(OCH_2CH_2)_3—COOH$; Angew. Chem. Int. Ed. 2008, 47, 7551-7556).

With regard to the epitope peptide of the present invention contained in the polyepitope peptide of the present invention, one or more types may be selected. That is, a plurality of identical epitope peptides may be linked, or a plurality of different epitope peptides may be linked. Naturally, even when two or more types of epitope peptides are selected, a plurality of one or more types of selected epitope peptides may be linked. Similarly, with regard to the epitope peptide other than the peptide of the present invention, a plurality of types and/or a plurality of epitope peptides may be linked. The polyepitope peptide of the present invention may be one in which 2 to 12 epitope peptides are linked, is preferably one in which 2, 3, 4, 5, 6, 7, 8, 9, 10, 11, or 12 epitope peptides are linked, and is most preferably one in which 2 epitope peptides are linked.

When the epitope peptide that is linked to the peptide of the present invention is a helper epitope peptide, examples of the helper epitope peptide used include hepatitis B virus-derived HBVc128-140 and tetanus toxin-derived TT947-967. The length of the helper epitope peptide is on the order of 13 to 30 amino acids, and preferably on the order of 13 to 17 amino acids.

Such a peptide in which a plurality of epitope peptides are linked (polyepitope peptide) may also be produced by a standard peptide synthesis method as described above. Furthermore, based on information regarding the sequence of a polynucleotide encoding such a polyepitope peptide in which a plurality of epitope peptides are linked, it may be produced using standard DNA synthesis and genetic engineering methods.

That is, said polynucleotide is inserted into a known expression vector, a host cell is transformed by means of the recombinant expression vector thus obtained to give a transformant, the transformant is cultured, and the target polyepitope peptide in which a plurality of epitopes are linked can be produced by recovery from the culture. These methods may be carried out in accordance with methods described in the literature as described above (Molecular Cloning, T. Maniatis et al., CSH Laboratory (1983), DNA Cloning, D M. Glover, IRL PRESS (1985)).

The polyepitope peptide thus produced in which a plurality of epitope peptides are linked is subjected to the above in vitro assay or an in vivo assay using an animal model for human described in WO02/47474 and Int J. Cancer: 100, 565-570 (2002) (these publications forming part of the present application by reference), etc., thus enabling CTL-inducing activity to be confirmed.

The peptide of the present invention (including the polyepitope peptide) is useful for the prevention and/or therapy of a cancer, etc. as described in the present specification, and may be an active ingredient of a pharmaceutical composition. Furthermore, the peptide of the present invention may be for the prevention and/or therapy of a cancer. Moreover, the present invention also relates to use of the peptide of the present invention in the production of a medicament for the prevention and/or therapy of a cancer.

<2> Polynucleotide of the Present Invention

The polynucleotide of the present invention includes a polynucleotide that encodes at least one of the peptides of the present invention. The polynucleotide of the present invention may be any of cDNA, mRNA, cRNA, or synthetic DNA. It may have either a single strand or a double strand configuration. Specific examples include, but are not limited to, a polynucleotide with a nucleotide sequence encoding an amino acid sequence predicted using a binding prediction program of MHC and peptide, such as BIMAS bimas.cit-.nih.gov/molbio/hla_bind/), SYFPEITHI (syfpeithi.de/) and IEDB (MHC-I processing predictions; iedb.org/); and more specifically, they include a polynucleotide with a nucleotide sequence encoding an amino acid sequence described in SEQ ID Nos: 3-46, and a polynucleotide with a nucleotide sequence encoding so that it can express a polyepitope peptide in which any two or more peptides selected from SEQ ID Nos: 3-46 are linked or a peptide selected from SEQ ID Nos: 3-46 and a helper epitope peptide are linked.

The polynucleotide of the present invention may take on either a single strand or a double strand configuration. When the polynucleotide of the present invention is a double strand, a recombinant expression vector expressing the peptide of the present invention may be produced by inserting the polynucleotide of the present invention into an expression vector. That is, the scope of the polynucleotide of the present invention includes a recombinant expression vector produced by inserting the double strand polynucleotide of the present invention into an expression vector.

The polynucleotide of the present invention is useful for the prevention and/or therapy of a cancer, etc. as described in the present specification, and may be an active ingredient of a pharmaceutical composition. Furthermore, the polynucleotide of the present invention may be for the prevention and/or therapy of a cancer. Moreover, the present invention also relates to use of the polynucleotide of the present invention in the production of a medicament for the prevention and/or therapy of a cancer.

With regard to the expression vector used in the present invention, various types may be used according to the host used, the intended application, etc., and a person skilled in the art may select it as appropriate. Examples of expression vectors that can be used in the present invention include a plasmid, a phage vector, and a virus vector. For example, when the host is *Escherichia coli*, examples of the vector include plasmid vectors such as pUC118, pUC119, pBR322, and pCR3 and phage vectors such as λZAPII and λgt11. When the host is a yeast, examples of the vector include pYES2 and pYEUra3. When the host is an insect cell, examples include pAcSGHisNT-A. When the host is an animal cell, examples include plasmid vectors such as pCEP4, pKCR, pCDM8, pGL2, pcDNA3.1, pRc/RSV, and pRc/CMV and virus vectors such as a retrovirus vector, an adenovirus vector, and an adeno-associated virus vector.

The vector may have as appropriate a factor such as a promoter capable of inducing expression, a gene encoding a signal sequence, a selection marker gene, or a terminator. Furthermore, in order to make isolation and purification easy, a sequence for expression as a fusion protein with thioredoxin, a His tag, GST (glutathione S-transferase), etc. may be added. In this case, a GST fusion protein vector (pGEX4T, etc.) having an appropriate promoter (lac, tac, trc, trp, CMV, SV40 early promoter, etc.) that functions within a host cell, a vector having a tag sequence such as Myc or His (pcDNA3.1/Myc-His, etc.) and, furthermore, a vector expressing a fusion protein with thioredoxin and a His tag (pET32a), etc. may be used.

Transforming a host with the expression vector prepared as above enables a transformed cell containing the expression vector to be prepared. Therefore, the present invention includes a gene transfer composition including the expression vector.

The host used for transformation may be any cell as long as the function of the polypeptide of the present invention is not impaired, and examples include an *Escherichia coli*, a yeast, an insect cell, and an animal cell. Examples of the *Escherichia coli* include *E. coli* K-12 strain HB101, C600, JM109, DH5α, and AD494 (DE3). Examples of the yeast include *Saccharomyces cerevisiae*. Examples of the animal cell include L929 cells, BALB/c3T3 cells, C127 cells, CHO cells, COS cells, Vero cells, HeLa cells, and 293-EBNA cells. Examples of the insect cell include sf9.

As a method for introducing an expression vector into a host cell, a standard introduction method suitable for the host cell may be used. Specific examples include a calcium phosphate method, a DEAE-dextran method, an electroporation method, and a method using a lipid for gene transfer (Lipofectamine, Lipofectin; Gibco-BRL). After introduction, culturing is carried out in a standard medium containing a selection marker, thus enabling a transformed cell in which the expression vector has been introduced into the host cell to be selected.

Continuing culturing the transformed cell thus obtained under suitable conditions enables the peptide of the present invention to be produced. The peptide thus obtained may be further isolated and purified by usual biochemical purification means. Examples of purification means include salting out, ion-exchange chromatography, adsorption chromatography, affinity chromatography, and gel filtration chromatography. When the peptide of the present invention is expressed as a fusion protein with a thioredoxin, a His tag, a GST, etc. as described above, isolation and purification may be carried out by a purification method utilizing the properties of the fusion protein or the tag.

The polynucleotide encoding the peptide of the present invention may have a DNA configuration or an RNA configuration. These polynucleotides of the present invention may be easily produced by standard methods known in the present technical field based on amino acid sequence information of the peptide of the present invention and DNA sequence information encoded thereby. Specifically, it may be produced by standard DNA synthesis, amplification by means of PCR, etc.

The polynucleotide encoding the peptide of the present invention includes a polynucleotide encoding the epitope peptide.

<3> CTL Inducer/Pharmaceutical Composition Comprising a Peptide of the Present Invention as Active Ingredient The peptide of the present invention has CTL-inducing activity and can be a CTL inducer as a tumor antigen peptide. Furthermore, as described above, the present inventors have found for the first time that the ASB4 protein is a tumor antigen and an ASB4 protein-derived peptide binds to an HLA class I antigen, forms a complex on the tumor cell surface, is transported to the cell surface, and is subjected to antigen presentation. Therefore, the ASB4 protein itself can become a CTL inducer.

That is, peripheral blood lymphocytes are isolated from a person who is positive for an HLA-A02 antigen or an HLA-A24 antigen, they are stimulated in vitro by adding the peptide of the present invention and/or ASB4 protein, and CTLs that specifically recognize an HLA-A02 antigen-positive cell or an HLA-A24 antigen-positive cell that have been pulsed with the peptide can be induced (J. Immunol., 154, p. 2257, 1995). The presence or absence of CTL induction may be confirmed by measuring for example the amount of various cytokines (for example IFN-γ) produced by CTLs when reacting with an antigen peptide-presenting cell, by means of for example an ELISA method, etc. It may also be confirmed by a method for measuring CTL toxicity toward an antigen peptide-presenting cell labeled with $^{51}$Cr ($^{51}$Cr release assay, Int. J. Cancer, 58: p 317, 1994).

Furthermore, a CTL clone may be established by a method described in Int. J. Cancer, 39, 390-396, 1987, N. Eng. J. Med, 333, 1038-1044, 1995, etc.

A CTL induced by the peptide and/or ASB4 protein of the present invention has a cytotoxic action toward a cell presenting the peptide of the present invention and/or another ASB4 protein-derived epitope peptide as an antigen and the ability to produce a lymphokine. Since the peptide of the present invention is a tumor antigen peptide as described above, and the ASB4 protein is decomposed within a cell to thus form a tumor antigen peptide, it can exhibit an anti-tumor action, and preferably an anti-cancer action, via the above functions. Therefore, the peptide and/or ASB4 protein of the present invention and a CTL induced thereby can be an active ingredient of a medicament or a pharmaceutical composition for the prevention and/or therapy of a cancer.

When a CTL inducer containing the peptide and/or ASB4 protein of the present invention as an active ingredient is administered to a cancer patient, the peptide of the present invention and/or the ASB4 protein-derived epitope peptide is presented on an HLA-A02 antigen or HLA-A24 antigen of an antigen-presenting cell, a CTL that is specific to a complex of the HLA-A02 antigen or HLA-A24 antigen and the presented peptide proliferates and destroys the cancer cells, and as a result, the cancer can be prevented and/or treated. Therefore, a CTL inducer containing the peptide and/or ASB4 protein of the present invention as an active ingredient can preferably be used for a subject who is positive for an HLA-A02 antigen or HLA-A24 antigen and who has an ASB4-positive cancer. Examples of ASB4-positive cancers include cancers (tumors) such as colon cancer, lung cancer, breast cancer, oral cancer, cervical cancer, thyroid cancer, testicular tumor, and ovarian cancer, and the CTL inducer of the present invention may be used for the prevention and/or therapy of such cancers.

The 'prevention' of a cancer includes not only preventing a patient from having a cancer but also prevention of recurrence in a patient who has been subjected to surgery to remove a primary tumor and prevention of metastasis of a tumor that could not be completely removed by a cancer treatment such as surgery, radiotherapy, drug therapy, etc. Furthermore, the 'treatment' of a cancer includes not only curing and improvement of the symptoms of a cancer that reduces the size of the cancer but also prevention of cancer cell proliferation or tumor enlargement, or suppression of metastasis of cancer cells from a primary focus.

A CTL inducer containing the peptide and/or ASB4 protein of the present invention as an active ingredient is for example particularly effective for an HLA-A02- or HLA-A24-positive cancer patient who has a cancer positive for the ASB4 described in SEQ ID No: 2. Specifically, it may be used for the prevention or therapy of a cancer (tumor) such as for example colon cancer, lung cancer, or ovarian cancer. Therefore, a pharmaceutical composition containing the peptide of the present invention and/or the ASB4 protein as an active ingredient is also included in the present invention. Such a pharmaceutical composition is preferably a composition for the prevention and/or therapy of a cancer, that is, a preventive and/or therapeutic agent for cancer. Furthermore, since the pharmaceutical composition of the present invention prevents and/or treats a cancer by inducing a CTL that is specific to a cancer cell (preferably a cancer stem cell), that is, activating cell-mediated immunity that is specific to a cancer cell, it is preferably a vaccine for the prevention and/or therapy of a cancer.

A pharmaceutical composition containing the peptide of the present invention as an active ingredient may be one that contains a single CTL epitope (the peptide of the present invention) as an active ingredient or one that contains as an active ingredient a polyepitope peptide having another peptide (CTL epitope or helper epitope) linked thereto. In recent years, it has been shown that a polyepitope peptide having a plurality of linked CTL epitopes (antigen peptides) has activity in efficiently inducing CTLs in vivo. For example, Journal of Immunology 1998, 161: 3186-3194 (this publication forms part of the present application by reference) describes the induction in vivo of a CTL that is specific to each CTL epitope by means of an approximately 30 mer polyepitope peptide in which cancer antigen protein PSA-derived HLA-A2, -A3, -A11, and -B53-restricted CTL epitopes (antigen peptides) are linked. It is also shown that a polyepitope peptide in which a CTL epitope and a helper epitope are linked efficiently induces a CTL. When administered in the configuration of such a polyepitope peptide, the polyepitope peptide is incorporated into an antigen-presenting cell, and after that, individual antigen peptides that have been formed by intracellular degradation bind to an HLA antigen to thus form a complex, this complex is presented on the antigen-presenting cell surface at high density, a CTL specific to this complex proliferates efficiently in the body, and cancer cells are destroyed. In this way, the treatment or prevention of a cancer is promoted.

A pharmaceutical composition containing the peptide and/or ASB4 protein of the present invention as an active ingredient may be administered as a mixture with a pharmaceutically acceptable carrier, for example an appropriate adjuvant, or in combination therewith, so as to establish cell-mediated immunity effectively.

As the adjuvant, an adjuvant known in the present technical field such as one described in the literature (for example, Clin Infect Dis.: S266-70, 2000) may be applied, and specific examples include a gel type such as aluminum hydroxide, aluminum phosphate, or calcium phosphate, a bacterial type such as CpG, monophosphoryl lipid A (monophosphoryl lipid A; MPL), cholera toxin, *Escherichia coli* heat-labile toxin, pertussis toxin, or muramyl dipeptide (Muramyl dipeptide; MDP), an oil emulsion type (emulsion preparation) such as Freund's incomplete adjuvant, MF59, or SAF, a macromolecular nanoparticle type such as an immunostimulatory complex (Immunostimulatory complex; ISCOMs), a liposome, biodegradable microspheres (Biodegradable microsphere), or saponin-derived QS-21, a synthetic type such as a nonionic block copolymer, a muramyl peptide analog (Muramyl peptide analogue), a polyphosphazene, or a synthetic polynucleotide, and a cytokine type such as IFN-γ, IL-2, or IL-12.

Furthermore, the dosage form of a CTL inducer/pharmaceutical composition containing the peptide and/or ASB4 protein of the present invention as an active ingredient is not particularly limited, and examples include an oil emulsion (emulsion formulation), macromolecular nanoparticles, a liposome formulation, a particulate formulation bonded to beads having a diameter of a few μm, a lipid-bonded formulation, a microsphere formulation, and a microcapsule formulation.

Examples of an administration method include any known administration method such as intradermal administration, subcutaneous administration, intramuscular administration, or intravenous administration. The dose of the peptide of the present invention in a preparation may be adjusted as appropriate according to the target disease to be treated, the age and body weight of the patient, etc., but it is usually 0.0001 mg to 1000 mg, preferably 0.001 mg to 1000 mg, and more preferably 0.1 mg to 10 mg, this being preferably administered once in a few days to a few months.

As a method for making the peptide of the present invention actually act as a medicament, there is an in vivo method in which the peptide is directly introduced into the body as well as an ex vivo method in which a specific type of cells are collected from a person, the peptide of the present invention is made to act thereon in vitro, and the cells are returned into the body (Nikkei Science, April, 1994, pp. 20-45, Gekkan Yakuji, 36 (1), 23-48 (1994), Experimental Medicine Special Edition, 12 (15), (1994), references quoted therein, etc., these publications forming part of the present application by reference), and a person skilled in the art can select a cell, an administration method, an administration configuration, and a dose appropriate for such a method.

<4> CTL Inducer/Pharmaceutical Composition Containing the Polynucleotide of the Present Invention as Active Ingredient Since a cell in which the polynucleotide and/or ASB4 protein-encoding polynucleotide of the present invention is expressed becomes a cell that presents the peptide of the present invention and/or another ASB4 protein-derived epitope peptide as an antigen, it has the feature that it is recognized by a T cell via a T cell receptor. Therefore, the polynucleotide and/or ASB4 protein-encoding polynucleotide of the present invention can also become a CTL inducer. An induced CTL can exhibit, in the same way as for a CTL induced by the peptide and/or ASB4 protein of the present invention, an anti-tumor action via a cytotoxic action or the production of a lymphokine, and preferably an anti-cancer action. Therefore, the polynucleotide and/or ASB4 protein-encoding polynucleotide of the present invention can be an active ingredient of a medicament or a pharmaceutical composition for the therapy or prevention of a cancer. A CTL inducer containing the polynucleotide and/or ASB4 protein-encoding polynucleotide of the present invention as an active ingredient can treat and/or prevent a cancer by for example administering the polynucleotide and/or ASB4 protein-encoding polynucleotide of the present invention to a cancer patient and expressing them in the cancer patient.

For example, when the polynucleotide and/or ASB4 protein-encoding polynucleotide of the present invention incorporated into an expression vector is administered to a cancer patient by the method below, a tumor antigen peptide is highly expressed within antigen-presenting cells. The tumor antigen peptide thus produced subsequently binds to an HLA-A02 antigen or an HLA-A24 antigen to form a complex, this complex is presented at high density on the antigen-presenting cell surface, cancer-specific CTLs proliferate efficiently in the body, and the cancer cells are destroyed. As described above, the therapy or prevention of a cancer is achieved. Therefore, a pharmaceutical composition containing the polynucleotide and/or ASB4 protein-encoding polynucleotide of the present invention is also included in the present invention. Such a pharmaceutical composition is preferably a composition for the prevention and/or therapy of a cancer, that is, a preventive and/or therapeutic agent for cancer. Furthermore, since the pharmaceutical composition of the present invention prevents and/or treats a cancer by inducing a CTL that is specific to a cancer cell (preferably a cancer stem cell), that is, activating cell-mediated immunity that is specific to a cancer cell, it is preferably a vaccine for the prevention and/or therapy of a cancer.

The CTL inducer/pharmaceutical composition containing the polynucleotide of the present invention as an active ingredient may preferably be used for an HLA-A02 antigen- or HLA-A24 antigen-positive subject who has an ASB4-positive cancer. Examples of the ASB4-positive cancer include cancers (tumors) such as colon cancer, lung cancer, breast cancer, oral cancer, cervical cancer, thyroid cancer, testicular tumor, and ovarian cancer, and the CTL inducer of the present invention may be used for the prevention or therapy of these cancers.

As a method for administering the polynucleotide and/or ASB4 protein-encoding polynucleotide of the present invention and incorporating it into a cell, any method such as a method involving a virus vector and other methods (Nikkei Science, 1994, April, pp. 20-45, Gekkan Yakuji, 36 (1), 23-48 (1994), Experimental Medicine Special Edition, 12 (15), (1994), references quoted therein, etc., these publications forming part of the present application by reference) may be employed. Therefore, in an embodiment of the pharmaceutical composition of the present invention, a vector containing the polynucleotide and/or the ASB4 protein-encoding polynucleotide of the present invention is contained as an active ingredient.

Examples of a method involving a virus vector include a method in which the DNA of the present invention is integrated into for example a DNA virus or RNA virus such as a retrovirus, adenovirus, adeno-associated virus, herpes virus, vaccinia virus, poxvirus, poliovirus, or sindbis virus, and incorporation is carried out. Among them, a method involving a retrovirus, adenovirus, adeno-associated virus, vaccinia virus, etc. is particularly preferable.

Examples of other methods include a method in which an expression plasmid is directly administered intramuscularly (DNA vaccine method), a liposome method, a lipofectin method, a microinjection method, a calcium phosphate method, and an electroporation method; and a DNA vaccine method and a liposome method are particularly preferable.

In order to make the polynucleotide and/or ASB4 protein-encoding polynucleotide of the present invention actually act as a medicament, there are an in vivo method in which the polynucleotide is directly introduced into the body and an ex vivo method in which a specific type of cells are collected from a person, the polynucleotide of the present invention is incorporated into the cells in vitro, and the cells are returned into the body (Nikkei Science, 1994, April, pp. 20-45, Gekkan Yakuji, 36 (1), 23-48 (1994), Experimental Medicine Special Edition, 12 (15), (1994), references quoted therein, etc., these publications forming part of the present application by reference). An in vivo method is more preferable.

When the polynucleotide and/or ASB4 protein-encoding polynucleotide of the present invention is administered by an in vivo method, administration may be carried out by selecting as appropriate an administration route and an administration form according to the target disease to be treated, the symptoms, etc. For example, administration may be carried out in a form that can be injected into a vein, an artery, subcutaneously, intradermally, intramuscularly, etc. When administration is carried out by an in vivo method, for example, a formulation form such as a liquid may be employed, but it is usually made into an injection, etc. containing the polynucleotide of the present invention, which is an active ingredient, and a pharmaceutically acceptable carrier (carrier) may be added as necessary. With regard to a liposome or a membrane fusion liposome (Sendai virus (HVJ)-liposome, etc.) containing the polynucleotide of the present invention, a liposome preparation such as a suspension, a frozen agent, or a centrifugation-concentrated frozen agent may be employed.

The content of the polynucleotide of the present invention in a formulation may be adjusted as appropriate according to the target disease to be treated, the age and body weight of the patient, etc.; it is usually 0.0001 mg to 100 mg as a polynucleotide content, and preferably 0.001 mg to 10 mg of the polynucleotide of the present invention, it preferably being administered once in a few days to a few months.

A person skilled in the art can appropriately select a suitable cell, vector, administration method, administration form, and dose.

Furthermore, in recent years, it has been shown that a polynucleotide encoding a polyepitope peptide having a plurality of linked CTL epitopes (tumor antigen peptides) and a polynucleotide encoding a polyepitope peptide having a CTL epitope and a helper epitope that are linked have activity in efficiently inducing CTLs in vivo. For example, Journal of Immunology 1999, 162: 3915-3925 (this publication forms part of the present application by reference) reports that DNA encoding an epitope peptide (minigene) having six types of HBV-derived HLA-A2-restricted antigen peptides, three types of HLA-A11-restricted antigen peptides, and a helper epitope that are linked has induced CTLs for each epitope in vivo effectively. Therefore, a CTL inducer active ingredient can be made by incorporating into an appropriate expression vector a polynucleotide prepared by linking one or more types of polynucleotide encoding the peptide of the present invention, and in some cases also linking a polynucleotide encoding another peptide. Such a CTL inducer can also employ the same administration method and administration form as described above.

<5> Antigen-Presenting Cell of the Present Invention

The peptide and polynucleotide of the present invention described above may be utilized for example in vitro as follows. That is, either of the peptide and polynucleotide of the present invention and cells having antigen-presenting ability are brought into contact with each other in vitro, thus enabling antigen-presenting cells to be prepared. Therefore, one embodiment of the present invention provides an antigen-presenting cell that presents on the cell surface a complex of an HLA-A02 antigen or an HLA-A24 antigen and the peptide of the present invention, and a method for producing same. As described above, the peptide and polynucleotide of the present invention can be utilized for the prevention and/or therapy of a cancer. Therefore, the antigen-presenting cell or the production method therefor of the present embodiment preferably utilizes an isolated cell that is derived from a cancer patient. Specifically, an antigen-presenting cell presenting a complex of an HLA-A02 antigen or an HLA-A24 antigen and the peptide of the present invention on the cell surface of a cancer patient-derived isolated cell having antigen-presenting ability is produced by bringing the cell into contact with either the peptide or the polynucleotide of the present invention in vitro.

The 'cell having antigen-presenting ability' is not particularly limited as long as it is a cell expressing on the cell surface an MHC, preferably an HLA, and more preferably an HLA-A02 antigen or an HLA-A24 antigen, that can present the peptide of the present invention, and among them it is preferably a professional antigen-presenting cell, and particularly preferably a dendritic cell, which is considered to have high antigen-presenting ability.

Furthermore, with regard to a substance that is added in order to prepare the antigen-presenting cell of the present invention from the cell having an antigen-presenting ability, it may be either the peptide or the polynucleotide of the present invention.

The antigen-presenting cell of the present invention is obtained by for example isolating cells having antigen-presenting ability from a cancer patient, and pulsing the cells with the peptide of the present invention in vitro so as to make them present a complex of an HLA-A02 antigen or an HLA-A24 antigen and the peptide of the present invention (Cancer Immunol. Immunother., 46: 82, 1998, J. Immunol., 158, p. 1796, 1997, Cancer Res., 59, p. 1184, 1999). When dendritic cells are used, for example, lymphocytes are separated from the peripheral blood of a cancer patient by the Ficoll method, non-adherent cells are then removed, adherent cells are cultured in the presence of GM-CSF and IL-4 to thus induce dendritic cells, and the dendritic cells are cultured and pulsed together with the peptide of the present invention, thus enabling the antigen-presenting cell of the present invention to be prepared.

Furthermore, when the antigen-presenting cell of the present invention is prepared by transfecting the cell having an antigen-presenting ability with the polynucleotide of the present invention, the polynucleotide may be in the form of a DNA or the form of an RNA. Specifically, in the case of a DNA, Cancer Res., 56: p. 5672, 1996 or J. Immunol., 161: p. 5607, 1998 (these publications forming part of the present application by reference) may be referred to, and in the case of an RNA, J. Exp. Med., 184: p. 465, 1996 (this publication forming part of the present application by reference) may be referred to.

The antigen-presenting cell can be an active ingredient of a CTL inducer. The CTL inducer containing the antigen-presenting cell as an active ingredient preferably contains physiological saline, phosphate buffered physiological saline (PBS), a medium, etc. in order to maintain the antigen-presenting cell stably. Examples of an administration method include intravenous administration, subcutaneous administration, and intradermal administration. Returning a CTL inducer containing such an antigen-presenting cell as an active ingredient to the body of the patient enables a CTL that is specific to a cancer cell presenting the peptide of the present invention as an antigen to be efficiently induced in the body of a patient having an ASB4-positive cancer, and as a result an ASB4-positive cancer that subjects the peptide of the present invention to antigen presentation can be treated.

<6> Cytotoxic T Cell (CTL) of the Present Invention

The peptide and polynucleotide of the present invention may be utilized in vitro for example as follows. That is, a CTL may be induced by bringing either the peptide or the polynucleotide of the present invention into contact with peripheral blood lymphocytes in vitro. Therefore, one embodiment of the present invention provides a CTL that specifically damages a cell that subjects the peptide of the present invention to antigen presentation, and a method for inducing same. As described above, the peptide and polynucleotide of the present invention can be utilized for preventing and/or treating a cancer. Therefore, the CTL and the induction method therefor of the present embodiment preferably utilize peripheral blood lymphocytes derived from a cancer patient. Specifically, a CTL that specifically damages a cell subjecting the peptide of the present invention to antigen presentation is induced by bringing either the peptide or the polynucleotide of the present invention into contact in vitro with peripheral blood lymphocytes derived from a cancer patient.

In a melanoma for example, it has been confirmed that an adoptive immunotherapy in which a large number of intratumoral infiltrating T cells from the patient in question are cultured in vitro and returned to the patient has a therapeutic effect (J. Natl. Cancer. Inst., 86: 1159, 1994). Furthermore, in a mouse melanoma it has been confirmed that metastasis is suppressed by stimulating splenocytes in vitro with TRP-2 tumor antigen peptide so as to make CTLs specific to the tumor antigen peptide proliferate and administering the CTLs to a melanoma transplanted mouse (J. Exp. Med., 185: 453, 1997). This is based on the result that CTLs that specifically recognize a complex of a tumor antigen peptide and an MHC of an antigen-presenting cell proliferate in vitro. It is therefore considered that a therapy in which peripheral blood lymphocytes of a patient are stimulated in vitro using the peptide or the polynucleotide of the present invention to thus increase tumor-specific CTLs and the CTLs are subsequently returned to the patient will be useful.

The CTLs may be an active ingredient of a therapeutic agent or a preventive agent for a cancer. The therapeutic agent or the preventive agent preferably contains physiological saline, phosphate buffered physiological saline (PBS), a medium, etc. in order to maintain the CTLs stably. Examples of an administration method include intravenous administration, subcutaneous administration, and intradermal administration. Returning the cancer therapeutic or preventive agent containing such CTLs as an active ingredient to the body of a patient enables the cytotoxic action of the CTLs to cancer cells in the body of a patient having the ASB4-positive cancer of the present invention to be promoted, and the cancer to be treated by destroying the cancer cells.

The CTL of the present invention can exhibit cytotoxic activity with, as a target, a complex of an HLA and the peptide of the present invention that is subjected to antigen presentation on a tumor cell. That is, a T cell receptor (TCR) of the CTL of the present invention recognizes a complex of an HLA and the peptide of the present invention. In recent years, an adoptive immunotherapy has been devised in which a TCR gene that recognizes a specific peptide-HLA complex expressed in a CTL is cloned, this TCR gene is transferred to a CD8+ T cell harvested from a cancer patient to thus artificially produce a CTL, it is cultured on a large scale, and it is then returned to the body of the patient (e.g. Ochi et al., Blood. 2011 Aug. 11; 118 (6): 1495-503, etc.). In the present invention, when an 'artificial CTL' is referred to, it means a CTL that is formed by transferring a gene encoding a TCR that recognizes a complex of a peptide and an HLA to a T cell as described above, and this can also be used in the treatment of a cancer in the same way as for the above natural CTL. Therefore, such an artificial CTL is also included in the CTL of the present invention. In such an embodiment, a TCR that recognizes a complex of the peptide of the present invention and an HLA and that is genetically transferred to an artificial CTL may be modified as appropriate in order to increase the binding affinity toward the complex or the cytotoxic activity. Therefore, the 'artificial CTL' includes a CTL that is formed by appropriately genetically modifying a gene encoding a TCR that recognizes a complex of the peptide of the present invention and an HLA and then transferring the gene to a patient-derived T cell. Preparation of an artificial CTL may employ a method known in the present technical field.

<7> Tumor-Specific CTL-Detecting Agent Using the Peptide of the Present Invention The peptide of the present invention is recognized by a tumor-specific CTL, and is therefore useful as a component of a tumor-specific CTL-detecting agent. Therefore, the present invention also relates to a tumor-specific CTL-detecting agent containing the peptide of the present invention. In one embodiment, the tumor-specific CTL-detecting agent of the present invention contains an HLA multimer (monomer, dimer, tetramer, pentamer, or Dextramer) containing HLA-A02 or HLA-A24 and the peptide of the present invention.

For example, the HLA tetramer means a tetramer formed by biotinylating a complex (HLA monomer) in which the α chain and the β2 microglobulin of the HLA are associated with a peptide (epitope peptide) and binding it to avidin (Science 279: 2103-2106 (1998), Science 274: 94-96 (1996)). At present HLA tetramers containing various types of antigen peptides are commercially available (e.g. from Medical & Biological Laboratories Co., Ltd.), and an HLA tetramer containing the peptide of the present invention and HLA-A02 or HLA-A24 can be easily prepared. Furthermore, an HLA dimer and an HLA pentamer are also based on the same principle, the HLA monomer being formed into the dimer and the pentamer respectively. Therefore, an HLA multimer containing the peptide of the present invention and HLA-A02 or HLA-A24 is also one embodiment of the present invention.

Specific examples include an HLA tetramer containing a peptide with an amino acid sequence described in any of SEQ ID Nos: 3-14 and HLA-A02 or HLA-A24. The HLA tetramer is preferably fluorescently-labeled so that bound CTLs can be easily screened or detected by known detection means such as flow cytometry or a fluorescence microscope. Specific examples include HLA tetramers labeled with phycoerythrin (PE), fluorescein isothiocyanate (FITC), peridinin chlorophyll protein (PerCP), etc.

Examples of methods for producing an HLA tetramer include those described in the literature, such as Science 279: 2103-2106 (1998) and Science 274: 94-96 (1996), which are described in brief below.

First, *Escherichia coli* or mammalian cells that can express a protein are transfected with an HLA-A24 or HLA-A02α chain expression vector and a β2 microglobulin expression vector and expression is carried out. In this embodiment, it is preferable to use *Escherichia coli* (for example, BL21). The monomer HLA-A24 or HLA-A02 complex thus obtained and the peptide of the present invention are mixed to thus form a soluble HLA-peptide complex. Subsequently, the C terminal site sequence of the α chain of HLA-A02 or HLA-A24 in the HLA-peptide complex is biotinylated with BirA enzyme. This biotinylated HLA-peptide complex and fluorescently-labeled avidin are mixed at a molar ratio of 4:1, thus preparing an HLA tetramer. In each of the above steps, it is preferable to carry out protein purification by means of gel filtration, etc.

<8> Cancer Stem Cell-Detecting Agent

As described above, the present inventors have found for the first time that ASB4 is highly expressed specifically in a cancer stem cell. That is, it has been found for the first time by the present inventors that ASB4 is a gene whose expression is not observed in a cancer cell except a cancer stem cell or a normal somatic cell, but that is highly expressed in a cancer stem cell. It has been found from such a finding that ASB4 can be utilized as a marker for identifying a cancer cell, and in particular a cancer stem cell. Therefore, one aspect of the present invention relates to a cancer stem cell-detecting agent that contains an ASB4-detecting agent for detecting an expression product of ASB4.

In the present invention, when just 'ASB4' is used, it means an ASB4 gene unless otherwise specified. It preferably means a human ASB4 gene but it may be a homolog thereof.

In the present invention, 'gene expression' means a series of biological reactions initiated by gene transcription, and an 'expression product' is a molecule produced by this series of biological reactions, such as an mRNA or an endogenous polypeptide. An endogenous polypeptide, which is a gene expression product, is preferably a protein that is the final product of gene expression.

In the present invention, an 'ASB4-detecting agent' means an agent for qualitatively and/or quantitatively detecting an ASB4 gene or an expression product thereof.

The cancer stem cell-detecting agent of the present invention contains an ASB4-detecting agent for detecting an ASB4 expression product. When an ASB4 expression product is detected in a detection target, it can be determined that the detection target has a cancer stem cell, i.e., a cancer stem cell has been detected. The cancer stem cell-detecting agent of the present invention can be used in vivo or in vitro, but it is preferably used in vitro for a cell population derived from a biological sample (detection target) harvested from a biological individual (test subject). In this case, detection of a cancer stem cell in a detection target which is a cell population derived from a biological sample means that a cancer stem cell has been detected in a test subject, i.e., biological individual from which a biological sample has been harvested, that is, the biological individual has a cancer stem cell. Therefore, as described herein below, a method for detecting a cancer stem cell in a test subject using the cancer stem cell-detecting agent of the present invention is also included in the present invention.

The biological individual as a test subject may be any biological individual as long as it is a biological individual that can have a tumor but is preferably a human or a non-human mammal individual (e.g. a rodent such as a mouse, a rat, a guinea pig, or a hamster, a primate such as a chimpanzee, an artiodactyl such as a cow, a goat, or a sheep, a perissodactyl such as a horse, a rabbit, a dog, a cat, etc.), and more preferably a human individual.

The cell population as a detection target can be any biological sample-derived cell population obtained from the test subject but is preferably a cell population derived from a biological sample obtained from a human, and more preferably a cell population containing a cell derived from one or more biological samples selected from the group consisting of heart, brain, placenta, lung, liver, skeletal muscle, kidney, pancreas, spleen, thymus, prostate, testis, ovary, small intestine, large intestine, and blood, which is confirmed that almost no ASB4 is expressed.

The ASB4-detecting agent contained in the cancer stem cell-detecting agent of the present invention can be changed depending on the expression product that is to be detected, and a person skilled in the art can select the most suitable one as appropriate. Specifically, for example, when the expression product is an mRNA, any mRNA detection method known in the present technical field may be used, and examples include, but are not limited to, an RT-PCR method, an in situ hybridization method, a Northern blotting method, and real time RT-PCR and, among them, a RT-PCR method is preferable from the viewpoint of high detection sensitivity and ease of experimental technique. For example, when the expression product is an endogenous polypeptide (preferably an ASB4 protein), examples include, but are not limited to, a Western blotting method and immunohistochemical staining. The ASB4-detecting agent used can be changed depending on the expression product that is to be detected and the detection method employed, and a person skilled in the art can select the most suitable one as appropriate. Specifically, for example, when an endogenous polypeptide is to be detected, an ASB4-specific antibody (preferably a monoclonal antibody), etc. can be cited, and when an mRNA is to be detected, a probe and/or a primer that have a base sequence complementary to the part of the base sequence described in SEQ ID No: 1 (Genbank Accession No: NM_016116.2, positions 72 to 1352) can be cited, but examples are not limited to the above. Moreover, the expression product that is to be detected may be a single expression product or a combination of a plurality of expression products.

<9> Antibody that Recognizes the Peptide of the Present Invention

As described above, the peptide of the present invention is presented as a CTL epitope peptide on a cancer cell, and in particular a cancer stem cell. In this process, it is presented on a cell surface by forming a complex with an MHC. Therefore, it is possible to utilize the peptide of the present invention as a tumor marker or a target of an antibody medicament by the use of an antibody that specifically recognizes the peptide of the present invention or the complex. Examples of such an antibody include an antibody (preferably a monoclonal antibody) that specifically binds to the peptide of the present invention, and a TCR (T cell antigen receptor)-like antibody that recognizes a complex of the peptide of the present invention and an HLA, preferably HLA-A24 or HLA-A02. Therefore, the present invention also relates to an antibody that recognizes the peptide of the present invention and a T cell antigen receptor-like antibody that recognizes a complex of said peptide and an MHC.

In the present invention, when referring to an 'antibody', not only immunoglobulin molecules, but also functional fragments of antibodies such as Fab, Fab', F(ab')2, Fv, scFv, dsFv, diabody and sc(Fv)2 are included. Multimers (for example, dimers, trimers, tetramers, polymers) of these functional fragments are also included in the antibody of the present invention.

In the present invention, the 'TCR-like antibody' is a molecule having binding ability (antigen-recognizing ability) similar to TCR to a complex of a fragmented antigen-derived peptide and a major histocompatibility complex (MHC) molecule (pMHC). For example, as reported in Eur J Immunol. 2004; 34: 2919-29, etc., a TCR-like antibody that recognizes a complex of a tumor antigen-derived peptide and an MHC can recognize a cancer cell that is presenting a tumor antigen peptide that can be targeted by a CTL, a dendritic cell that has phagocytized a cancer cell and is presenting a tumor antigen peptide on an MHC class I, etc.

Furthermore, the TCR-like antibody that recognizes a complex of an MHC and a peptide derived from a virus, etc. can quantitatively and chronologically analyze what kind of presentation kinetics, CTL response, etc. a presented antigen will show on an infected cell.

The TCR-like antibody may be prepared by a method described in Eur J Immunol. 2004; 34: 2919-29, etc. For example, immunizing an animal such as a mouse with an MHC-peptide complex enables an antibody that is specific to the complex to be obtained. It is also possible to obtain a complex-specific antibody by utilizing a phage display method.

As described above, recognizing the peptide of the present invention and an MHC complex presenting said peptide enables a tumor cell that presents the MHC complex on the cell surface to be detected. Therefore, the present invention also relates to a tumor-detecting agent containing the above-mentioned antibody or the TCR-like antibody. Furthermore, since the peptide of the present invention is similarly presented on an antigen-presenting cell, preferably a professional antigen-presenting cell such as a dendritic cell, in addition to a tumor cell, the above antibodies are also useful for detection of an antigen-presenting cell, etc. presenting the peptide of the present invention.

In addition, as described above, since the peptide of the present invention is presented as a CTL epitope peptide by a cancer cell and in particular a cancer stem cell, an antibody or a TCR-like antibody that recognizes the peptide of the present invention or a complex of the peptide of the present invention and an HLA, preferably HLA-A24 or HLA-A02 is also useful as a preventive and/or therapeutic agent for cancer in a subject. Accordingly, the present invention also relates to a preventive and/or therapeutic agent for cancer comprising an antibody and/or a TCR-like antibody of the present invention.

Since the peptide of the present invention is presented as a CTL epitope peptide by a tumor cell, an antibody or a TCR-like antibody that recognizes the peptide of the present invention or a complex of the peptide of the present invention and an HLA, preferably HLA-A24 or HLA-A02 can bind to said peptide and/or said complex present on the cell surface in a subject. When the antibody binds to the surface of a tumor cell, the Fc receptor of an effector cell such as macrophage or NK cell binds to the Fc site of the antibody, and antibody-dependent cellular cytotoxicity (ADCC) activity that the effector cell attacks the tumor cell is generated, thereby enabling treatment of the tumor. Therefore, the antibody and/or the TCR-like antibody can be used as an active ingredient of a preventive and/or therapeutic agent for cancer.

In recent years, bi-specific antibodies that are modified to have two different antigen binding sites, with each site binding to different antigens, have been developed. Bi-specific antibodies wherein a peptide presented as an antigen or a cancer cell surface antigen such as a MHC-antigen peptide complex is recognized at one antigen binding site, and a lymphocyte surface antigen such as CD3 is recognized at the other antigen binding site, are able to restrict and integrate cells having lymphocyte surface antigens such as CTL and effector cells in the vicinity of cancer cells. Lymphocytes restricted in the vicinity of cancer cells themselves not only exhibit antitumor activity such as ADCC activity, but also activate naive immune cells in an anti-tumor manner around the cancer cells by secretion of cytokines and the like; thus, they can attack cancer cells by exhibiting bystander effect.

Accordingly, the present invention also encompasses a bi-specific antibody which specifically recognizes the peptide of the present invention and/or a complex of the peptide and an HLA, as well as a lymphocyte surface antigen. The lymphocyte surface antigen that is specifically recognized is not particularly limited as long as it is an antigen that is specifically expressed on the surface of lymphocytes, but preferably it includes CD3, CD16, CD64 and the like. In particular, CD3 is a cell surface antigen involved in the induction of cytotoxic activity of CTL, and when CD3 binds to an antibody, CTL can be activated in a HLA-unrestricted manner, without recognizing a HLA-cancer antigen complex; thus, the exhibition of strong cytotoxic activity can be expected, which is preferable.

Furthermore, in recent years, a new immune cell therapy has been devised, which includes, forming a chimeric antigen receptor (CAR) by genetically engineering and modifying a part of a monoclonal antibody specific to tumor antigen, genetically transferring it to a patient-derived T cell, culturing and amplifying this genetically modified T cell ex vivo, and injecting the genetically modified T cells into the patient (Nat Rev Immunol. 2012; 12: 269-81). Specifically, peripheral blood mononuclear cells harvested from a patient are cultured in the presence of an anti-CD3 antibody and IL-2, etc. to thus activate T cells, and a gene encoding CAR is introduced into the T cells by the use of a transfection vector such as a retrovirus vector or a lentivirus vector to thus prepare genetically modified T cells.

In the present invention, the 'chimeric antigen receptor' is a chimeric protein molecule that has been designed so as to have at the N terminal a single chain antibody (scFv) which a light chain and a heavy chain of an antibody variable region of an antibody that recognizes a molecule present on the cell surface of a cancer cell is tandemly linked, and have at the C terminal a CD3ζ chain among molecules constituting a T cell receptor (TCR)/CD3 complex. This chimeric antigen receptor recognizes a specific antigen via the scFv region, then causing activation of a T cell via the CD3ζ chain. In order to enhance the activation of a T cell, one or more costimulators (e.g. CD28, 4-1BB, ICOS, etc.) may be incorporated between the scFv and the ζ chain. In the present invention, as the scFv, a CAR may be prepared using the TCR-like antibody of the present embodiment (including an antibody molecule designed from the TCR-like antibody or a fragment thereof). Since a CAR that recognizes a complex of a tumor antigen-derived peptide and an MHC can recognize a cancer cell that is presenting a tumor antigen peptide that can be targeted by a CTL, a dendritic cell that has phagocytized a cancer cell and is presenting a tumor antigen peptide on an MHC class I, etc., the genetically modified T cell into which the CAR has been introduced is useful as a preventive and/or therapeutic agent for cancer that is specific to the tumor antigen, in the same way as for the artificial CTL. Therefore, the present invention also relates to a preventive and/or therapeutic agent for cancer containing a genetically modified T cell or an artificial CTL into which has been introduced a CAR that recognizes a complex of the tumor antigen-derived peptide of the present invention and an MHC.

<10> Tumor Detection Method (Test Method, Diagnostic Method)

The present invention provides a tumor detection method (test method, diagnostic method) utilizing the CTL-detecting agent, the cancer stem cell-detecting agent, or the tumor-detecting agent of the present invention, which are described above.

The detection method (diagnostic method) of the present invention using the CTL-detecting agent of the present invention typically involves harvesting blood from a test subject or harvesting part of the test tissue for which a tumor is suspected by means of a biopsy, etc., and detecting/measuring the amount of CTLs that recognize a complex of an HLA antigen and an ASB4-derived tumor antigen peptide contained therein by means of the CTL-detecting agent of the present invention, thus detecting, testing, or diagnosing the presence or absence or the extent of an ASB4-positive cancer (tumor) such as colon cancer, lung cancer, kidney cancer, breast cancer, oral cancer, cervical cancer, thyroid cancer, testicular tumor, or ovarian cancer.

The detection method (test method, diagnostic method) of the present invention using the cancer stem cell-detecting agent of the present invention typically involves detecting, testing, or diagnosing the presence or absence or the extent of an ASB4-positive cancer (tumor) such as colon cancer, lung cancer, breast cancer, oral cancer, cervical cancer, thyroid cancer, testicular tumor, or ovarian cancer by harvesting blood from a test subject or harvesting by means of biopsy, etc. part of the test tissue for which a tumor is suspected, and detecting/measuring the amount of ASB4 expression product contained therein using the cancer stem cell-detecting agent of the present invention.

The detection method (test method, diagnostic method) of the present invention using the tumor-detecting agent of the present invention typically involves harvesting blood from a test subject or harvesting part of the test tissue for which a tumor is suspected by means of a biopsy, etc., and detecting/measuring the amount of cells presenting a complex of an HLA antigen and an ASB4-derived tumor antigen peptide contained therein by means of the tumor-detecting agent of the present invention, thus detecting, testing, or diagnosing the presence or absence or the extent of an ASB4-positive cancer (tumor) such as colon cancer, lung cancer, breast cancer, oral cancer, cervical cancer, thyroid cancer, testicular tumor, or ovarian cancer.

For example, the detection (test, diagnostic) method of the present invention can detect (test, diagnose) the presence or absence or the extent of improvement of a tumor when a therapeutic drug is administered to a patient having a tumor in order to improve the tumor. Furthermore, the detection (test, diagnostic) method of the present invention may be applied to the screening of a patient to be treated to whom a medicament containing the peptide or the polynucleotide of the present invention as an active ingredient can be applied effectively, and to the prediction, assessment, etc. of the therapeutic effect of the medicament. Moreover, in an embodiment in which the tumor-detecting agent of the present invention is used, it is possible to detect a cancer cell presenting a tumor antigen peptide that can be actually targeted by a CTL induced within the living body of a patient by administering a cancer vaccine containing the peptide of the present invention as an active ingredient.

A specific embodiment of the detection (test) method of the present invention using the CTL-detecting agent of the present invention includes steps (a) and (b), and optionally step (c), as follows:
(a) a step of bringing a biological sample obtained from a test subject into contact with the CTL-detecting agent of the present invention,
(b) a step of measuring the amount of CTLs that recognize a complex of an HLA antigen and an ASB4-derived tumor antigen peptide in the biological sample using the amount of cells to which the CTL-detecting agent binds as an indicator, and
(c) a step of determining the presence of a cancer based on the result of (b).

A specific embodiment of the diagnostic method of the present invention using the CTL-detecting agent of the present invention includes steps (a), (b), and (c) above.

A specific embodiment of the detection (test) method of the present invention using the cancer stem cell-detecting agent of the present invention includes steps (d) and (e), and optionally step (f), as follows:
(d) a step of bringing a biological sample obtained from a test subject into contact with the cancer stem cell-detecting agent of the present invention,
(e) a step of measuring the amount of ASB4 expression product in the biological sample, and
(f) a step of determining the presence of a cancer based on the result of (e).

A specific embodiment of the diagnostic method of the present invention using the cancer stem cell-detecting agent of the present invention includes steps (d), (e), and (f) above.

An embodiment of the method for detecting a cancer stem cell using the cancer stem cell-detecting agent of the present invention includes steps (d) and (e) and step (f') below instead of (f):
(f') a step of determining the presence or absence of a cancer stem cell in a biological sample based on the result of (e).

Examples of the biological sample used here include a sample prepared from biological tissue (a tissue for which the presence of cancer cells is suspected, surrounding tissue thereof or blood etc.) of a test subject. Specific examples include a sample containing tissue cells harvested from the tissue.

A specific embodiment of the detection (test) method of the present invention using the tumor-detecting agent of the present invention includes steps (g) and (h), and optionally step (i), as follows:
(g) a step of bringing a biological sample obtained from a test subject into contact with the tumor-detecting agent of the present invention,
(h) a step of measuring the amount of cells that present a complex of an HLA antigen and an ASB4-derived tumor antigen peptide in the biological sample using the amount of cells to which the tumor-detecting agent binds as an indicator, and
(i) a step of determining the presence of a cancer based on the result of (h).

A specific embodiment of the diagnostic method of the present invention using the tumor-detecting agent of the present invention includes steps (g), (h), and (i) above.

Examples of the biological sample used here include a sample prepared from biological tissue (a tissue for which the presence of cancer cells is suspected, surrounding tissue thereof or blood etc.) of a test subject. Specific examples include a sample containing tissue cells harvested from the tissue.

One embodiment of the detection method (test method, diagnostic method) of the present invention using the CTL-detecting agent of the present invention is carried out by detecting a CTL specific to the peptide of the present invention in a biological sample and measuring the amount thereof. Specifically, a tetramer (HLA tetramer) of a complex of a fluorescently-labeled HLA antigen and the peptide of the present invention is prepared in accordance with a method described in the literature (Science, 274: p. 94, 1996, this publication forming part of the present application by reference), and this can be used for quantitatively determining by means of a flow cytometer the amount of antigen peptide-specific CTLs in peripheral blood lymphocytes of a patient for whom a cancer is suspected.

The prediction, assessment, determination, or diagnosis of the presence or absence of a tumor may be carried out by, for example, measuring the amount of CTLs specific to the peptide of the present invention in the blood or test tissue for which a tumor is suspected of a test subject or the amount of cells presenting the peptide of the present invention. In this process, in some cases, the level of ASB4 gene expression, the level of the peptide of the present invention, or the level of CTLs, etc. in the corresponding normal tissue may be used as a reference value, and this reference value may be compared with the level in the sample obtained from the test subject, the difference between the two being assessed.

The comparison of the levels between the test tissue of the test subject and the corresponding normal tissue may be carried out in parallel with measurement of the biological sample of the test subject and a biological sample of a healthy subject. When it is not carried out in parallel, the average value or the statistical median of the amounts of CTLs specific to the peptide of the present invention or the amounts of cells presenting the peptide of the present invention obtained using a plurality (at least two, preferably at least three, and more preferably at least five) of normal tissue pieces under uniform measurement conditions may be used in the comparison as the value for a healthy subject, that is, a reference value.

A determination of whether or not a test subject has a cancer may be carried out using as an indicator, for example, the amount of CTLs specific to the peptide of the present invention in tissue of the test subject or the cells presenting the peptide of the present invention being for example at least twice the level thereof in a healthy subject, and preferably at least three times.

Furthermore, in a test subject to which the peptide or the polynucleotide of the present invention is administered, it is also possible by measuring the amount of CTLs specific to the peptide of the present invention to assess whether or not CTLs have actually been induced. For example, it is possible to assess whether the treatment with the peptide or the polynucleotide of the present invention is effective by using as an indicator the amount of CTLs specific to the peptide of the present invention in the tissue of the test subject being for example at least twice the level thereof of a healthy subject, and preferably at least three times.

<11> Preventive and/or Therapeutic Method for Cancer

The present invention also relates to a method for preventing and/or treating a cancer in a subject, the method including a step of administering an effective amount of an active ingredient selected from the group consisting of the peptide, the polynucleotide, the CTL, the antigen-presenting cell, the antibody and/or the TCR-like antibody, the artificial CTL, and the genetically modified T cell of the present invention to a subject requiring same.

The 'subject' in the present invention may be any biological individual as long as it is a biological individual who can suffer from a cancer, but is preferably a human or a non-human mammal individual (e.g. a rodent such as a mouse, a rat, a guinea pig, or a hamster, a primate such as a chimpanzee, an artiodactyl such as a cow, a goat, or a sheep, a perissodactyl such as a horse, and a rabbit, a dog, a cat, etc.), and more preferably a human individual. In the present invention, the subject may be healthy or may have any disease, but when the prevention and/or therapy of a cancer is intended, it typically means a subject having a cancer or having a risk thereof. In one embodiment of the present invention, the subject is HLA-A02-positive or HLA-A24-positive. In one embodiment of the present invention, the subject has an ASB4-positive cancer or has a risk thereof. In one embodiment of the present invention, the subject is HLA-A02-positive or HLA-A24-positive and has an ASB4-positive cancer or has a risk thereof.

With regard to the peptide, the polynucleotide, the CTL, the antigen-presenting cell, the antibody and/or the TCR-like antibody, the artificial CTL, and the genetically modified T cell of the present invention used in the preventive/therapeutic method of the present invention, any one described in the present specification can be cited. The effective amount referred to in the present invention is an amount that for example reduces the symptoms of a cancer or delays or halts the progress thereof, and is preferably an amount that suppresses or cures a cancer. Furthermore, it is preferably an amount that does not cause an adverse effect that exceeds the benefit obtained by administration. Such an amount may be determined as appropriate by means of an in vitro test using cultured cells, etc. or a test in a model animal such as a mouse or a rat, and such test methods are well known to a person skilled in the art. The specific dose of an active ingredient may be determined while taking into consideration various conditions related to a subject requiring same, for example, the seriousness of symptoms, the general health state, age, and body weight of the subject, the sex of the subject, diet, timing and frequency of administration, concomitant medication, response to treatment, dosage form, compliance with treatment, etc.

In the case of for example the peptide of the present invention, the specific dose is usually 0.0001 mg to 1000 mg, preferably 0.001 mg to 1000 mg, and more preferably 0.1 mg to 10 mg, and this is preferably administered once in a few days to a few months. Furthermore, in the case of the polynucleotide of the present invention, it is usually 0.0001 mg to 100 mg, and preferably 0.001 mg to 10 mg, and this is preferably administered once in a few days to a few months. In the case of the antibody and/or the TCR-like antibody of the present invention, it is usually 0.0001 mg to 2000 mg, and preferably 0.001 mg to 2000 mg, and this is preferably administered once in 1 week to 4 weeks. In the case of the genetically modified T cell or artificial CTL of the present invention, it is usually $1 \times 10^4$ to $1 \times 10^8$, and preferably $1 \times 10^5$ to $1 \times 10^7$, and this is preferably administered once in 1 day to 4 weeks. As an administration method, any known appropriate administration method such as intradermal administration, subcutaneous administration, intramuscular administration, or intravenous administration may be used. It is also possible to use an in vivo method in which the peptide or the nucleotide of the present invention is directly administered into the body as well as an ex vivo method in which a specific type of cells are collected from a person, CTLs or antigen-presenting cells are induced in vitro using the peptide or the polynucleotide of the present invention, and these cells are subsequently returned into the body.

One embodiment of the preventive/therapeutic method of the present invention further includes, prior to the administration step, a step of selecting a subject who is HLA-A02-positive or HLA-A24-positive as a subject for the prevention/therapy. This embodiment of the present invention may further include, prior to the selection step, a step of determining the HLA type of a subject. Determination of the HLA type of a subject may be carried out by any known method. Furthermore, one embodiment of the preventive/therapeutic method of the present invention further includes, prior to the administration step, a step of selecting a subject having an ASB4-positive cancer as a subject for the prevention/therapy. This embodiment of the present invention may further include, prior to the selection step, a step of detecting an ASB4-positive cancer in a subject. Detection of an ASB4-positive cancer in a subject may employ the tumor detection method described in <9> above. One embodiment of the preventive/therapeutic method of the present invention further includes, prior to the administration step, a step of screening a subject who is HLA-A02-positive or HLA-A24-positive and has an ASB4-positive cancer as a subject for the prevention/therapy. This embodiment of the present invention may further include, prior to the screening step, a step of determining the HLA type of a subject and a step of detecting an ASB4-positive cancer in a subject.

<12> Method for Screening Cancer Treatment Drugs Using Cancer Stem Cells as Target In an embodiment in which the cancer stem cell-detecting agent of the present invention is used, the amount of ASB4 expression product expressed in a detection target is thought to be correlated with the amount of cancer stem cells in the detection target. Therefore, it is possible by comparing the amounts of ASB4 expression product expressed before and after administering a candidate compound for the cancer treatment drug to a detection target to determine whether or not the candidate compound administered is useful as a cancer treatment drug targeting cancer stem cells.

The screening method of the present invention includes steps (I) and (II), and optionally (III):

(I) a step of measuring a detected amount A of an expression product of the ASB4 gene in a subject before administering a candidate compound for a cancer treatment drug to the subject, (II) a step of measuring a detected amount B of an expression product of the ASB4 gene in the subject after administering the candidate compound to the subject cell population, and (III) a step of determination of the candidate compound as a cancer treatment drug candidate with cancer stem cells as a target when the detected amounts A and B are compared and the detected amount A is significantly larger than B.

A specific embodiment of the screening method of the present invention includes steps (I) to (III) above. The step of measuring the amount detected in step (I) and (II) includes steps (d) and (e) in the detection (test, diagnosis) method.

All patents, applications, and other publications referred to in the present specification are incorporated herein by reference in their entirety.

The present invention is specifically explained below by reference to Examples, but the present invention should not be construed as being limited by these Examples.

EXAMPLES

Experimental Example 1: Detection and Subcloning of SP Fraction of Human Colon Cancer Cells a) Preparation of Reagents 5% fetal calf serum (FCS (HyClone Laboratories))-supplemented DMEM (Sigma-Aldrich) medium was prepared as a medium and warmed at 37° C. Verapamil (Sigma-Aldrich) was adjusted to 50 mM and diluted to 5 mM using the 5% FCS-supplemented DMEM medium. Hoechst 33342 (Lonza) was adjusted to 250 μg/mL using the 5% FCS-supplemented DMEM medium. DNase I (Qiagen) was adjusted to 1 mg/mL using DDW and sterilized by filtration using a 0.2 μm filter.

b) Preparation of Cells for Flow Cytometry (FACS)

A human colon cancer cell line (SW480 (ATCC)) was suspended in 4 mL of the 5% FCS-supplemented DMEM medium, and the number of cells was counted. Furthermore, the 5% FCS-supplemented DMEM medium was added so as to adjust the cell concentration to $10 \times 10^6$ cells/mL, thus giving a sample. Using part of the sample, dispensing was carried out; verapamil was not added to a main sample (verapamil(−) sample), and verapamil was added to a secondary sample so as to give a final concentration of 75 μM (verapamil(+) sample). Subsequently, the Hoechst 33342 solution was added to the verapamil(+) sample and the verapamil(−) sample so as to give a Hoechst 33342 final concentration of 5.0 μM.

The two samples were cultured while shaking at 37° C. for 90 minutes and then cooled on ice. Centrifuging at 1500 rpm and 4° C. was carried out for 5 minutes, and the supernatant was removed. A suspension in 5% FCS-supplemented 1×PBS was formed and transferred to an ice-cooled FACS tube. Centrifuging at 1500 rpm and 4° C. was again carried out for 5 minutes, the supernatant was removed, and a suspension in 5% FCS-supplemented 1×PBS was formed. The same washing was repeated once, and a suspension in 2 mL of 2% FCS-supplemented 1×PBS with 2 mM EDTA was then formed. 2 μL of the DNase I solution was added and mixed, and a cell clump was then removed using a FACS filter (Beckton Dickinson (BD)). After 2 μL of 1 mg/mL propidium iodide (PI) (Sigma-Aldrich) was added, analysis was carried out using a BD FACS Aria II special edition (registered trademark) (BD) as a flow cytometer at a flow rate of 1000 to 2000 cells/sec.

c) Flow Cytometry (FACS)

FACS operation was carried out in accordance with the instruction manual.

First, cells in the verapamil(−) sample were analyzed, and cells in a cell group (side population (SP)) having low emission intensity compared with a main cell group (main population (MP)) were detected (FIG. 1). In order to confirm that SP cells had low Hoechst 33342 dye stainability specific to an ABC transporter, the verapamil(+) sample was analyzed under the same conditions, and it was confirmed that SP cells disappeared (FIG. 1).

The SP cells were isolated, the cells were subjected to centrifuging at 4° C. and 1500 rpm for 15 minutes, the supernatant was removed, and a suspension in 100 to 200 μL of 1×PBS was then formed.

d) Subcloning at Single Cell Level

Figures 1, 2:
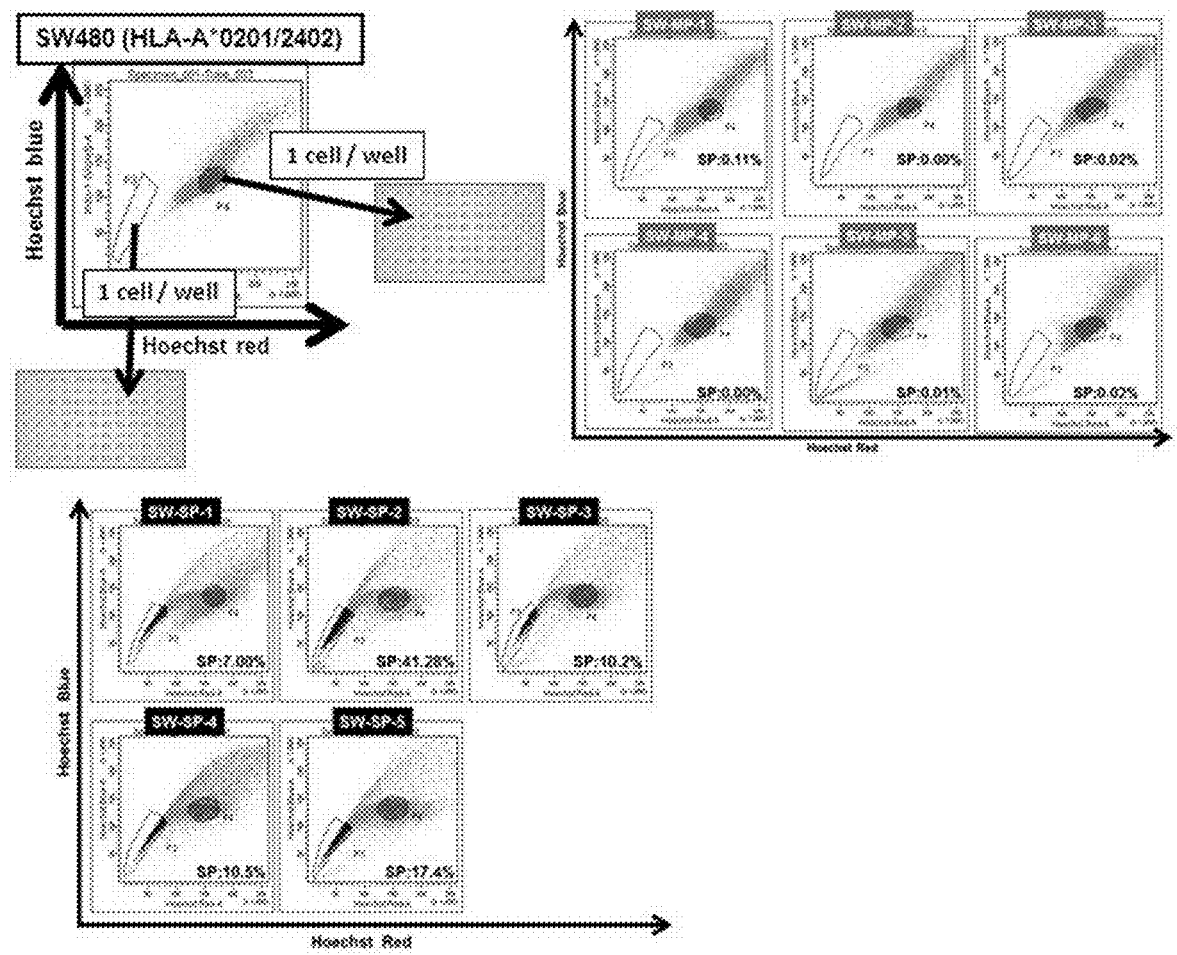

SW480-derived SP cells were detected in c) above, and the SP and MP cell fractions were each subjected to single cell sorting to give 1 cell/well in a 96 well plate (FIG. 2-1). Each well was previously charged with 1% penicillin/streptomycin-containing 10% FCS-supplemented DMEM medium.

After culturing for 2 to 3 weeks, the cell lines proliferating in the wells were defined as an SW480-SP clone cell line or an SW480-MP clone cell line. X and Y in 'SW480-SP-X' or 'SW480-MP-Y' denote clone number.

When the morphology was examined using a confocal microscope, the MP clone cell lines mainly proliferated as a single layer, and each cell showed a spindle shape. On the other hand, the SP clone cell lines showed a tendency for multi-layering, and each cell showed a circular to oval shape. Representative microscopic images of the SP clones and the MP clones obtained are shown in FIG. 2-2.

Experimental Example 2: Tumorigenicity Experiment

In order to confirm the in vivo tumorigenicity of each of the SW480-SP and SW480-MP clone cell lines obtained in Experimental Example 1, the SP clone and the MP clone were each transplanted to a NOD/SCID immunodeficient mouse (Oriental Kobo) using three representative clones thereof.

Figure 3:
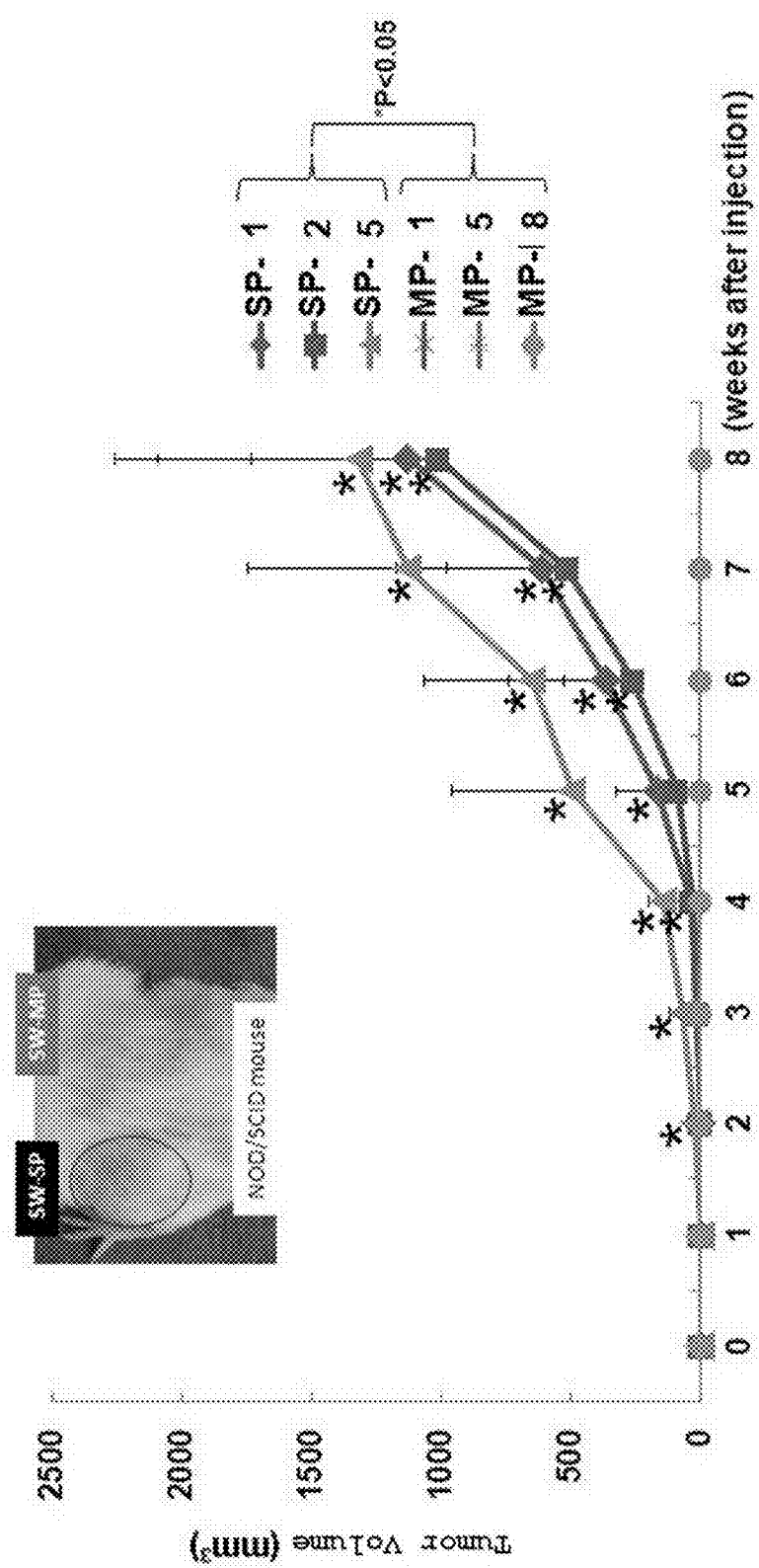
FIG. 3 shows the result of evaluation of a tumor formed when each of the SW480-SP clone cell line and the SW480-MP clone cell line was transplanted into a mouse.

Specifically, the same number of SP and MP clone cells were suspended in 100 μL of 1×PBS on ice and mixed with 100 μL of Matrigel (BD). 100 μL of the cell Matrigel mixed solution was injected subcutaneously under the dorsal skin of a NOD/SCID mouse (Oriental Kobo) so as to give 100, 1000, and 10000 SP and MP clone cells for each group of five animals, and tumor development was examined. The major diameter and the minor diameter of a tumor were measured, and the tumor volume was calculated using the equation (volume=major diameter×(minor diameter)$^2$/2). A tumor growth curve of a mouse into which 10000 cells had been transplanted is shown in FIG. 3.

From the results, in the 10000 cell-transplanted groups, 8 weeks after cell inoculation in the SW480-MP clone transplanted group tumor development could not be observed at all. On the other hand, in the SW480-SP clone transplanted group tumor development was observed in all mice, and the volume of the tumor formed was significantly higher compared with the SW480-MP clone group (FIG. 3). This agrees with the opinion that cancer stem cells are a significant factor in the development of a tumor, and cancer stem cells are concentrated in SP clone cells (Kondo T, Setoguchi T, Taga T. Persistence of a small subpopulation of cancer stem-like cells in the C6 glioma cell line. Proc Natl Acad Sci USA. 20: 781-786, 2004).

Experimental Example 3: Identification of HLA-A24-Binding Natural Peptide in Human Colon Cancer SP Cells Elution and sequence analysis of an HLA-A24-binding natural peptide specifically presented only on the SP fraction cells of the SW480 human colon cancer cell line were carried out by the procedure below.

a) Cell Line

SW480-MP and SW480-SP cell lines, which were the colon cancer cell line-derived clones, were cultured in 10% FCS and 1% penicillin/streptomycin (Gibco)-containing DMEM medium so as to give a cell count in the range of $1.5 \times 10^9$ to $1.8 \times 10^9$.

b) Antibody

An anti-HLA-A24 antibody (C7709A2)-producing hybridoma was donated by Dr. P. G. Coulie (de Duve Institute, Brussel). The hybridoma was cultured in an RPMI-1640 (Sigma-Aldrich) medium to which 10% FCS, 1% penicillin/streptomycin, 55 µM 2-mercapto ethanol (Gibco), 1 mM sodium pyruvate (Gibco), 2 mM L-glutamine (Sigma-Aldrich), and 20 mM HEPES (Gibco) had been added, and a concentrated antibody was obtained from the culture supernatant by a reverse osmosis method using a cellulose tube and polyethylene glycol (PEG-20000). 0.03% sodium azide and a protease inhibitor cocktail (Roche Diagnostics) were added to the concentrated antibody, and it was stored at 4° C.

c) Binding of Antibody and Beads 30 to 40 mL of the concentrated antibody and 3 mL of protein A Sepharose beads (GE Healthcare) were stirred at 4° C. overnight so as to bind them, and then washed with 0.1 M boric acid and 0.2 M triethanolamine buffer (pH 8.2). The antibody and the beads were covalently bonded by stirring in a 20 mM dimethyl pimelimidate dihydrochloride-containing triethanolamine buffer (pH 8.3) at room temperature for 60 to 90 minutes.

d) Immunoprecipitation of HLA-A24-Binding Peptide

Cells (SW480-SP and SW480-MP) of Experimental Example 3a) were dissolved in a buffer containing 0.5% NP-40, 50 mM Tris HCl (pH 8), 150 mM sodium chloride, and a protease inhibitor. The cell solution was subjected to stepwise centrifuging (10 minutes at 2000 g, 30 minutes at 38000 g, 90 minutes at 100000 g), and the supernatant was collected. The collected supernatant was passed through a 0.5 mL protein A Sepharose suspension column to thus remove components that nonspecifically bound to protein A Sepharose, and then mixed with the antibody-binding protein A Sepharose beads prepared in Experimental Example 3c) to thus bind a complex of a natural peptide and an HLA-A24 molecule to the antibody beads by slowly stirring at 4° C. overnight.

Subsequently, the antibody beads were washed stepwise with four types of buffer ([1] 0.005% NP-40, 50 mM Tris HCl (pH 8.0), 150 mM sodium chloride, 5 mM EDTA, and protease inhibitor; [2] 50 mM Tris HCl (pH 8.0) and 150 mM sodium chloride; [3] 50 mM Tris HCl (pH 8.0) and 450 mM sodium chloride; and [4] 50 mM Tris HCl (pH 8.0)), and the peptide and the HLA-A24 molecule bound to the antibody were then eluted by treatment with 10% acetic acid. Subsequently, only the target peptide was extracted using a 3 kDa cutoff filter (Millipore). This peptide-containing extract was concentrated, dried, and then redissolved using 0.1% formic acid as a solvent, thus giving a sample.

e) Sequence Analysis of Eluted Peptide

The sample obtained in Experimental Example 3d) was fractionated using a nanoflow HPLC (Kya Technologies Corporation), spotted on a MALDI substrate, and then analyzed using a mass spectrometer (Applied Biosystems; MDS SCIEX 4800 MALDI TOF/TOF). Mass spectrometry analysis and peptide sequence analysis employed Applied Biosystems 4000 Series Explorer software (ver. 3.5.3), ProteinPilot 3.0 software (Applied Biosystems), and the ipi-.HUMAN FASTA protein database (ver. 3.71). Among the peptide sequences obtained and among those specific to SW480-SP, the sequence and analytical spectrum of a peptide derived from the ASB4 gene, which is described in Experimental Example 4 and thereafter, are shown in FIG. 4.

f) Discussion

Identification of HLA-A24-binding peptides was possible by a method in which immunoprecipitation using an anti-HLA-A24 antibody and mass spectrometry analysis were combined. These are thought to be natural peptides presented on the surface of colon cancer cells. Furthermore, analysis was carried out using the same method for the MP fraction cells, and by comparing the two, a natural peptide with an amino acid sequence described in SEQ ID No: 3 was identified as a natural peptide that is specifically subjected to antigen presentation on the SP fraction cells.

Experimental Example 4: Expression of Gene Encoding HLA-A24-Binding Natural Peptide a) SP-Specific Gene Expression In Experimental Example 3e), a plurality of HLA-A24-binding natural peptides specific to the SP fraction cells were identified. These peptides are thought to be largely classified into two groups. They are a group for which a gene encoding the peptide is specifically expressed in the SP fraction cells and a group for which a gene encoding the peptide is expressed in both the SP fraction cells and the MP fraction cells, but due to differences in protein expression level or peptide processing, it is not subjected to antigen presentation by HLA-A24 as a natural peptide in the MP.

When, in order to classify the natural peptides identified above for the purpose of the above classification, mRNAs were extracted from SW480-SP and SW480-MP, and gene expression was examined by RT-PCR, the ASB4 gene was identified as one of genes specifically expressing in the SP fraction cell. The results of gene expression analysis are shown in FIG. 5. Extraction and reverse transcription of mRNA respectively employed TRIzol (Invitrogen) and SuperScript (registered trademark) III Reverse Transcriptase (Invitrogen) in accordance with the product package inserts. The primer and conditions for the thermal cycler used in RT-PCR are shown in the tables below. RT-PCR products were subjected to electrophoresis at 100V for 25 minutes using 1.5% agarose gel.

TABLE 1

Primers used for RT-PCR

Primer information

| | |
|---|---|
| G3PDH | fw: 5'-accacagtccatgccatcac-3' (SEQ ID 53) |
| | rv: 5'-tccaccaccctgttgctgta-3 (SEQ ID 54) |
| | (Size of the Predicted amplification product: 450 bp) |
| Asb4 | fw: 5'-ctgtcttgtttggccatgtg-3' (SEQ ID 55) |
| | rv: 5'-gcgtctcctcatcttggttg-3' (SEQ ID 56) |
| | (Size of the predicted amplification product: 288 bp) |

TABLE 2

RT-PCR conditions

| | |
|---|---|
| DreamTaq | 0.1 μl |
| 10 x buffer | 2 μl |
| 2 mM dNTPs | 2 μl |
| Primer fw | 1.2 μl |
| Primer rv | 1.2 μl |
| Template | 1 μl |
| H$_2$O | 12.5 μl |
| Total | 20 μl |

TABLE 3

Thermal cycler conditions

| | | |
|---|---|---|
| 94° C. | 2 min | |
| 94° C. | 15 sec | |
| 63° C. | 30 sec | } 35 cycles |
| 72° C. | 30 sec | |
| 72° C. | 2 min | |
| 4° C. | ∞ | | b) ASB4 Gene Expression in Normal Cells

The ASB4 identified in Experimental Example 4a) was subjected to examination of expression in human adult normal cells. A human adult normal tissue-derived mRNA panel was obtained from Clontech, and RT-PCR was carried out using this. The mRNA panel includes mRNAs derived from adult normal cells and tissues from the heart, brain, placenta, lung, liver, skeletal muscle, kidney, pancreas, spleen, thymus, prostate, testis, ovary, small intestine, large intestine, and peripheral blood mononuclear cells.

First, cDNA was synthesized from mRNA using SuperScript (registered trademark) III reverse transcription enzyme (Invitrogen) in accordance with the kit protocol. With regard to the cDNA thus synthesized, ASB4 cDNA was amplified by means of RT-PCR using a forward (Fw) primer and a reverse (Rv) primer (Table 1). As a control, GAPDH cDNA was amplified by the same method. The PCR conditions are shown in Tables 2 and 3. The amplification product thus amplified was subjected to electrophoresis at 100V for 25 minutes using 1.5% agarose gel. The results are shown in FIG. 6.

c) ASB4 Gene Expression in Cancer Cell Lines

Figure 7:
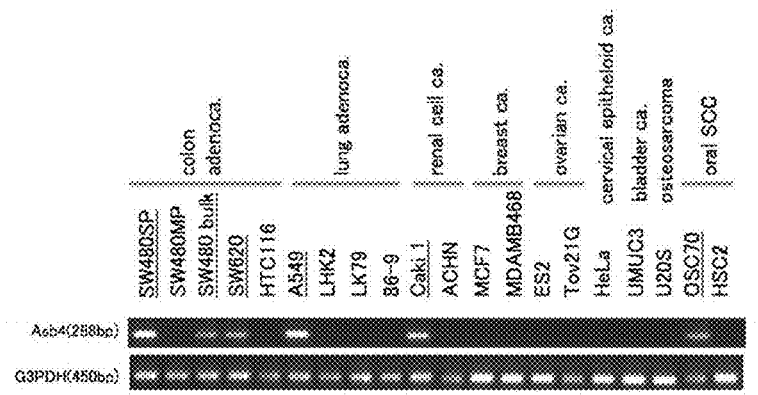
FIG. 7 shows the result of RT-PCR for ASB4 using mRNA derived from various cancer cell lines.

ASB4 gene expression in three types of colon cancer cell lines (SW480, SW620, HTC116), four types of lung cancer cell lines (A549, LHK2, LK79, 86-9), two types of renal cell carcinoma (Caki 1, ACHN), two types of breast cancer cell lines (MDAMB468, MCF7), two types of ovarian cancer cell lines (ES2, Tov21G), one type of cervical cancer cell line (HeLa), one type of bladder cancer cell line (UMUC3), one type of osteosarcoma (U205), and two types of oral cancer cell lines (OSC70, HSC2) was confirmed by the same method as in Experimental Example 4b). The results are shown in FIG. 7.

d) Discussion

We confirmed gene expression of the ASB4 protein that is presented with the HLA-A24 peptide specifically to SW480SP, a stem cell of colon cancer cells (FIG. 5). Expression of the same gene was confirmed in epithelial malignant tumor cell lines such as colon cancer and lung cancer, of which the number of deaths was large domestically and worldwide, while expression was not observed in normal cells in various organs (FIG. 6 and FIG. 7). That is, the ASB4 gene and the peptide as a product thereof are thought to have ideal qualities as cancer treatment targets.

Experimental Example 5: Peptide Binding Assay

Figure 8:
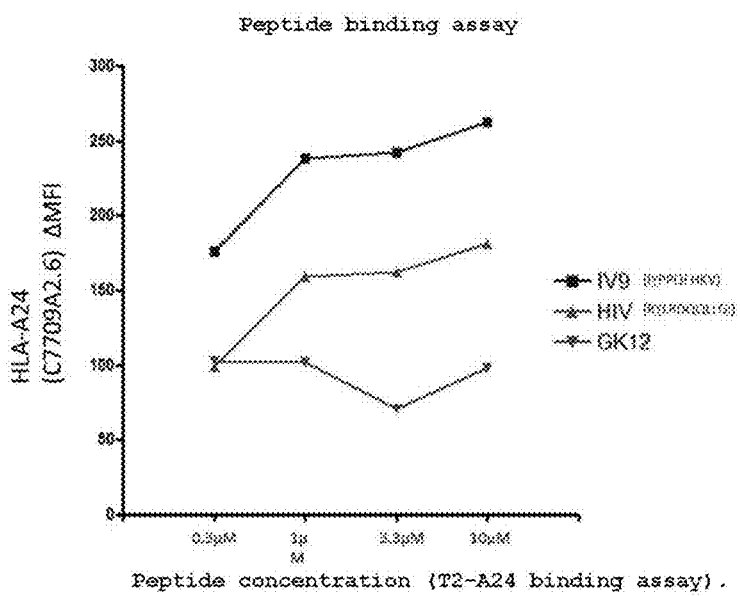
FIG. 8 shows binding ability of ASB4 peptide (IV9; SEQ ID No: 3) to HLA-A24. T2-A24 cells were pulsed with various synthetic peptides such as IV9 and HIV (SEQ ID No: 51), GK12 (SEQ ID No: 52), and the amount of expression of HLA-A24 was evaluated using flow cytometry.

The ability of the ASB4 protein-derived peptide (IV9: SEQ ID No: 3) obtained by mass spectrometry analysis to bind HLA-A24 was examined. First, T2-A24 cells were cultured at 24° C. overnight, and next day the peptide was pulsed at the concentration range (0.3 μM, 1 μM, 3.3 μM and 10 μM) shown in FIG. 8, and incubated at the same temperature for 3 hours and then at 37° C. for 2.5 hours. HIV$_{584-594}$ peptide (amino acid sequence: RYL-RDQQLLGI; SEQ ID No: 51) was used as a positive control, and GK12 peptide (amino acid sequence: GYISPY-FINTSK; SEQ ID No: 52) was used as a negative control. The supernatant was removed by centrifugation (15000 rpm, 5 minutes), and the isolated cell components were treated with an HLA-A24 antibody (C7709A2.6) (incubated at 4° C. for 1 hour). Thereafter, it was washed with PBS, centrifuged to remove the supernatant, and then treated (incubated at 4° C. for 30 minutes) with a secondary antibody (Goat anti-Mouse IgG, FITC). Thereafter, the cells were washed with PBS, and 1% paraformaldehyde phosphate buffer was added to fix the cells. FITC fluorescence intensity was measured using a flow cytometer (FACScan), and the amount of the complex of the synthetic peptide expressed on the cell surface and HLA-A24 was quantified. The results are shown in FIG. 8. As shown in FIG. 8, it was found that the peptide IV9 derived from ASB4 protein has binding activity to HLA-A24.

Experimental Example 6: Induction of Cytotoxic T Cell (CTL)

a) Separation of Human Peripheral Blood Mononuclear Cells (PBMC)

Peripheral blood was collected using a heparin-containing mL syringe from HLA-A24-positive colon cancer patients and HLA-A24-positive healthy controls who had given informed consent. The whole blood was layered in a 50 mL tube (Falcon) to which 13 mL of Lymphoprep (Nycomed) had been added, and subjected to centrifugation at 2000 rpm for 30 minutes. A PBMC layer precipitated on the Lymphoprep layer was recovered using a pipette and washed three times with PBS, thus giving human PBMC.

b) Separation of CD8 positive cells (CD8$^+$) and CD8 negative cells (CD8$^-$)

The PBMC thus separated was suspended in 10 mL of AIM-V culture medium (Life Technologies) and cultured in a 10 cm plastic dish at 37° C. for about 2 hours. The 10 cm dish was gently shaken, floating cells were recovered together with the AIM-V culture medium, and centrifugation was carried out in a 15 mL tube at 1500 rpm for 5 minutes. A pellet thus obtained was suspended in 160 μL of 2 mM EDTA-containing 0.1% BSA-supplemented PBS, 40 μL of CD8 micro beads (Miltenyi Biotec) were added and mixed, culturing was then carried out at 4° C. for 15 minutes, washing with 5 mL of 2 mM EDTA-containing 0.1% BSA-supplemented PBS was carried out, and centrifugation at 1500 rpm for 5 minutes was carried out. 1 mL of 2 mM EDTA-containing 0.1% BSA-supplemented PBS was added to and mixed with the pellet, a magnet-equipped column was loaded with the mixture, washing with 2 mM EDTA-containing 0.1% BSA-supplemented PBS was carried out five times, the column was then detached from the magnet, and the CD8$^+$ cells were recovered. Cells that did not become attached to the column were defined as CD8$^-$ cells.

c) Stimulation of CD8⁺ Cells with Synthetic Peptide

The CD8⁻ cells and the CD8⁺ cells were cultured in a 10% human AB serum (HS)-containing AIM-V culture medium. 1 mg/mL phytohemagglutinin (PHA) (WAKO chemicals) and 100 U/mL interleukin 2 (IL-2) (Takeda Chemical Industries, Ltd.) were added to some of the CD8⁻ cells, and the mixture was cultured for 7 days, thus preparing PHA-blast cells. The PHA-blast cells were mixed with 20 µg/mL of a synthetic peptide IV9 (SEQ ID No: 3) having an ASB4-derived amino acid sequence identified in Experimental Example 3e) and cultured at room temperature for 1 hour. The peptide-pulsed PHA-blast cells were irradiated with 100 Gy using an irradiation machine (Softex), 10 mL of PBS was added, and centrifugation was then carried out at 1500 rpm for 5 minutes. A pellet was suspended in 1 mL of 10% HS-containing AMI-V, and the cell concentration was calculated. $4 \times 10^5$ PHA-blast cells were added to $2 \times 10^6$ CD8⁺ cells, and the mixture was cultured in 1 mL of AIM-V containing 10% HS for 1 week at 37° C. On the 7th day, PHA-blast cells that had been peptide-pulsed in the same manner were irradiated with 100 Gy of radiation and added to the CD8⁺ cells. On the 8th day, 20 U/mL IL-2 was added to the CD8⁺ cells. Stimulation with PHA-blast cells was carried out in the same manner on the 14th day.

Experimental Example 7: Interferon (IFN)-γ ELISPOT Assay a) Preparation of ELISPOT Plate An experiment was carried out using a Human IFNγ ELISPOT set (BD). An ELISPOT plate was coated with anti-IFNγ antibodies, which had been diluted by 200 times, and allowed to stand at 4° C. overnight. The plate was cultured in 10% FCS-supplemented RPMI (Sigma-Aldrich) at room temperature for 2 hours and blocking was carried out, thus giving an ELISPOT plate.

b) Cell Culturing

T2-A24 cells (donated by Dr. Kuzushima, Aichi Cancer Center), which are of a cell line expressed by transferring the HLA-A2402 gene to human lymphoblastoid T2 cells, were pulsed with each peptide at a concentration of 20 µg/mL at room temperature for 1 hour. With regard to the peptide pulse groups there were three groups, that is, [1] no peptide pulse, [2] HIV peptide pulse, and [3] ASB4 peptide pulse. PBS was added subsequent to the peptide pulse, and centrifugation was carried out at 1500 rpm for 5 minutes. A cell pellet was suspended to give $5 \times 10^5$ cells/mL, and an ELISPOT plate was plated with $5 \times 10^4$ cells per well. CTLs were plated at $5 \times 10^4$ cells per well and cultured at 37° C. overnight.

c) Detection of Spot

Figure 9:
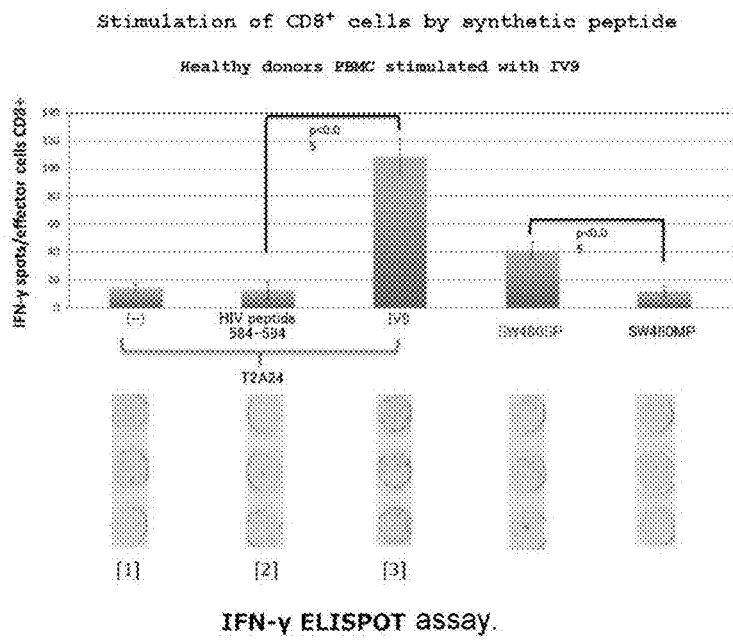
FIG. 9 shows the result of an ELISPOT assay of T2-A24 cells pulsed with various peptides using an ELISPOT plate coated with IFN-γ.

The culture medium and the cells were removed from the ELISPOT plate that had been cultured overnight, and the ELISPOT plate was washed twice with Milli Q water and three times with wash buffer. Biotinylated detection antibody diluted by 250 times was added to each well, and culturing was carried out at room temperature for 2 hours. After washing three times with wash buffer, HRP-labeled streptavidin diluted by 100 times was added to each well, and culturing was carried out at room temperature for 1 hour. After washing three times with wash buffer and washing twice with PBS, a chromogenic reagent was added to each well, and a chromogenic reaction was carried out at room temperature for 15 to 30 minutes. After sufficient visible spot formation was detected, washing with Milli Q water was carried out, and the reaction was thus completed. A nitrocellulose film was dried and then subjected to detection and imaging by KS ELISPOT (ZEISS). As shown in FIG. 9, an IFNγ spot was detected in the ASB4 peptide pulse group.

Experimental Example 8: Cytotoxicity Test

T2-A24 cells, SW480-SP, SW480-MP, and K562 HLA-class I-deficient leukemia cells (obtained from ATCC) were suspended in 10% FBS-supplemented RPMI at a cell concentration of $1 \times 10^6$ cells/mL. Washing was carried out three times with 10 mL of 10% FBS-supplemented RPMI.

T2-A24 cells were pulsed with IV9 peptide and $HIV_{584-594}$ peptide as a positive control for T2-A24 cell binding, at a concentration of 20 µg/mL at room temperature for 1 hour. As a negative control, a group without peptide pulses was used. With regard to experimental group of T2-A24 cells, three groups were defined: [1] no peptide pulse, [2] $HIV_{584-594}$ peptide pulse, and [3] IV9 peptide pulse. In addition, K562 was pulsed with IV9 peptide under the same conditions. Both SW480-SP and SW480-MP groups were used without peptide pulses. After the peptide pulse, the cells were washed twice with PBS. The cells of each group were plated on each well at $1 \times 10^5$ cells/100 µL.

Respective numbers of effector cells (CTLs) were plated on each well so that the effector/target ratio (E/T ratio) became 1, 3, and 9. Effector cells were plated as a spontaneous release well. To the maximum release well, 4% of NP-40-added PBS was added to the target cells so that the final concentration became 2%. After culturing at 37° C. for 6 hours and centrifugation, 100 µl of the supernatant was transferred to a new plate, 100 µl of LDH Cytotoxicity Detection Kit reaction solution (Takara Bio Inc.) was added to each well. After 10 minutes, fluorescence intensity of each well was measured by Terra Scan. Cytotoxic activity was calculated using the equation below.

Cytotoxic activity=(release amount of experimental group−spontaneous release amount of experimental group)/(maximum release amount of experimental group−spontaneous release amount of experimental group)×100

Figure 10:
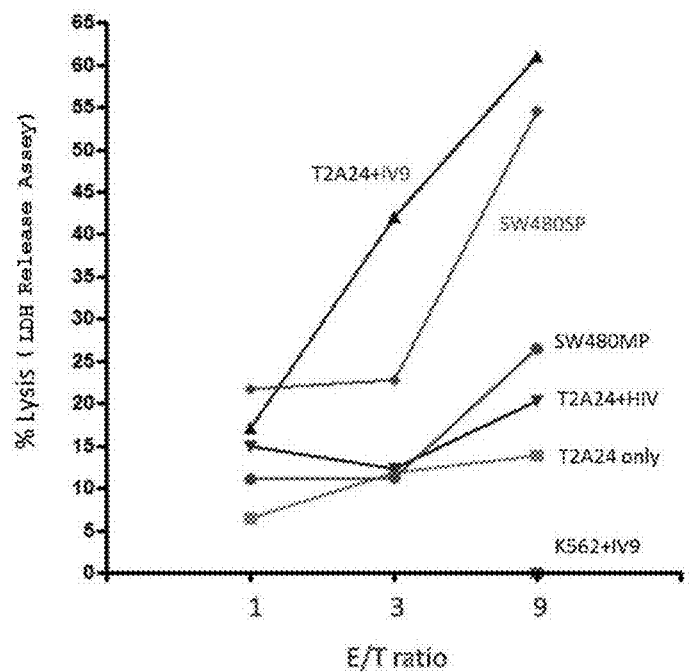
FIG. 10 shows the result of evaluation of cytotoxic activity of an effector cell (CTL) induced from PBMC toward T2-A24 cells pulsed with various peptides and unpulsed SW480-SP cells. The effector cell used was one induced by means of ASB4 peptide IV9 represented by SEQ ID No: 3. K562 cells lacking MHC class I expression were used as a negative control.
Figure 11:
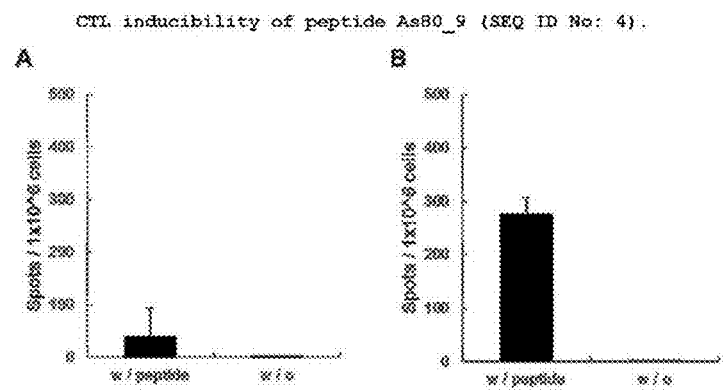
FIG. 11 shows the results of evaluation of in vivo CTL inducibility of the peptide represented by SEQ ID No: 4 (As80_9) by means of an interferon-γ ELISPOT assay. The ordinate denotes the number of spots per given number of seeded cells. 'A' denotes the result of a test using an HLA-A*02:01 transgenic mouse, and 'B' denotes the result of a test using an HLA-A*24:02 transgenic mouse. The black bar ('w/peptide') and the white bar ('w/o') show the results of restimulation culturing of peptide-treated mouse-derived splenocytes in the presence or absence of administered peptide respectively. That is, the differences in the figures between the black bar and the white bar denote the number of peptide-specific CTLs induced in the mouse living body by administration of each of the peptides.
Figure 12:
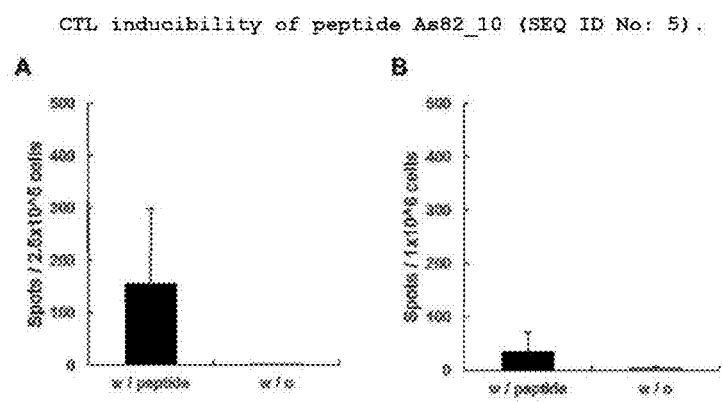
FIG. 12 shows the results of evaluation of in vivo CTL inducibility of the peptide represented by SEQ ID No: 5 (As82_10) by means of an interferon-γ ELISPOT assay. The ordinate, A, B, black bar and white bar are the same as those in FIG. 11.
Figure 13:
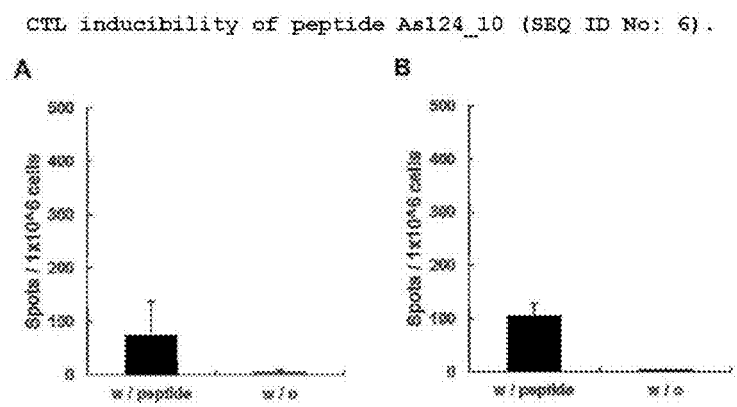
FIG. 13 shows the results of evaluation of in vivo CTL inducibility of the peptide represented by SEQ ID No: 6 (As124_10) by means of an interferon-γ ELISPOT assay. The ordinate, A, B, black bar and white bar are the same as those in FIG. 11.
Figure 14:
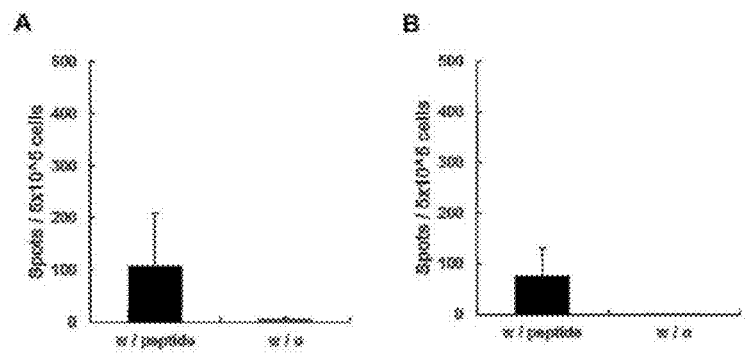
FIG. 14 shows the results of evaluation of in vivo CTL inducibility of the peptide represented by SEQ ID No: 7 (As125_9) by means of an interferon-γ ELISPOT assay. The ordinate, A, B, black bar and white bar are the same as those in FIG. 11.
Figure 15:
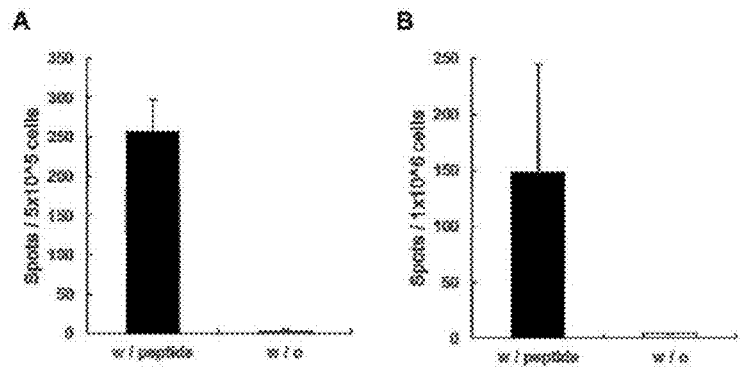
FIG. 15 shows the results of evaluation of in vivo CTL inducibility of the peptide represented by SEQ ID No: 8 (As184_12) by means of an interferon-γ ELISPOT assay. The ordinate, A, B, black bar and white bar are the same as those in FIG. 11.
Figure 16:
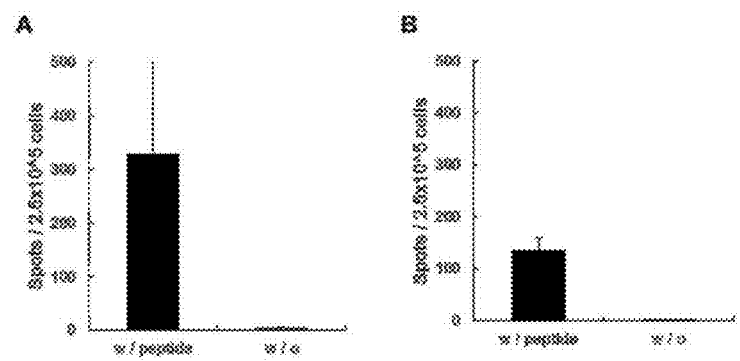
FIG. 16 shows the results of evaluation of in vivo CTL inducibility of the peptide represented by SEQ ID No: 9 (As135_10) by means of an interferon-γ ELISPOT assay. The ordinate, A, B, black bar and white bar are the same as those in FIG. 11.
Figure 17:
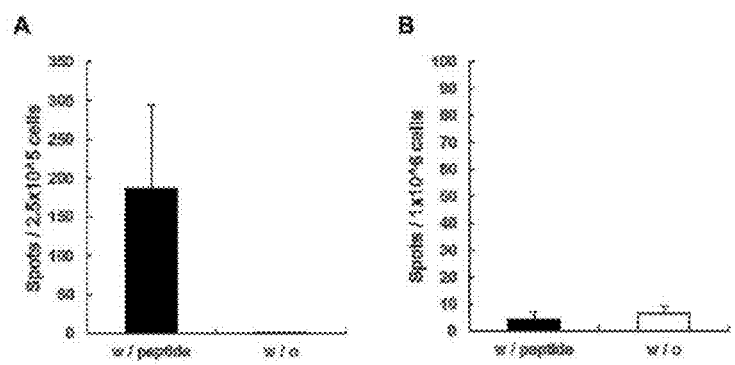
FIG. 17 shows the results of evaluation of in vivo CTL inducibility of the peptide represented by SEQ ID No: 10 (As83_10) by means of an interferon-γ ELISPOT assay. The ordinate, A, B, black bar and white bar are the same as those in FIG. 11.
Figure 18:
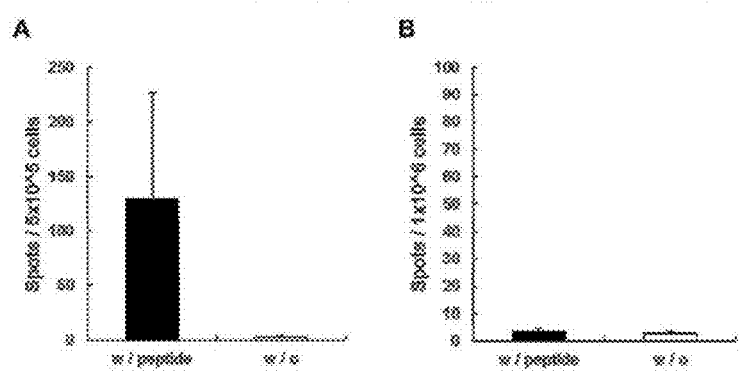
FIG. 18 shows the results of evaluation of in vivo CTL inducibility of the peptide represented by SEQ ID No: 11 (As87_9) by means of an interferon-γ ELISPOT assay. The ordinate, A, B, black bar and white bar are the same as those in FIG. 11.
Figure 19:
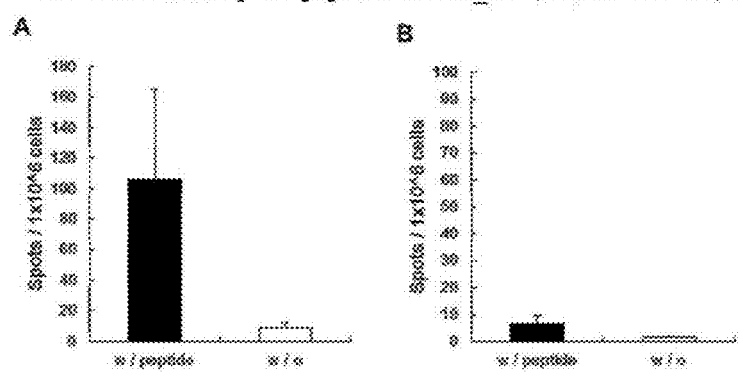
FIG. 19 shows the results of evaluation of in vivo CTL inducibility of the peptide represented by SEQ ID No: 12 (As307_10) by means of an interferon-γ ELISPOT assay. The ordinate, A, B, black bar and white bar are the same as those in FIG. 11.
Figure 20:
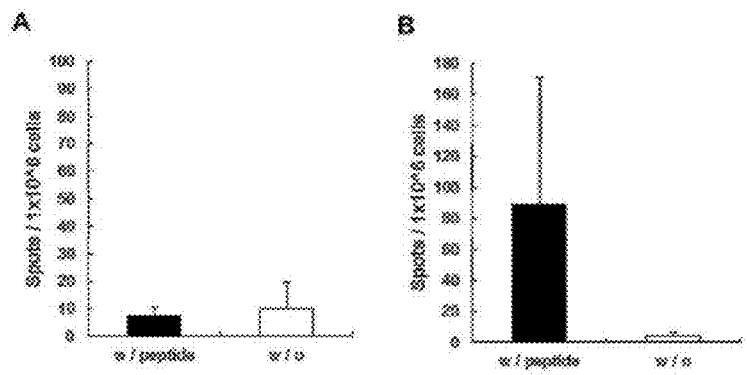
FIG. 20 shows the results of evaluation of in vivo CTL inducibility of the peptide represented by SEQ ID No: 13 (As301_11) by means of an interferon-γ ELISPOT assay. The ordinate, A, B, black bar and white bar are the same as those in FIG. 11.
Figure 21:
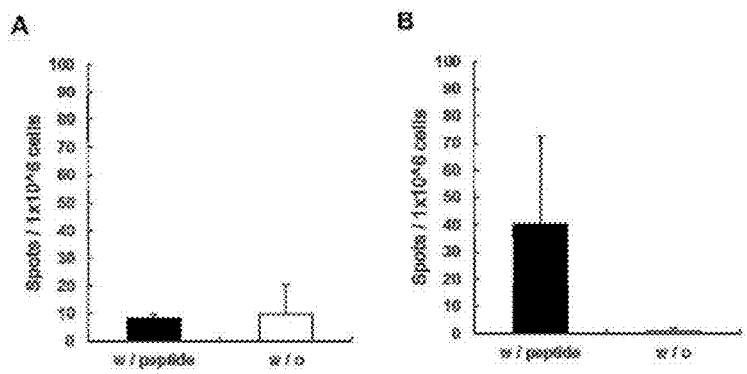
FIG. 21 shows the results of evaluation of in vivo CTL inducibility of the peptide represented by SEQ ID No: 14 (As405_9) by means of an interferon-γ ELISPOT assay. The ordinate, A, B, black bar and white bar are the same as those in FIG. 11.
Figure 22:
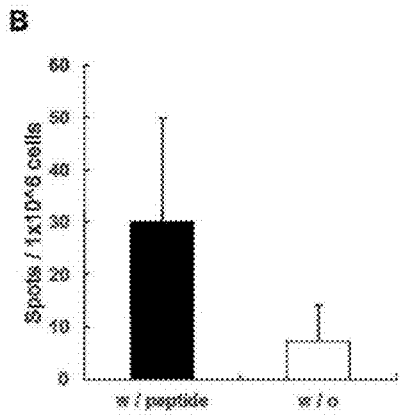
FIG. 22 shows the results of evaluation of in vivo CTL inducibility of the peptide IV9 represented by SEQ ID No: 3 by means of an interferon-γ ELISPOT assay. The ordinate, A, B, black bar and white bar are the same as those in FIG. 11.
Figure 23:
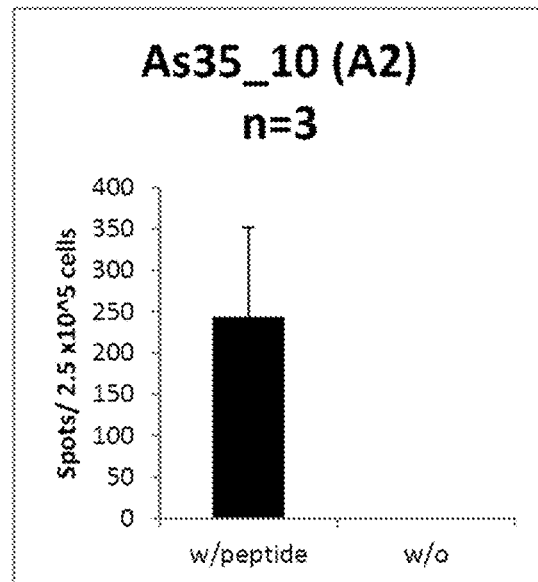
FIG. 23 shows the result of evaluation of in vivo CTL inducibility of the peptide represented by SEQ ID No: 15 (As35_10) by means of an interferon-γ ELISPOT assay using an HLA-A*02:01 transgenic mouse. The ordinate, black bar and white bar are the same as those in FIG. 11.
Figure 24:
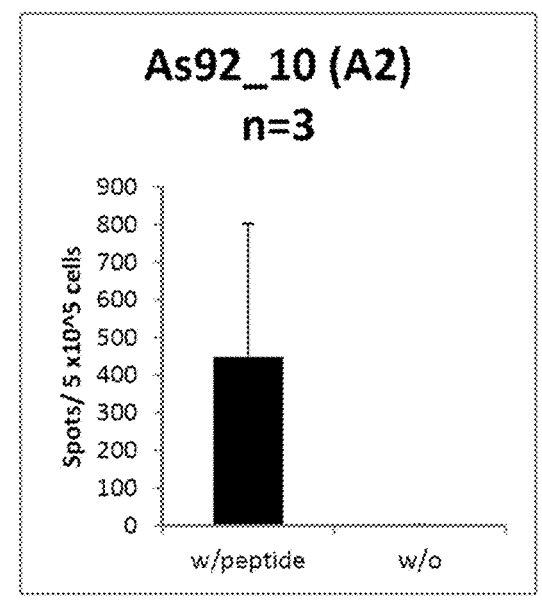
FIG. 24 shows the result of evaluation of in vivo CTL inducibility of the peptide represented by SEQ ID No: 16 (As92_10) by means of an interferon-γ ELISPOT assay using an HLA-A*02:01 transgenic mouse. The ordinate, black bar and white bar are the same as those in FIG. 11.
Figure 25:
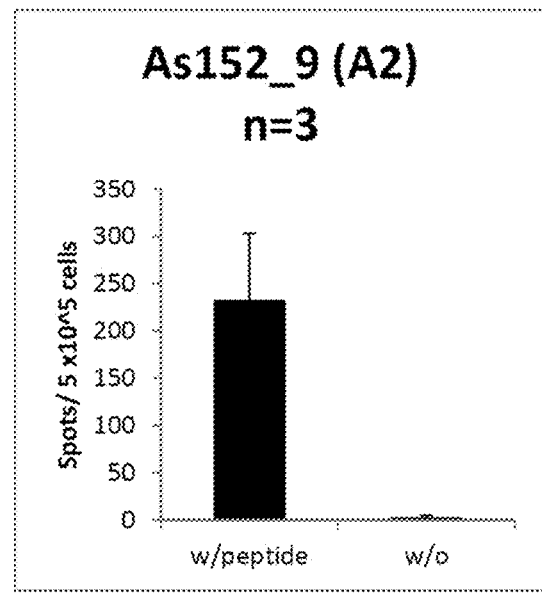
FIG. 25 shows the result of evaluation of in vivo CTL inducibility of the peptide represented by SEQ ID No: 17 (As152_9) by means of an interferon-γ ELISPOT assay using an HLA-A*02:01 transgenic mouse. The ordinate, black bar and white bar are the same as those in FIG. 11.
Figure 26:
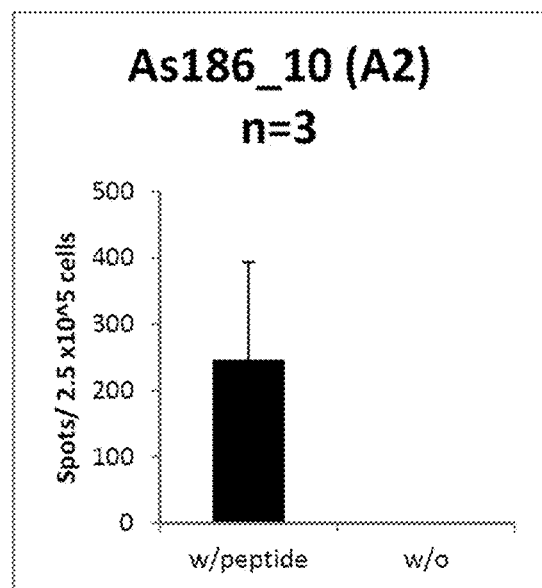
FIG. 26 shows the result of evaluation of in vivo CTL inducibility of the peptide represented by SEQ ID No: 18 (As186_10) by means of an interferon-γ ELISPOT assay using an HLA-A*02:01 transgenic mouse. The ordinate, black bar and white bar are the same as those in FIG. 11.
Figure 27:
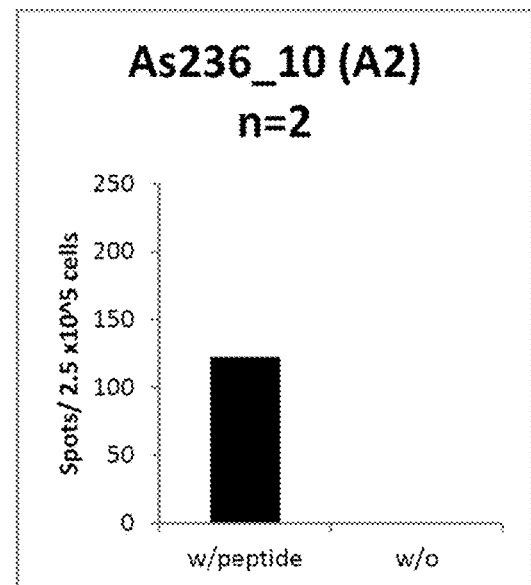
FIG. 27 shows the result of evaluation of in vivo CTL inducibility of the peptide represented by SEQ ID No: 19 (As236_10) by means of an interferon-γ ELISPOT assay using an HLA-A*02:01 transgenic mouse. The ordinate, black bar and white bar are the same as those in FIG. 11.
Figure 28:
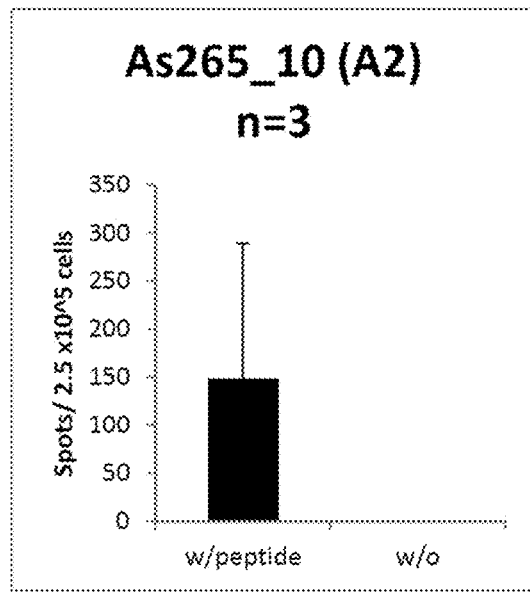
FIG. 28 shows the result of evaluation of in vivo CTL inducibility of the peptide represented by SEQ ID No: 20 (As265_10) by means of an interferon-γ ELISPOT assay using an HLA-A*02:01 transgenic mouse. The ordinate, black bar and white bar are the same as those in FIG. 11.
Figure 29:
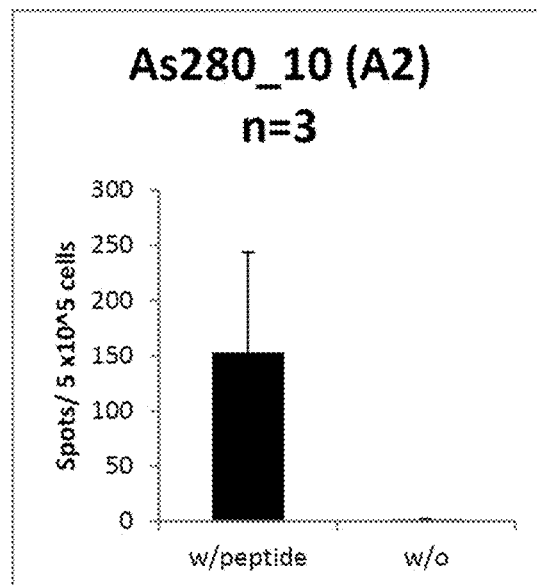
FIG. 29 shows the result of evaluation of in vivo CTL inducibility of the peptide represented by SEQ ID No: 21 (As280_10) by means of an interferon-γ ELISPOT assay using an HLA-A*02:01 transgenic mouse. The ordinate, black bar and white bar are the same as those in FIG. 11.
Figure 30:
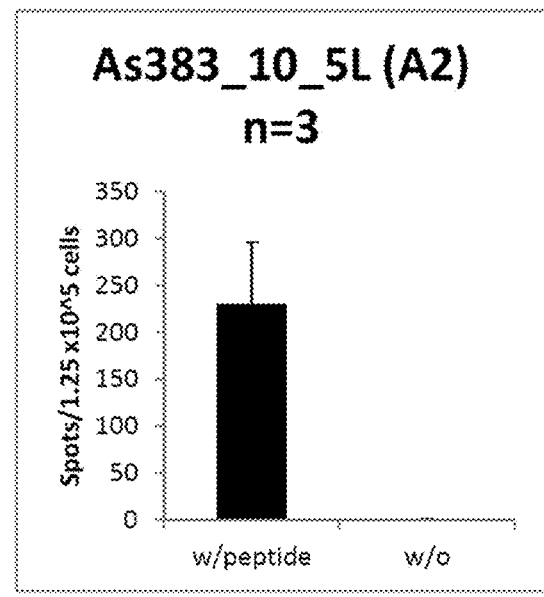
FIG. 30 shows the result of evaluation of in vivo CTL inducibility of the peptide represented by SEQ ID No: 22 (As383_10_5L) by means of an interferon-γ ELISPOT assay using an HLA-A*02:01 transgenic mouse. The ordinate, black bar and white bar are the same as those in FIG. 11.
Figure 31:
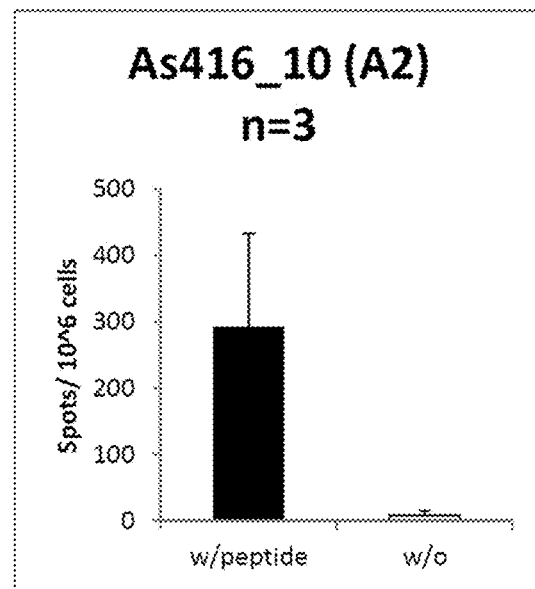
FIG. 31 shows the result of evaluation of in vivo CTL inducibility of the peptide represented by SEQ ID No: 23 (As416_10) by means of an interferon-γ ELISPOT assay using an HLA-A*02:01 transgenic mouse. The ordinate, black bar and white bar are the same as those in FIG. 11.
Figure 32:
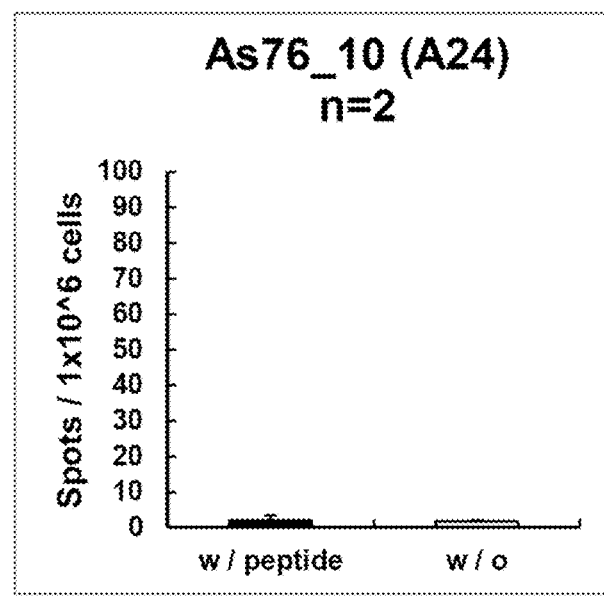
FIG. 32 shows the result of evaluation of in vivo CTL inducibility of the peptide represented by SEQ ID No: 24 (As76_10) by means of an interferon-γ ELISPOT assay using an HLA-A*24:02 transgenic mouse. The ordinate, black bar and white bar are the same as those in FIG. 11.
Figure 33:
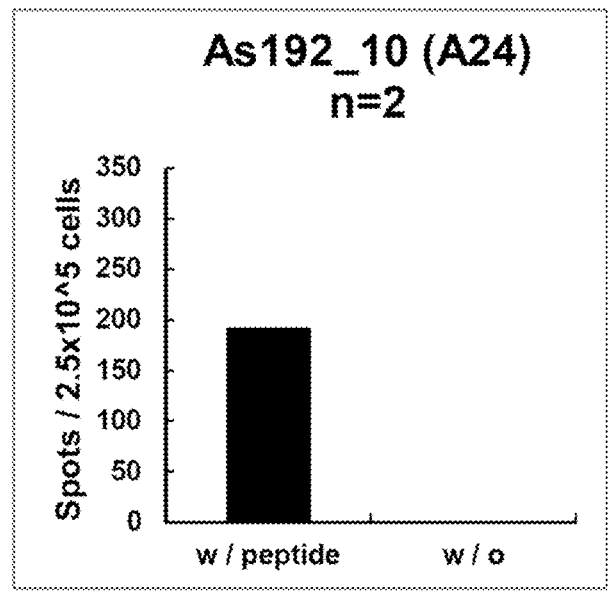
FIG. 33 shows the result of evaluation of in vivo CTL inducibility of the peptide represented by SEQ ID No: 25 (As192_10) by means of an interferon-γ ELISPOT assay using an HLA-A*24:02 transgenic mouse. The ordinate, black bar and white bar are the same as those in FIG. 11.
Figure 34:
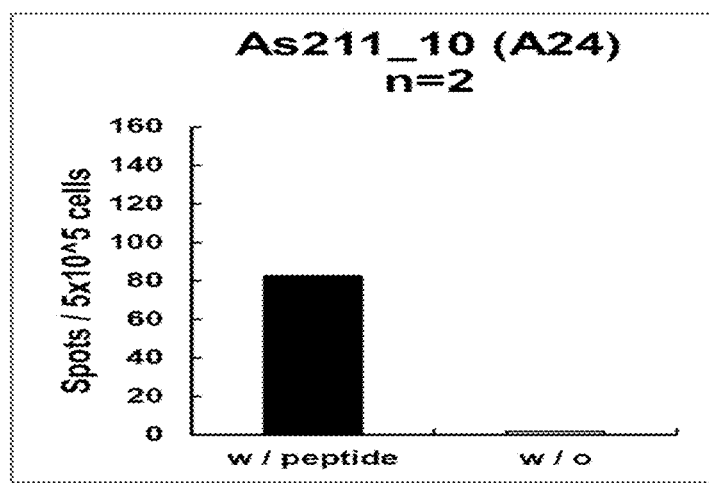
FIG. 34 shows the result of evaluation of in vivo CTL inducibility of the peptide represented by SEQ ID No: 26 (As211_10) by means of an interferon-γ ELISPOT assay using an HLA-A*24:02 transgenic mouse. The ordinate, black bar and white bar are the same as those in FIG. 11.
Figure 35:
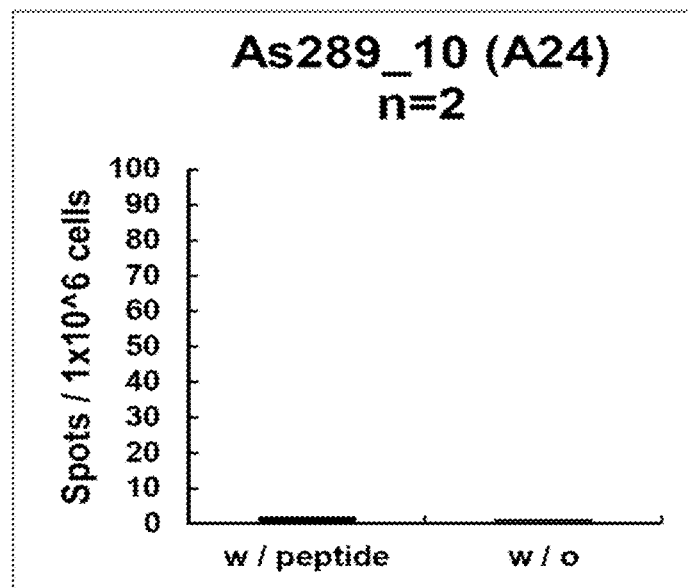
FIG. 35 shows the result of evaluation of in vivo CTL inducibility of the peptide represented by SEQ ID No: 27 (As289_10) by means of an interferon-γ ELISPOT assay using an HLA-A*24:02 transgenic mouse. The ordinate, black bar and white bar are the same as those in FIG. 11.
Figure 36:
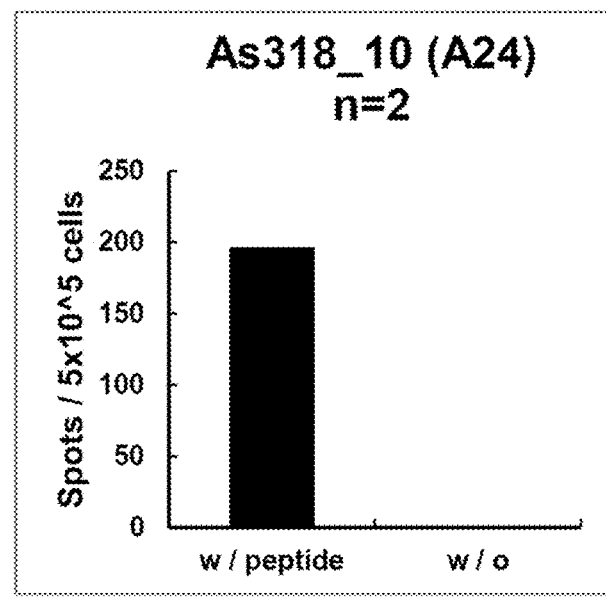
FIG. 36 shows the result of evaluation of in vivo CTL inducibility of the peptide represented by SEQ ID No: 28 (As318_10) by means of an interferon-γ ELISPOT assay using an HLA-A*24:02 transgenic mouse. The ordinate, black bar and white bar are the same as those in FIG. 11.
Figure 37:
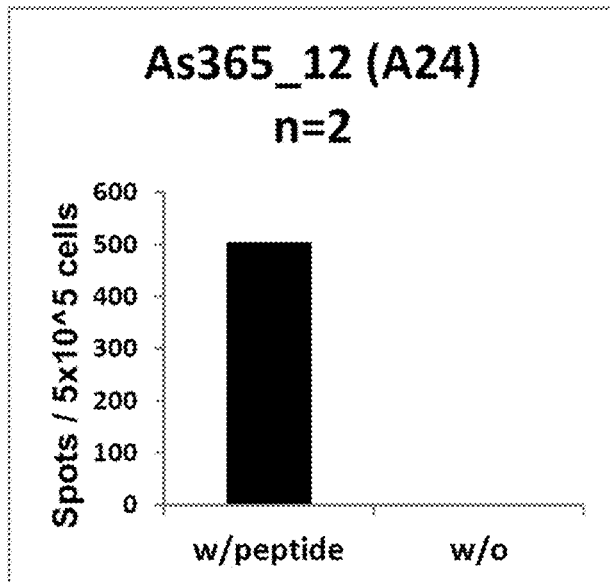
FIG. 37 shows the result of evaluation of in vivo CTL inducibility of the peptide represented by SEQ ID No: 29 (As365_12) by means of an interferon-γ ELISPOT assay using an HLA-A*24:02 transgenic mouse. The ordinate, black bar and white bar are the same as those in FIG. 11.
Figure 38:
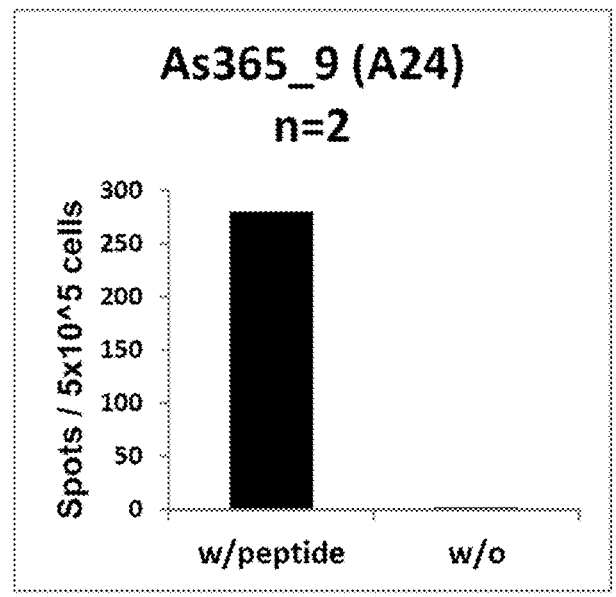
FIG. 38 shows the result of evaluation of in vivo CTL inducibility of the peptide represented by SEQ ID No: 30 (As365_9) by means of an interferon-γ ELISPOT assay using an HLA-A*24:02 transgenic mouse. The ordinate, black bar and white bar are the same as those in FIG. 11.
Figure 39:
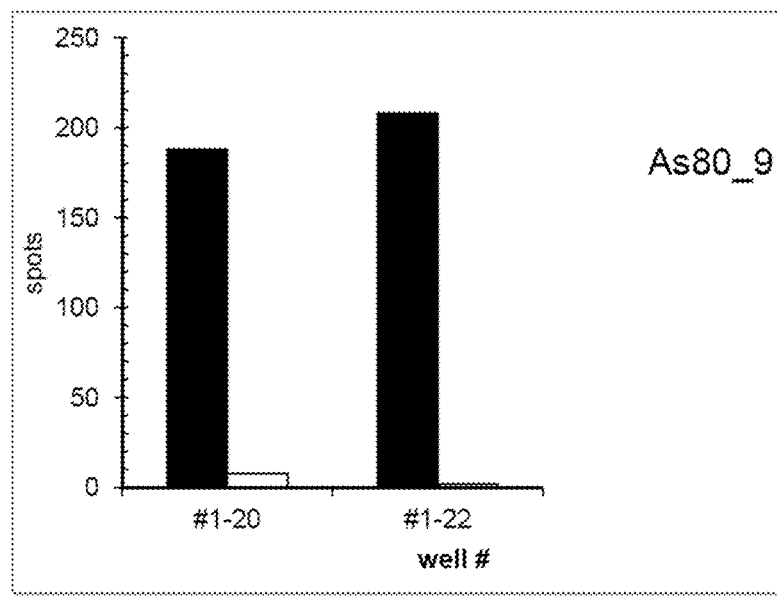
FIG. 39 shows the result of evaluation of in vivo CTL inducibility of the peptide represented by SEQ ID No: 4 (As80_9) by means of an interferon-γ ELISPOT assay using peripheral blood mononuclear cells derived from a HLA-A*02:01-positive healthy individual. The ordinate denotes the number of spots per number of seeded cells (approximately $1\times10^5$). The black bar ('w/peptide') and the white bar ('w/o') show the results of stimulation culturing in the presence or absence of peptide, respectively. That is, the differences in the figures between the black bar and the white bar denote the number of peptide-specific CTLs induced by administration of each of the peptides.
Figure 40:
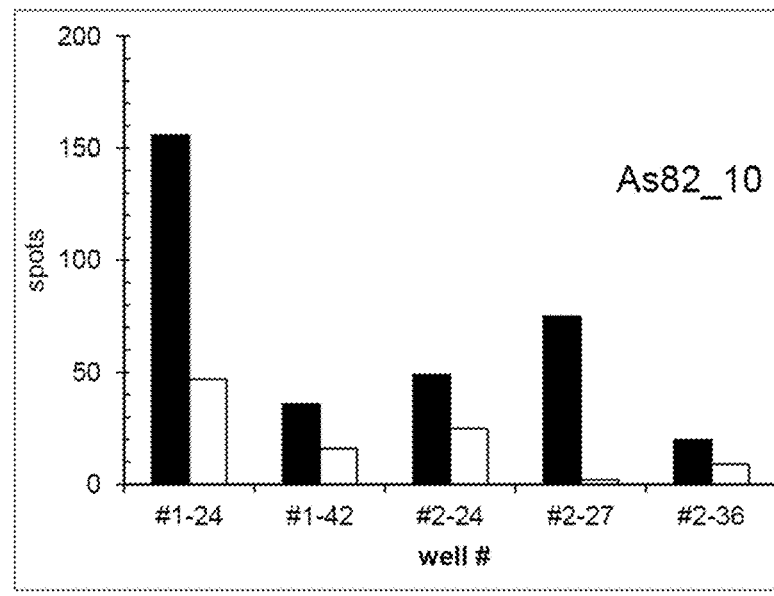
FIG. 40 shows the result of evaluation of in vivo CTL inducibility of the peptide represented by SEQ ID No: 5 (As82_10) by means of an interferon-γ ELISPOT assay using peripheral blood mononuclear cells derived from a HLA-A*02:01-positive healthy individual. The ordinate, black bar and white bar are the same as those in FIG. 39.
Figure 41:
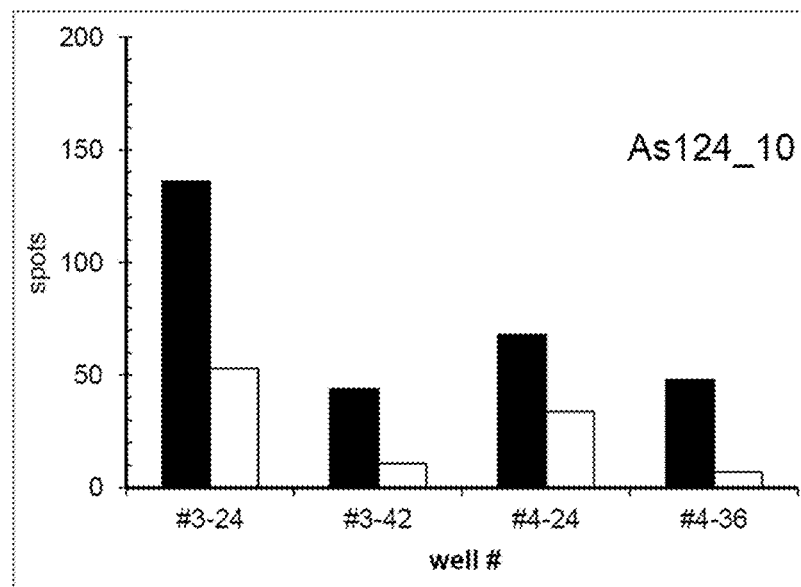
FIG. 41 shows the result of evaluation of in vivo CTL inducibility of the peptide represented by SEQ ID No: 6 (As124_10) by means of an interferon-γ ELISPOT assay using peripheral blood mononuclear cells derived from a HLA-A*02:01-positive healthy individual. The ordinate, black bar and white bar are the same as those in FIG. 39.
Figure 42:
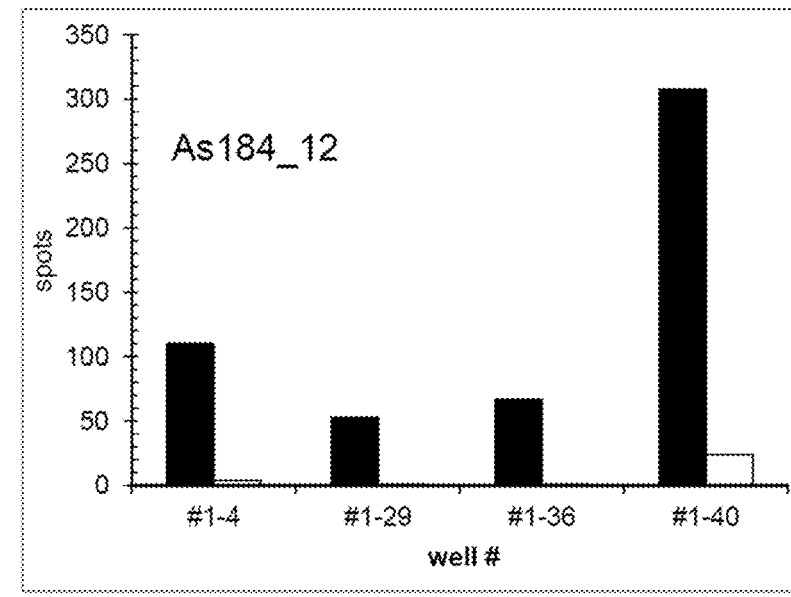
FIG. 42 shows the result of evaluation of in vivo CTL inducibility of the peptide represented by SEQ ID No: 8 (As184_12) by means of an interferon-γ ELISPOT assay using peripheral blood mononuclear cells derived from a HLA-A*02:01-positive healthy individual. The ordinate, black bar and white bar are the same as those in FIG. 39.
Figure 43:
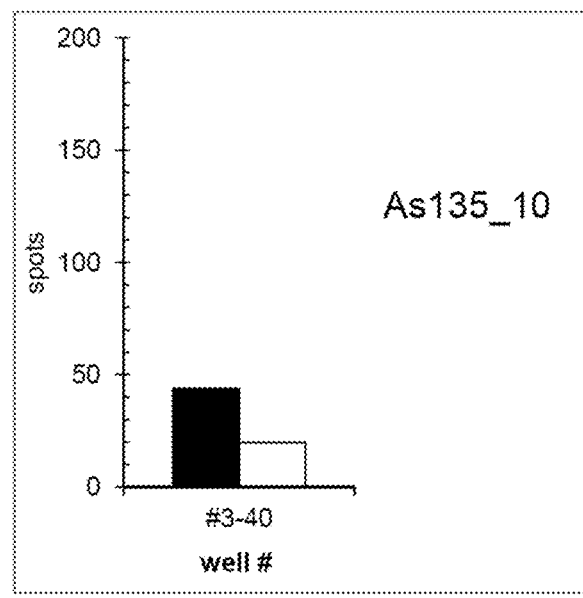
FIG. 43 shows the result of evaluation of in vivo CTL inducibility of the peptide represented by SEQ ID No: 9 (As135_10) by means of an interferon-γ ELISPOT assay using peripheral blood mononuclear cells derived from a HLA-A*02:01-positive healthy individual. The ordinate, black bar and white bar are the same as those in FIG. 39.

As shown in FIG. 10, the CTLs showed high cytotoxic activity toward [3] IV9 peptide pulse group compared with [1] no peptide pulse group, [2] HIV peptide pulse group, and IV9 peptide-pulsed K562 group. This suggests that the CTLs showed specific cytotoxic activity toward the ASB4 peptide. In addition, the SW480-SP group showed a similar cytotoxic activity as [3] IV9 peptide pulse group even without a peptide pulse, while the SW480-MP group showed only a similar cytotoxic activity as [1] no peptide pulse group and [2] HIV peptide pulse group. This suggests that the SW480 cell line presents the IV9 peptide as an antigen on the cell surface only in the SP fractionated cells.

Experimental Example 9: ASB4-Derived Peptide Having HLA-A*02:01 and HLA-A*24:02 Binding Motif ASB4-derived peptides (peptides described in SEQ ID Nos: 4 to 46) for which binding to HLA-A*02:01 and/or HLA-A*24:02 is predicted were extracted using BIMAS (bimas.cit.nih.gov/molbio/hla_bind/), SYFPEITHI (syfpeithi.de/), and IEDB (MHC-I processing predictions; iedb.org/), etc. which are programs for predicting binding between an MHC and a peptide. These peptides were chemically synthesized by the Fmoc method. The peptides thus synthesized are shown in Table 4 below. 'Start' denotes the amino acid position in ASB4 (SEQ ID No: 2) of the N terminal amino acid of the synthesized peptide, and 'End' denotes the amino acid position in ASB4 (SEQ ID No: 2) of the C terminal amino acid of the synthesized peptide. 'Length' denotes the number of amino acids of the synthesized peptide.

TABLE 4

Synthesized peptide

| SEQ ID No. | Name | Start | End | Length | Peptide sequence |
| --- | --- | --- | --- | --- | --- |
| 4 | As80_9 | 80 | 88 | 9 | HLSVLFGHV |
| 5 | As82_10 | 82 | 91 | 10 | SVLFGHVECL |
| 6 | As124_10 | 124 | 133 | 10 | KILCDRGAKL |
| 7 | As125_9 | 125 | 133 | 9 | ILCDRGAKL |
| 8 | As184_12 | 184 | 195 | 12 | HFGLSELVAFYV |
| 9 | As135_10 | 135 | 144 | 10 | CYSLSGHTAL |
| 10 | As83_10 | 83 | 92 | 10 | VLFGHVECLL |
| 11 | As87_9 | 87 | 95 | 9 | HVECLLVLL |
| 12 | As307_10 | 307 | 316 | 10 | CYQLLLNHGA |
| 13 | As301_11 | 301 | 311 | 11 | AAQPEICYQLL |
| 14 | As405_9 | 405 | 413 | 9 | PLLSLPLSL |
| 15 | As35_10 | 35 | 44 | 10 | AILIQRQIDV |
| 16 | As92_10 | 92 | 101 | 10 | LVLLDHNATI |
| 17 | As152_9 | 152 | 160 | 9 | SILCAKQLV |
| 18 | As186_10 | 186 | 195 | 10 | GLSELVAFYV |
| 19 | As236_10 | 236 | 245 | 10 | RMLLDYKAEV |
| 20 | As265_10 | 265 | 274 | 10 | HVLMHMMLEA |
| 21 | As280_10 | 280 | 289 | 10 | LMDINGCAAI |
| 22 | As383_10_5L | 383 | 392 | 10 | TLMHLSRCAI |
| 23 | As416_10 | 416 | 425 | 10 | YLLLEPEGII |
| 24 | As76_10 | 76 | 85 | 10 | ATGLHLSVLF |
| 25 | As192_10 | 192 | 201 | 10 | AFYVEHGAIF |
| 26 | As211_10 | 211 | 220 | 10 | PLAIAAYWAL |
| 27 | As289_10 | 289 | 298 | 10 | IQYVLKVTSV |
| 28 | As318_10 | 318 | 327 | 10 | RIYPPQFHKV |
| 3 | IV9 | 319 | 327 | 9 | IYPPQFHKV |
| 29 | As365_12 | 365 | 376 | 12 | KYWDFYHSLFTV |
| 30 | As365_9 | 365 | 373 | 9 | KYWDFYHSL |
| 31 | As15_11 | 15 | 25 | 11 | KLVKRNFLEAL |
| 32 | As29_9 | 29 | 37 | 9 | DFGKLKAIL |
| 33 | As41_10 | 41 | 30 | 10 | QIDVDTVFEV |
| 34 | As48_10 | 48 | 57 | 10 | FEVEDENMVL |
| 35 | As63_9 | 63 | 71 | 9 | GYWLPSYKL |
| 36 | As70_10 | 70 | 79 | 10 | KLKSSWATGL |
| 37 | As145_10 | 145 | 154 | 10 | HFCTTPSSIL |
| 38 | As157_10 | 157 | 166 | 10 | KQLVWRGANV |
| 39 | As271_10 | 271 | 280 | 10 | MLEAGAEANL |
| 40 | As290_9 | 290 | 298 | 9 | QYVLKVTSV |

TABLE 4-continued

Synthesized peptide

| SEQ ID No. | Name | Start | End | Length | Peptide sequence |
|---|---|---|---|---|---|
| 41 | As310_10 | 310 | 319 | 10 | LLLNHGAARI |
| 42 | As311_9 | 311 | 319 | 9 | LLNHGAARI |
| 43 | As340_9 | 340 | 348 | 9 | VVVNAYEHI |
| 44 | As368_9 | 368 | 376 | 9 | DFYHSLFTV |
| 45 | As403_9 | 403 | 411 | 9 | AIPLLSLPL |
| 46 | As408_10 | 408 | 417 | 10 | SLPLSLKKYL |

Example 10: Evaluation of Binding of ASB4-Derived Peptide to HLA-a*02:01 or HLA-A*24:02

Evaluation of the binding of an ASB4-derived peptide to each HLA molecule was carried out by an MHC class I expression stabilization test. In this test, T2-A24 cells, which are a human lymphoblastoid cell line, were used. T2 cells are deficient in the transporter associated with antigen processing (TAP), which is involved in the transport of a peptide from the cytoplasm to the endoplasmic reticulum. It is known that an MHC class I molecule (HLA-A*02:01 and HLA-A*24:02) has an unstable structure in a state in which a peptide is not bound (empty MHC class I). T2 cells can usually only express a low level of empty MHC class I molecules on the cell surface. However, when a peptide that can bind to the MHC class I molecule is added, the empty MHC class I molecule binds to the peptide and can be present on the cell surface in a stable manner. Therefore, the cell surface MHC class I expression level depends on the MHC class I binding affinity of a peptide.

The T2-A24 cells were subcultured at 37° C. under 5% $CO_2$. With regard to peptides, ASB4-derived peptides (the peptides listed in Table 4), Melan A A27L peptide (amino acid sequence: ELAGIGILTV; SEQ ID No: 47) as an HLA-A02-positive control, $HIV_{584-592}$ peptide (amino acid sequence: RYLRDQQLL; SEQ ID No: 48) as an HLA-A24-positive control, $MAGE-1_{161-169}$ peptide (amino acid sequence: EADPTGHSY; SEQ ID No: 49) as an HLA-A02-negative control, and $VSV_{52-59}$ peptide (amino acid sequence: RGYVYQGL; SEQ ID No: 50) as an HLA-A24-negative control were each evaluated in terms of binding at a concentration of 100 μg/mL. These peptides were dissolved in DMSO and further diluted by 200 times with RPMI 160 medium. A cell suspension and the peptide solution were mixed and cultured under conditions of 5% $CO_2$ and 26° C. for 16 to 18 hours. Co-culturing was carried out at a temperature of 37° C. for a further 3 hours, the supernatant was then removed by centrifuging, and cells were isolated. The isolated cells were washed with 3% FBS-containing PBS, an anti-HLA-A02 antibody (clone: BB7.2; Medical & Biological Laboratories Co., Ltd.) or anti-HLA-A24 antibody (clone: 17A10; Medical & Biological Laboratories Co., Ltd.) fluorescently-labeled with FITC was added, and the mixture was allowed to stand at room temperature for 30 minutes. Subsequently, the cells were washed with 3% FBS-containing PBS, 4% paraformaldehyde phosphate buffer was added, and the mixture was allowed to stand at room temperature for 10 minutes to thus fix the cells. The fixed cells were subjected to measurement of FITC fluorescence intensity by a flow cytometer (FAC-Scan). The mean fluorescence intensity (MFI) was calculated as a solvent ratio.

The results of the HLA-binding test are shown in Table 5. As shown in Table 5, the MFI of peptides described in SEQ ID Nos: 4 to 23 with respect to HLA-A*02:01 was at least 1.5, the MFI of peptides described in SEQ ID Nos: 3 to 14 and 24 to 30 with respect to HLA-A*24:02 was at least 1.5, and the MFI of peptides described in SEQ ID Nos: 4 to 14 with respect to both HLA-A*02:01 and HLA-A*24:02 was at least 1.5.

TABLE 5

Results of HLA binding test

| | HLA-A*02:01 | | HLA-A*24:02 | | MFI | |
|---|---|---|---|---|---|---|
| SEQ ID No. | Positive control | Negative control | Positive control | Negative control | HLA-A02 | HLA-A24 |
| 4 | 3.3 | 1.0 | 3.3 | 1.0 | 1.6 | 2.1 |
| 5 | 3.3 | 1.0 | 3.3 | 1.0 | 3.3 | 2.7 |
| 6 | 3.3 | 1.0 | 3.3 | 1.0 | 1.6 | 2.2 |
| 7 | 3.5 | 1.0 | 2.6 | 1.0 | 1.9 | 1.8 |
| 8 | 3.9 | 1.0 | 3.3 | 1.0 | 3.1 | 3.2 |
| 9 | 3.5 | 1.0 | 2.6 | 1.0 | 1.6 | 2.4 |
| 10 | 3.5 | 1.0 | 2.6 | 1.0 | 3.6 | 2.8 |
| 11 | 3.3 | 1.0 | 3.3 | 1.0 | 1.5 | 1.6 |
| 12 | 3.3 | 1.0 | 3.3 | 1.0 | 2.5 | 1.9 |
| 13 | 3.3 | 1.0 | 3.3 | 1.0 | 2.6 | 2.0 |
| 14 | 3.3 | 1.0 | 3.3 | 1.0 | 2.2 | 2.8 |
| 15 | 3.3 | 1.0 | 3.3 | 1.0 | 3.4 | 1.1 |
| 16 | 3.3 | 1.0 | 3.3 | 1.0 | 2.6 | 1.1 |
| 17 | 3.3 | 1.0 | 3.3 | 1.0 | 1.8 | 1.3 |
| 18 | 3.3 | 1.0 | 3.3 | 1.0 | 2.6 | 1.1 |
| 19 | 3.3 | 1.0 | 3.3 | 1.0 | 3.3 | 1.0 |
| 20 | 3.3 | 1.0 | 3.3 | 1.0 | 2.0 | 1.3 |
| 21 | 3.3 | 1.0 | 3.3 | 1.0 | 3.1 | 1.2 |
| 22 | 3.5 | 1.0 | 2.6 | 1.0 | 2.4 | 1.0 |
| 23 | 3.3 | 1.0 | 3.3 | 1.0 | 2.8 | 1.4 |
| 24 | 3.3 | 1.0 | 2.8 | 1.0 | 0.9 | 2.1 |
| 25 | 3.5 | 1.0 | 2.6 | 1.0 | 1.1 | 2.2 |
| 26 | 3.3 | 1.0 | 3.3 | 1.0 | 1.1 | 2.1 |
| 27 | 3.3 | 1.0 | 2.8 | 1.0 | 1.2 | 1.5 |
| 28 | 3.3 | 1.0 | 3.3 | 1.0 | 1.4 | 3.6 |
| 3 | 3.3 | 1.0 | 2.8 | 1.0 | 0.9 | 3.3 |
| 29 | 3.3 | 1.0 | 2.8 | 1.0 | 1.0 | 2.4 |
| 30 | 3.3 | 1.0 | 3.3 | 1.0 | 1.1 | 2.5 |
| 31 | 3.3 | 1.0 | 3.3 | 1.0 | 1.0 | 1.0 |
| 32 | 3.5 | 1.0 | 2.6 | 1.0 | 1.0 | 1.0 |
| 33 | 3.3 | 1.0 | 3.3 | 1.0 | 1.2 | 1.1 |
| 34 | 3.3 | 1.0 | 3.3 | 1.0 | 1.0 | 1.4 |
| 35 | 3.5 | 1.0 | 2.6 | 1.0 | 1.1 | 1.2 |
| 36 | 3.3 | 1.0 | 3.3 | 1.0 | 1.1 | 1.0 |
| 37 | 3.5 | 1.0 | 2.6 | 1.0 | 1.0 | 1.2 |

TABLE 5-continued

Results of HLA binding test

| SEQ ID No. | HLA-A*02:01 Positive control | HLA-A*02:01 Negative control | HLA-A*24:02 Positive control | HLA-A*24:02 Negative control | MFI HLA-A02 | MFI HLA-A24 |
|---|---|---|---|---|---|---|
| 38 | 3.3 | 1.0 | 3.3 | 1.0 | 1.2 | 1.0 |
| 39 | 3.3 | 1.0 | 2.8 | 1.0 | 1.0 | 1.2 |
| 40 | 3.5 | 1.0 | 2.6 | 1.0 | 1.0 | 1.3 |
| 41 | 3.3 | 1.0 | 3.3 | 1.0 | 1.3 | 1.2 |
| 42 | 3.5 | 1.0 | 2.6 | 1.0 | 0.9 | 0.9 |
| 43 | 3.5 | 1.0 | 2.6 | 1.0 | 0.9 | 1.0 |
| 44 | 3.5 | 1.0 | 2.6 | 1.0 | 1.0 | 1.1 |
| 45 | 3.3 | 1.0 | 2.8 | 1.0 | 0.9 | 1.1 |
| 46 | 3.3 | 1.0 | 3.3 | 1.0 | 1.0 | 1.0 |

Example 11: Evaluation of In Vivo CTL Inducibility Using HLA-A*02:01 Transgenic Mouse and HLA-A*24:02 Transgenic Mouse The CTL inducibility of an ASB4-derived peptide that had an MFI with respect to HLA-A*02:01 and/or HLA-A*24:02 of at least 1.5 in Example 10 was evaluated by an in vivo CTL induction test using an HLA-A*02:01 transgenic mouse and/or an HLA-A*24:02 transgenic mouse.

An HLA-A*02:01 transgenic mouse (C57BL/6CrHLA-A2.1DR1) is a mouse that is deficient in mouse MHC and expresses HLA-A*02:01 and HLA-DRB1*01:01, which are human MHCs, and the use of this mouse enables a peptide that can induce CTLs in humans to be selected. Furthermore, an HLA-A*24:02 transgenic mouse is a mouse that expresses HLA-A*24:02, which is a human MHC, and the use of this mouse enables a peptide that can induce CTLs in a human to be selected. Whether or not each peptide has an activity in inducing CTLs was determined by whether or not T cells that can react with the administered peptide are induced by administering the peptide to the mouse.

Specifically, it was carried out as follows. First, the peptide was dissolved in dimethyl sulfoxide at 80 mg/mL, then diluted with water for injection, and mixed with an equal part of incomplete Freund's adjuvant (ISA51VG), thus forming an emulsion. The peptide thus emulsified was administered to the mouse tail base intradermally at two locations at a dose of 250 μg/location. One week after that, the mouse was euthanized with $CO_2$ gas, the spleen was removed, and splenocytes were prepared. For measurement of IFNγ production, an IFNγ ELISPOT assay kit (Becton, Dickinson and Company) was used. On the day before preparing the splenocytes, an ELISPOT plate was treated with an anti-IFNγ antibody, and on the day it was blocked with 10% FBS-containing RPMI 1640 medium. The splenocytes prepared were plated on the blocked ELISPOT plate at 0.25 to $1.0 \times 10^6$ cells/well. The administered ASB4-derived peptide was dissolved in DMSO at 40 mg/mL and further diluted with 10% RPMI 1640 medium to 20 μg/mL. The diluted peptide was added at 50 μL/well to the splenocytes derived from the animal to which the peptide had been administered. In vitro peptide restimulation was applied by culturing the splenocytes to which the peptide was added under 5% $CO_2$ at 37° C. for 16 to 18 hours. After culturing, the supernatant was removed, and the ELISPOT plate was subjected to color development in accordance with the included protocol. The number of color developed spots was measured by KS-ELISPOT.

The results of the IFNγ ELISPOT assay are shown in FIGS. 11 to 38.

It can be seen from the results of this test that, by confirming IFNγ production specific to the peptide in the HLA-A*02:01 transgenic mouse-derived splenocytes, the ASB4-derived peptides represented by SEQ ID Nos: 4 to 12 and 15 to 23 had CTL inducibility. Furthermore, it can be seen that, by confirming IFNγ production specific to the peptide in the HLA-A*24:02 transgenic mouse-derived splenocytes, the ASB4-derived peptides represented by SEQ ID Nos: 4 to 9, 13, 14, 25, 26 and 28 to 30 had CTL inducibility. Therefore, it was shown that each ASB4-derived peptide described in SEQ ID Nos: 4 to 9 had CTL inducibility in both HLA-A02 type and HLA-A24 type subjects.

Example 12: Evaluation of CTL Inducibility Using Human Peripheral Blood Mononuclear Cells With respect to the six types of peptides represented by SEQ ID NOs: 4 to 9, which were confirmed to have CTL inducibility in both HLA-A02 type and HLA-A24 type subjects in Experimental Example 11, whether or not the peptide-specific T cells are induced from human-derived peripheral blood mononuclear cells by stimulation of said peptides was evaluated.

Specifically, peripheral blood mononuclear cells (manufactured by Cellular Technology Limited) derived from HLA-A*02:01-positive or HLA-A*24:02-positive healthy individuals were suspended in an AIM-V medium containing 10% human-derived serum. Subsequently, approximately $1 \times 10^5$ cells were plated in each well of a 96-well U bottom plate, and cultured at 37° C. under 5% $CO_2$. At this time, human IL-2 and peptide were added at 100 U/mL and 20 μg/mL, respectively. The medium was exchanged every 3 or 4 days and an IFNγ ELISPOT assay was carried out after about 2 weeks. On the day before the assay, ELISPOT plates were treated with anti-IFNγ antibody, and on the day of assay, they were blocked with RPMI1640 medium containing 10% fetal calf serum at room temperature for about 2 hours. The human peripheral blood mononuclear cells in the culture were washed with an AIM-V medium containing 10% human-derived serum and plated in each well of the blocked ELISPOT plate. After culturing at 37° C. under 5% $CO_2$ for 16 to 18 hours, the supernatant was removed and the ELISPOT plates were subjected to color development according to the attached protocol. The number of colored spots was measured with an ELISPOT analyzer manufactured by Cellular Technology Limited.

Figure 44:
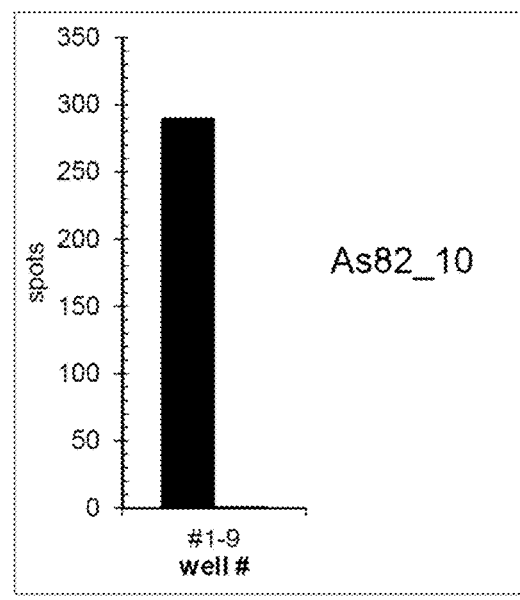
FIG. 44 shows the result of evaluation of in vivo CTL inducibility of the peptide represented by SEQ ID No: 5 (As82_10) by means of an interferon-γ ELISPOT assay using peripheral blood mononuclear cells derived from a HLA-A*24:02-positive healthy individual. The ordinate, black bar and white bar are the same as those in FIG. 39.
Figure 45:
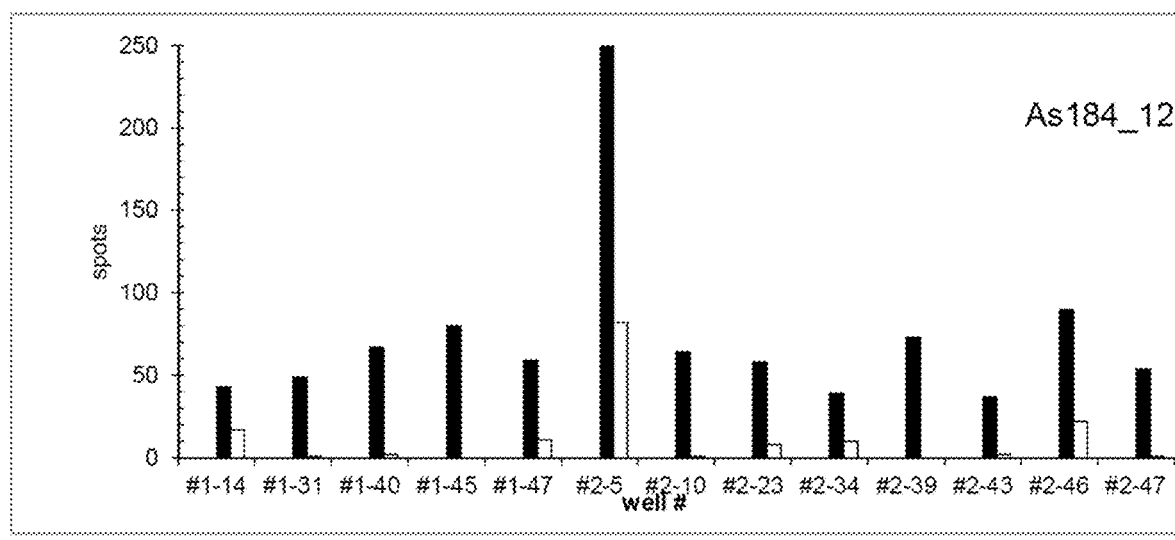
FIG. 45 shows the result of evaluation of in vivo CTL inducibility of the peptide represented by SEQ ID No: 8 (As184_12) by means of an interferon-γ ELISPOT assay using peripheral blood mononuclear cells derived from a HLA-A*24:02-positive healthy individual. The ordinate, black bar and white bar are the same as those in FIG. 39.

The results evaluated for SEQ ID NOs: 4, 5, 6, 8 and 9 using HLA-A*02:01-positive PBMC are shown in FIGS. 39, 40, 41, 42 and 43, and the results evaluated for SEQ ID Nos: 5 and 8 using HLA-A*24:02-positive PBMC are shown in FIGS. 44 and 45. The vertical axis shows the number of spots observed in each well and the horizontal axis shows positive well numbers. In addition, black bars indicate the number of spots detected under peptide stimulation conditions, and white bars indicate the number of spots (controls) detected under no peptide pulse conditions. That is, the difference between the black bar and the white bar shows peptide-specific spots.

As a result of this test, it was found that the peptides represented by SEQ ID NOs: 4, 5, 6, 8 and 9 are able to induce peptide-specific CTLs from peripheral blood mononuclear cells derived from HLA-A*02:01-positive or HLA-A*24:02-positive healthy individuals.

It was also shown that each of the peptides derived from ASB4 represented by SEQ ID NOs: 5 and 8 has CTL inducibility in both HLA-A02 type and HLA-A24 type subjects.

INDUSTRIAL APPLICABILITY

The present invention contributes to the development of a highly effective cancer vaccine by identifying an ASB4-derived natural peptide that is actually subjected to antigen presentation on a cancer stem cell and the CTL induced by the peptide vaccine surely kills cancer cells. Furthermore, since it can be determined from an identified natural peptide specific to a cancer stem cell that ASB4 is specifically expressed in a cancer stem cell, it becomes possible to identify a cancer stem cell using ASB4 as a marker. Moreover, a natural antigen peptide derived from the gene is useful as a preventive and/or therapeutic agent for cancer having a large effect even with a small amount. Furthermore, the present invention provides an ASB4-derived tumor antigen peptide having activity in inducing CTLs, etc. The peptide of the present invention is useful as a preventive and/or therapeutic agent for cancer.

[Table of Sequences] PCT2751DN_ST25.txt

The invention claimed is:

1. An antigen peptide represented by $Y_0$-$X_0$-$Z_0$, wherein $X_0$ is any of (1) to (2) below:
   (1) SEQ ID NO: 3 in which the second amino acid from the N terminal is replaced by leucine, isoleucine or methionine, and/or the amino acid at the C terminal is replaced by leucine or isoleucine; or
   (2) SEQ ID NO: 3 in which the second amino acid from the N terminal is replaced by phenylalanine, methionine or tryptophan, and/or the amino acid at the C terminal is replaced by leucine, isoleucine or phenylalanine; and,
   $Y_0$ and $Z_0$ are mutually independently a peptide consisting of 0 to 5 amino acids.

2. The antigen peptide according to claim 1, wherein $X_0$ consists of an amino acid sequence represented by SEQ ID NO: 3, in which the second amino acid from the N terminal is replaced by methionine, leucine or isoleucine, and/or the amino acid at the C terminal is replaced by leucine or isoleucine; and
   $Y_0$ and $Z_0$ are not present.

3. The antigen peptide according to claim 1, wherein $X_0$ consists of an amino acid sequence represented by SEQ ID NO: 3, in which the second amino acid from the N terminal is replaced by methionine, and/or the amino acid at the C terminal is replaced by leucine, isoleucine or phenylalanine; and
   $Y_0$ and $Z_0$ are not present.

4. An antigen peptide represented by $Y_0$-$X_0$-$Z_0$ wherein $X_0$ consists of an amino acid sequence represented by SEQ ID NO: 3, either one of $Y_0$ or $Z_0$ is one amino acid, and the other is not present, provided that $Y_0$ is not arginine and $Z_0$ is not isoleucine.

5. A polyepitope peptide which comprises a plurality of epitope peptides linked together, wherein the polyepitope peptide comprises at least one antigen peptide according to claim 1 or any of a peptide represented by $Y_0$-$X_0$-$Z_0$, wherein $X_0$ is SEQ ID NO. 3, and $Y_0$ and $Z_0$ are mutually independently a peptide consisting of 0 to 5 amino acids as the epitope peptide.

6. A polynucleotide encoding at least one of the antigen peptide according to claim 1 or claim 4.

7. An expression vector comprising the polynucleotide according to claim 6.

8. A gene transfer composition comprising the expression vector according to claim 7.

9. A pharmaceutical composition comprising as an active ingredient any of (a) to (c) below:
   (a) the antigen peptide according to claim 1 or claim 4,
   (b) a polynucleotide encoding the peptide according to claim 1 or claim 4,
   (c) an expression vector comprising the polynucleotide encoding the peptide according to claim 1 or claim 4.

10. The pharmaceutical composition according to claim 9, wherein the active ingredient is (a) the antigen peptide.

11. The pharmaceutical composition according to claim 9, further comprising an adjuvant.

12. The pharmaceutical composition according to claim 9, wherein the pharmaceutical composition is an agent against recurrence and metastasis of cancer and/or therapeutic agent for cancer.

13. The pharmaceutical composition according to claim 9, wherein the pharmaceutical composition is a vaccine for the prevention of recurrence and metastasis and/or treatment of a cancer.

14. An agent for inducing cytotoxic T cells, the agent comprising as an active ingredient any of (a) to (c) below:
   (a) the antigen peptide according to claim 1 or claim 4,
   (b) a polynucleotide encoding the peptide according to claim 1 or claim 4,
   (c) an expression vector comprising the polynucleotide encoding the peptide according to claim 1 or claim 4.

15. A method for producing an antigen-presenting cell, the method comprising contacting in vitro a cell having an antigen-presenting ability with
   (A) the antigen peptide according to claim 1 or any of a peptide represented by $Y_0$-$X_0$-$Z_0$, wherein $X_0$ is SEQ ID NO. 3, and $Y_0$ and $Z_0$ are mutually independently a peptide consisting of 0 to 5 amino acids, or
   (B) a polynucleotide encoding at least one of the peptide of (A).

16. A method for inducing a cytotoxic T cell, the method comprising contacting in vitro a peripheral blood lymphocyte with
   (A) the antigen peptide according to claim 1 or any of a peptide represented by $Y_0$-$X_0$-$Z_0$, wherein $X_0$ is SEQ ID NO. 3, and $Y_0$ and $Z_0$ are mutually independently a peptide consisting of 0 to 5 amino acids, or
   (B) a polynucleotide encoding at least one of the antigen peptide of (A).

17. An HLA multimer comprising an HLA and the antigen peptide according to claim 1 or claim 4.

18. A diagnostic agent comprising the HLA multimer according to claim 17.

19. The antigen peptide according to claim 1, wherein $X_0$ consists of an amino acid sequence represented by SEQ ID NO: 3, in which the second amino acid from the N terminal is replaced by methionine, leucine or isoleucine, and/or the amino acid at the C terminal is replaced by leucine or isoleucine, either one of $Y_0$ or $Z_0$ is one amino acid, and the other is not present.

20. The antigen peptide according to claim 1, wherein $X_0$ consists of an amino acid sequence represented by SEQ ID NO: 3, in which the second amino acid from the N terminal is replaced by methionine, and/or the amino acid at the C terminal is replaced by leucine, isoleucine or phenylalanine, either one of $Y_0$ or $Z_0$ is one amino acid, and the other is not present.

21. A method for treating a subject having cancer comprising administering to the subject an effective amount of the peptide according to claim 1 or claim 4.

22. A method for treating a subject having cancer comprising administering to the subject an effective amount of the polynucleotide according to claim 6.

23. A method for treating a subject having cancer comprising administering to the subject an effective amount of CTLs induced by the method according to claim 16.

24. A method for treating a subject having cancer comprising administering to the subject an effective amount of antigen presenting cells produced by the method according to claim 15.

25. A pharmaceutical composition comprising as an active ingredient a peptide represented by $Y_0$-$X_0$-$Z_0$, wherein $X_0$ is SEQ ID NO. 3, and $Y_0$ and $Z_0$ are mutually independently a peptide consisting of 0 to 5 amino acids; and an adjuvant.

26. A method for treating a subject having cancer comprising administering to the subject an effective amount of a peptide represented by $Y_0$-$X_0$-$Z_0$, wherein $X_0$ is SEQ ID NO. 3 and $Y_0$ and $Z_0$ are mutually independently a peptide consisting of 0 to 5 amino acids.

27. A method for treating a subject having cancer comprising administering to the subject an effective amount of a polynucleotide encoding a peptide represented by $Y_0$-$X_0$-$Z_0$, wherein $X_0$ is SEQ ID NO. 3 and $Y_0$ and $Z_0$ are mutually independently a peptide consisting of 0 to 5 amino acids.

28. An antigen peptide represented by $Y_0$-$X_0$-$Z_0$, wherein $X_0$ is any of (1) to (2) below:
(1) SEQ ID NO: 28 in which the second amino acid from the N terminal is replaced by leucine or methionine, and/or the amino acid at the C terminal is replaced by leucine or isoleucine;
or
(2) SEQ ID NO: 28 in which the second amino acid from the N terminal is replaced by tyrosine, phenylalanine, methionine or tryptophan, and/or the amino acid at the C terminal is replaced by leucine, isoleucine or phenylalanine; and,
$Y_0$ and $Z_0$ are mutually independently a peptide consisting of 0 to 5 amino acids.

29. An antigen peptide represented by $Y_0$-$X_0$-$Z_0$, wherein $X_0$ is any of (1) to (2) below:
(1) SEQ ID NO: 4 in which the second amino acid from the N terminal is replaced by isoleucine or methionine, and/or the amino acid at the C terminal is replaced by leucine or isoleucine;
or
(2) SEQ ID NO: 4 in which the second amino acid from the N terminal is replaced by tyrosine, phenylalanine, methionine or tryptophan, and/or the amino acid at the C terminal is replaced by leucine, isoleucine or phenylalanine; and,
$Y_0$ and $Z_0$ are mutually independently a peptide consisting of 0 to 5 amino acids.

\* \* \* \* \*

SEQUENCE LISTING

```
<160> NUMBER OF SEQ ID NOS: 56

<210> SEQ ID NO 1
<211> LENGTH: 1281
<212> TYPE: DNA
<213> ORGANISM: Homo sapiens

<400> SEQUENCE: 1
atggacggca ccactgcccc tgtcactaaa tctggagctg ccaagttagt taagagaaat      60
ttccttgagg cgctaaagtc caatgacttc ggaaaattga aggctatttt gatccaaagg     120
caaatagatg tggacactgt ttttgaagtc gaagatgaga atatggtttt ggcatcttat     180
aaacaaggtt actggttgcc tagctataaa ttgaagtctt cctgggccac aggcctccat     240
ctctctgtct tgtttggcca tgtggaatgt cttctggtgc tactggacca caatgctaca     300
atcaactgta gacccaatgg gaaaacccct cttcacgtgg cttgtgaaat ggccaatgtg     360
gattgtgtta agatcctctg tgatcgtggg gcaaagctca attgctactc cttaagtgga     420
cacacagctt tgcacttttg tacaactcca agttccattc tctgtgccaa gcaattggtt     480
tggagagggg cgaatgtgaa catgaagacc aacaaccaag atgaggagac gcccttgcac     540
acggctgccc acttcggcct ttcggagctg gtggccttct acgtgaaaca cggggccata     600
gtggacagcg tgaatgccca catggagacc ccctggcca tcgccgccta ctgggccctc     660
cgctttaagg agcaggagta cagcacggag caccacctgg tctgccgcat gctgcttgac     720
tacaaagccg aagtcaatgc cgagatgac gactttaaat ctcccctcca caaggcagcc     780
tggaactgtg accacgtgct catgcacatg atgctggaag ctggcgccga agccaatctc     840
atggatatca acggctgtgc tgccatccag tacgtgctga aggtcacctc cgtgcgccct     900
gctgcccagc tgagatctg ctaccagctc ctgttgaacc atggggctgc ccgaatatac     960
cctccacagt tccataaggt gatacaggcc tgccattctt gtcctaaagc aattgaagtt    1020
gtagtcaatg cctatgaaca catcagatgg aacacaaagt ggagaagagc tatcccccgat    1080 gatgacttgg agaaatactg ggattttttac cactctctct ttactgtgtg ctgtaactct    1140
ccaaggactc tcatgcactt atcgagatgt gccattagaa gaacattaca caacagatgc    1200
catagagcaa ttcctttgct ttccctccca ttgtcattga aaaagtactt gcttttagag    1260
ccagagggaa ttatttatta a                                              1281

<210> SEQ ID NO 2
<211> LENGTH: 426
<212> TYPE: PRT
<213> ORGANISM: Homo sapiens

<400> SEQUENCE: 2

Met Asp Gly Thr Thr Ala Pro Val Thr Lys Ser Gly Ala Ala Lys Leu
```

-continued

```
1               5                   10                  15
Val Lys Arg Asn Phe Leu Glu Ala Leu Lys Ser Asn Asp Phe Gly Lys
                20                  25                  30

Leu Lys Ala Ile Leu Ile Gln Arg Gln Ile Asp Val Asp Thr Val Phe
                35                  40                  45

Glu Val Glu Asp Glu Asn Met Val Leu Ala Ser Tyr Lys Gln Gly Tyr
    50                  55                  60

Trp Leu Pro Ser Tyr Lys Leu Lys Ser Ser Trp Ala Thr Gly Leu His
65                  70                  75                  80

Leu Ser Val Leu Phe Gly His Val Glu Cys Leu Leu Val Leu Leu Asp
                85                  90                  95

His Asn Ala Thr Ile Asn Cys Arg Pro Asn Gly Lys Thr Pro Leu His
                100                 105                 110

Val Ala Cys Glu Met Ala Asn Val Asp Cys Val Lys Ile Leu Cys Asp
                115                 120                 125

Arg Gly Ala Lys Leu Asn Cys Tyr Ser Leu Ser Gly His Thr Ala Leu
            130                 135                 140

His Phe Cys Thr Thr Pro Ser Ser Ile Leu Cys Ala Lys Gln Leu Val
145                 150                 155                 160

Trp Arg Gly Ala Asn Val Asn Met Lys Thr Asn Asn Gln Asp Glu Glu
                165                 170                 175

Thr Pro Leu His Thr Ala His Phe Gly Leu Ser Glu Leu Val Ala
                180                 185                 190

Phe Tyr Val Glu His Gly Ala Ile Val Asp Ser Val Asn Ala His Met
            195                 200                 205

Glu Thr Pro Leu Ala Ile Ala Ala Tyr Trp Ala Leu Arg Phe Lys Glu
    210                 215                 220

Gln Glu Tyr Ser Thr Glu His His Leu Val Cys Arg Met Leu Leu Asp
225                 230                 235                 240

Tyr Lys Ala Glu Val Asn Ala Arg Asp Asp Phe Lys Ser Pro Leu
                245                 250                 255

His Lys Ala Ala Trp Asn Cys Asp His Val Leu Met His Met Met Leu
                260                 265                 270

Glu Ala Gly Ala Glu Ala Asn Leu Met Asp Ile Asn Gly Cys Ala Ala
            275                 280                 285

Ile Gln Tyr Val Leu Lys Val Thr Ser Val Arg Pro Ala Ala Gln Pro
290                 295                 300

Glu Ile Cys Tyr Gln Leu Leu Leu Asn His Gly Ala Ala Arg Ile Tyr
305                 310                 315                 320

Pro Pro Gln Phe His Lys Val Ile Gln Ala Cys His Ser Cys Pro Lys
                325                 330                 335

Ala Ile Glu Val Val Asn Ala Tyr Glu His Ile Arg Trp Asn Thr
            340                 345                 350

Lys Trp Arg Arg Ala Ile Pro Asp Asp Asp Leu Glu Lys Tyr Trp Asp
            355                 360                 365

Phe Tyr His Ser Leu Phe Thr Val Cys Cys Asn Ser Pro Arg Thr Leu
                370                 375                 380

Met His Leu Ser Arg Cys Ala Ile Arg Arg Thr Leu His Asn Arg Cys
385                 390                 395                 400

His Arg Ala Ile Pro Leu Leu Ser Leu Pro Leu Ser Leu Lys Lys Tyr
                405                 410                 415

Leu Leu Leu Glu Pro Glu Gly Ile Ile Tyr
                420                 425
```

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Ile Tyr Pro Pro Gln Phe His Lys Val
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

His Leu Ser Val Leu Phe Gly His Val
1               5

<210> SEQ ID NO 5
<211> LENGTH: 10
<212> TYPE: PRT
<213> ORGANISM: Artificial Sequence
<220> FEATURE:
<223> OTHER INFORMATION: synthetic peptide

<400> SEQUENCE: 5

Ser Val Leu Phe Gly His Val Glu Cys Leu
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic peptide

<400> SEQUENCE: 6

Lys Ile Leu Cys Asp Arg Gly Ala Lys Leu
1               5                   10

<210> SEQ ID NO 7
<211> LENGTH: 9
<212> TYPE: PRT
<213> ORGANISM: Artificial Sequence
<220> FEATURE:
<223> OTHER INFORMATION: synthetic peptide

<400> SEQUENCE: 7

Ile Leu Cys Asp Arg Gly Ala Lys Leu
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic peptide

<400> SEQUENCE: 8

His Phe Gly Leu Ser Glu Leu Val Ala Phe Tyr Val
1               5                   10

```
<210> SEQ ID NO 9
<211> LENGTH: 10
<212> TYPE: PRT
<213> ORGANISM: Artificial Sequence
<220> FEATURE:
<223> OTHER INFORMATION: synthetic peptide

<400> SEQUENCE: 9

Cys Tyr Ser Leu Ser Gly His Thr Ala Leu
1               5                   10

<210> SEQ ID NO 10
<211> LENGTH: 10
<212> TYPE: PRT
<213> ORGANISM: Artificial Sequence
<220> FEATURE:
<223> OTHER INFORMATION: synthetic peptide

<400> SEQUENCE: 10

Val Leu Phe Gly His Val Glu Cys Leu Leu
1               5                   10

<210> SEQ ID NO 11
<211> LENGTH: 9
<212> TYPE: PRT
<213> ORGANISM: Artificial Sequence
<220> FEATURE:
<223> OTHER INFORMATION: synthetic peptide

<400> SEQUENCE: 11

His Val Glu Cys Leu Leu Val Leu Leu
1               5

<210> SEQ ID NO 12
<211> LENGTH: 10
<212> TYPE: PRT
<213> ORGANISM: Artificial Sequence
<220> FEATURE:
<223> OTHER INFORMATION: synthetic peptide

<400> SEQUENCE: 12

Cys Tyr Gln Leu Leu Leu Asn His Gly Ala
1               5                   10

<210> SEQ ID NO 13
<211> LENGTH: 11
<212> TYPE: PRT
<213> ORGANISM: Artificial Sequence
<220> FEATURE:
<223> OTHER INFORMATION: synthetic peptide

<400> SEQUENCE: 13

Ala Ala Gln Pro Glu Ile Cys Tyr Gln Leu Leu
1               5                   10

<210> SEQ ID NO 14
<211> LENGTH: 9
<212> TYPE: PRT
<213> ORGANISM: Artificial Sequence
<220> FEATURE:
<223> OTHER INFORMATION: synthetic peptide

<400> SEQUENCE: 14

Pro Leu Leu Ser Leu Pro Leu Ser Leu
1               5
```

```
<210> SEQ ID NO 15
<211> LENGTH: 10
<212> TYPE: PRT
<213> ORGANISM: Artificial Sequence
<220> FEATURE:
<223> OTHER INFORMATION: synthetic peptide

<400> SEQUENCE: 15

Ala Ile Leu Ile Gln Arg Gln Ile Asp Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: synthetic peptide

<400> SEQUENCE: 16

Leu Val Leu Leu Asp His Asn Ala Thr Ile
1               5                   10

<210> SEQ ID NO 17
<211> LENGTH: 9
<212> TYPE: PRT
<213> ORGANISM: Artificial Sequence
<220> FEATURE:
<223> OTHER INFORMATION: synthetic peptide

<400> SEQUENCE: 17

Ser Ile Leu Cys Ala Lys Gln Leu Val
1               5

<210> SEQ ID NO 18
<211> LENGTH: 10
<212> TYPE: PRT
<213> ORGANISM: Artificial Sequence
<220> FEATURE:
<223> OTHER INFORMATION: synthetic peptide

<400> SEQUENCE: 18

Gly Leu Ser Glu Leu Val Ala Phe Tyr Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: synthetic peptide

<400> SEQUENCE: 19

Arg Met Leu Leu Asp Tyr Lys Ala Glu Val
1               5                   10

<210> SEQ ID NO 20
<211> LENGTH: 10
<212> TYPE: PRT
<213> ORGANISM: Artificial Sequence
<220> FEATURE:
<223> OTHER INFORMATION: synthetic peptide

<400> SEQUENCE: 20

His Val Leu Met His Met Met Leu Glu Ala
1               5                   10

<210> SEQ ID NO 21
```

```
<211> LENGTH: 10
<212> TYPE: PRT
<213> ORGANISM: Artificial Sequence
<220> FEATURE:
<223> OTHER INFORMATION: synthetic peptide

<400> SEQUENCE: 21

Leu Met Asp Ile Asn Gly Cys Ala Ala Ile
1               5                   10

<210> SEQ ID NO 22
<211> LENGTH: 10
<212> TYPE: PRT
<213> ORGANISM: Artificial Sequence
<220> FEATURE:
<223> OTHER INFORMATION: synthetic peptide

<400> SEQUENCE: 22

Thr Leu Met His Leu Ser Arg Cys Ala Ile
1               5                   10

<210> SEQ ID NO 23
<211> LENGTH: 10
<212> TYPE: PRT
<213> ORGANISM: Artificial Sequence
<220> FEATURE:
<223> OTHER INFORMATION: synthetic peptide

<400> SEQUENCE: 23

Tyr Leu Leu Leu Glu Pro Glu Gly Ile Ile
1               5                   10

<210> SEQ ID NO 24
<211> LENGTH: 10
<212> TYPE: PRT
<213> ORGANISM: Artificial Sequence
<220> FEATURE:
<223> OTHER INFORMATION: synthetic peptide

<400> SEQUENCE: 24

Ala Thr Gly Leu His Leu Ser Val Leu Phe
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic peptide

<400> SEQUENCE: 25

Ala Phe Tyr Val Glu His Gly Ala Ile Phe
1               5                   10

<210> SEQ ID NO 26
<211> LENGTH: 10
<212> TYPE: PRT
<213> ORGANISM: Artificial Sequence
<220> FEATURE:
<223> OTHER INFORMATION: synthetic peptide

<400> SEQUENCE: 26

Pro Leu Ala Ile Ala Ala Tyr Trp Ala Leu
1               5                   10

<210> SEQ ID NO 27
<211> LENGTH: 10
```

<212> TYPE: PRT
<213> ORGANISM: Artificial Sequence
<220> FEATURE:
<223> OTHER INFORMATION: synthetic peptide

<400> SEQUENCE: 27

Ile Gln Tyr Val Leu Lys Val Thr Ser Val
1               5                   10

<210> SEQ ID NO 28
<211> LENGTH: 10
<212> TYPE: PRT
<213> ORGANISM: Artificial Sequence
<220> FEATURE:
<223> OTHER INFORMATION: synthetic peptide

<400> SEQUENCE: 28

Arg Ile Tyr Pro Pro Gln Phe His Lys Val
1               5                   10

<210> SEQ ID NO 29
<211> LENGTH: 12
<212> TYPE: PRT
<213> ORGANISM: Artificial Sequence
<220> FEATURE:
<223> OTHER INFORMATION: synthetic peptide

<400> SEQUENCE: 29

Lys Tyr Trp Asp Phe Tyr His Ser Leu Phe Thr Val
1               5                   10

<210> SEQ ID NO 30
<211> LENGTH: 9
<212> TYPE: PRT
<213> ORGANISM: Artificial Sequence
<220> FEATURE:
<223> OTHER INFORMATION: synthetic peptide

<400> SEQUENCE: 30

Lys Tyr Trp Asp Phe Tyr His Ser Leu
1               5

<210> SEQ ID NO 31
<211> LENGTH: 11
<212> TYPE: PRT
<213> ORGANISM: Artificial Sequence
<220> FEATURE:
<223> OTHER INFORMATION: synthetic peptide

<400> SEQUENCE: 31

Lys Leu Val Lys Arg Asn Phe Leu Glu Ala Leu
1               5                   10

<210> SEQ ID NO 32
<211> LENGTH: 9
<212> TYPE: PRT
<213> ORGANISM: Artificial Sequence
<220> FEATURE:
<223> OTHER INFORMATION: synthetic peptide

<400> SEQUENCE: 32

Asp Phe Gly Lys Leu Lys Ala Ile Leu
1               5

<210> SEQ ID NO 33
<211> LENGTH: 10
<212> TYPE: PRT

```
<213> ORGANISM: Artificial Sequence
<220> FEATURE:
<223> OTHER INFORMATION: synthetic peptide

<400> SEQUENCE: 33

Gln Ile Asp Val Asp Thr Val Phe Glu Val
1               5                   10

<210> SEQ ID NO 34
<211> LENGTH: 10
<212> TYPE: PRT
<213> ORGANISM: Artificial Sequence
<220> FEATURE:
<223> OTHER INFORMATION: synthetic peptide

<400> SEQUENCE: 34

Phe Glu Val Glu Asp Glu Asn Met Val Leu
1               5                   10

<210> SEQ ID NO 35
<211> LENGTH: 9
<212> TYPE: PRT
<213> ORGANISM: Artificial Sequence
<220> FEATURE:
<223> OTHER INFORMATION: synthetic peptide

<400> SEQUENCE: 35

Gly Tyr Trp Leu Pro Ser Tyr Lys Leu
1               5

<210> SEQ ID NO 36
<211> LENGTH: 10
<212> TYPE: PRT
<213> ORGANISM: Artificial Sequence
<220> FEATURE:
<223> OTHER INFORMATION: synthetic peptide

<400> SEQUENCE: 36

Lys Leu Lys Ser Ser Trp Ala Thr Gly Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic peptide

<400> SEQUENCE: 37

His Phe Cys Thr Thr Pro Ser Ser Ile Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: synthetic peptide

<400> SEQUENCE: 38

Lys Gln Leu Val Trp Arg Gly Ala Asn Val
1               5                   10

<210> SEQ ID NO 39
<211> LENGTH: 10
<212> TYPE: PRT
<213> ORGANISM: Artificial Sequence
```

```
<220> FEATURE:
<223> OTHER INFORMATION: synthetic peptide

<400> SEQUENCE: 39

Met Leu Glu Ala Gly Ala Glu Ala Asn Leu
1               5                   10

<210> SEQ ID NO 40
<211> LENGTH: 9
<212> TYPE: PRT
<213> ORGANISM: Artificial Sequence
<220> FEATURE:
<223> OTHER INFORMATION: synthetic peptide

<400> SEQUENCE: 40

Gln Tyr Val Leu Lys Val Thr Ser Val
1               5

<210> SEQ ID NO 41
<211> LENGTH: 10
<212> TYPE: PRT
<213> ORGANISM: Artificial Sequence
<220> FEATURE:
<223> OTHER INFORMATION: synthetic peptide

<400> SEQUENCE: 41

Leu Leu Leu Asn His Gly Ala Ala Arg Ile
1               5                   10

<210> SEQ ID NO 42
<211> LENGTH: 9
<212> TYPE: PRT
<213> ORGANISM: Artificial Sequence
<220> FEATURE:
<223> OTHER INFORMATION: synthetic peptide

<400> SEQUENCE: 42

Leu Leu Asn His Gly Ala Ala Arg Ile
1               5

<210> SEQ ID NO 43
<211> LENGTH: 9
<212> TYPE: PRT
<213> ORGANISM: Artificial Sequence
<220> FEATURE:
<223> OTHER INFORMATION: synthetic peptide

<400> SEQUENCE: 43

Val Val Val Asn Ala Tyr Glu His Ile
1               5

<210> SEQ ID NO 44
<211> LENGTH: 9
<212> TYPE: PRT
<213> ORGANISM: Artificial Sequence
<220> FEATURE:
<223> OTHER INFORMATION: synthetic peptide

<400> SEQUENCE: 44

Asp Phe Tyr His Ser Leu Phe Thr Val
1               5

<210> SEQ ID NO 45
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 45

Ala Ile Pro Leu Leu Ser Leu Pro Leu
1               5

<210> SEQ ID NO 46
<211> LENGTH: 10
<212> TYPE: PRT
<213> ORGANISM: Artificial Sequence
<220> FEATURE:
<223> OTHER INFORMATION: synthetic peptide

<400> SEQUENCE: 46

Ser Leu Pro Leu Ser Leu Lys Lys Tyr Leu
1               5                   10

<210> SEQ ID NO 47
<211> LENGTH: 10
<212> TYPE: PRT
<213> ORGANISM: Artificial Sequence
<220> FEATURE:
<223> OTHER INFORMATION: synthetic peptide

<400> SEQUENCE: 47

Glu Leu Ala Gly Ile Gly Ile Leu Thr Val
1               5                   10

<210> SEQ ID NO 48
<211> LENGTH: 9
<212> TYPE: PRT
<213> ORGANISM: Artificial Sequence
<220> FEATURE:
<223> OTHER INFORMATION: synthetic peptide

<400> SEQUENCE: 48

Arg Tyr Leu Arg Asp Gln Gln Leu Leu
1               5

<210> SEQ ID NO 49
<211> LENGTH: 9
<212> TYPE: PRT
<213> ORGANISM: Artificial Sequence
<220> FEATURE:
<223> OTHER INFORMATION: synthetic peptide

<400> SEQUENCE: 49

Glu Ala Asp Pro Thr Gly His Ser Tyr
1               5

<210> SEQ ID NO 50
<211> LENGTH: 8
<212> TYPE: PRT
<213> ORGANISM: Artificial Sequence
<220> FEATURE:
<223> OTHER INFORMATION: synthetic peptide

<400> SEQUENCE: 50

Arg Gly Tyr Val Tyr Gln Gly Leu
1               5

<210> SEQ ID NO 51
<211> LENGTH: 11
<212> TYPE: PRT
<213> ORGANISM: Artificial Sequence
<220> FEATURE:
<223> OTHER INFORMATION: synthetic peptide
```

```
<400> SEQUENCE: 51

Arg Tyr Leu Arg Asp Gln Gln Leu Leu Gly Ile
1               5                   10

<210> SEQ ID NO 52
<211> LENGTH: 12
<212> TYPE: PRT
<213> ORGANISM: Artificial Sequence
<220> FEATURE:
<223> OTHER INFORMATION: synthetic peptide

<400> SEQUENCE: 52

Gly Tyr Ile Ser Pro Tyr Phe Ile Asn Thr Ser Lys
1               5                   10

<210> SEQ ID NO 53
<211> LENGTH: 20
<212> TYPE: DNA
<213> ORGANISM: Artificial Sequence
<220> FEATURE:
<223> OTHER INFORMATION: synthetic peptide

<400> SEQUENCE: 53
accacagtcc atgccatcac                                              20

<210> SEQ ID NO 54
<211> LENGTH: 20
<212> TYPE: DNA
<213> ORGANISM: Artificial Sequence
<220> FEATURE:
<223> OTHER INFORMATION: synthetic peptide

<400> SEQUENCE: 54
tccaccaccc tgttgctgta                                              20

<210> SEQ ID NO 55
<211> LENGTH: 20
<212> TYPE: DNA
<213> ORGANISM: Artificial Sequence
<220> FEATURE:
<223> OTHER INFORMATION: synthetic peptide

<400> SEQUENCE: 55
ctgtcttgtt tggccatgtg                                              20

<210> SEQ ID NO 56
<211> LENGTH: 20
<212> TYPE: DNA
<213> ORGANISM: Artificial Sequence
<220> FEATURE:
<223> OTHER INFORMATION: synthetic peptide

<400> SEQUENCE: 56
gcgtctcctc atcttggttg                                              20
```